United States Patent
Buck et al.

(10) Patent No.: US 6,544,768 B1
(45) Date of Patent: Apr. 8, 2003

(54) MAMMALIAN SOLUBLE ADENYLYL CYCLASE

(75) Inventors: Jochen Buck, Old Greenwich, CT (US); Lonny R. Levin, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/568,407

(22) Filed: May 11, 2000

Related U.S. Application Data

(60) Provisional application No. 60/133,802, filed on May 11, 1999, now abandoned, and provisional application No. 60/161,534, filed on Oct. 26, 1999.

(51) Int. Cl.$^7$ .......................... C12N 9/88; C12N 15/00; C12N 5/00; C12N 1/20; C07H 21/04
(52) U.S. Cl. .................... 435/232; 435/325; 435/320.1; 435/252.3; 435/6; 536/23.2
(58) Field of Search .......................... 536/23.2; 435/232, 435/320.1, 325, 252.3, 6

(56) References Cited

PUBLICATIONS

Beltran C. et al., Biochemistry, 35:7591–7598 (1996).
Braun T, Proc. Soc. Exp. Biol. Med., 194: 58–63 (1990).
Braun T, Methods in Enzymology,195:130–136 (1991).
Caprioli J. and Sears M, The Lancet, 1:958–960 (1983).
Dessauer W and Gilman AG, J. Biol. Chem. 271:16967–16974 (1996).
Gerst JE et al., Molecular and Cellular Biology, 11:1248–1257 (1991).
Gordeladze JO and Hansson V, Molecular and Cellular Endocrinology, 23: 125–136 (1981).
Harrison RAP and Miller NGA, Molecular Reproduction and Development, 55:220–228 (2000).
Johnson RA et al., Mol. Pharmacology, 35:681–688 (1989).
Kawabe J et al., J. of Biol. Chem., 271:20132–20137 (1996).
Levin LR and Reed RR, J. Biol. Chem., 270:7573–7579 (1995).
Levin LR et al., Cell, 68: 479–489 (1992).
Mittag TW et al., Am. J. Physiol, 264:F1060–F1064 (1993).
Neer EJ and Murad F, Biochem. Biophys. Acta, 583:531–534 (1979).
Taussig R and Gilman AG, J. Biol. Chem., 270:1–4 (1995).
Visconti PE et al., J. Androl. 19:242–248 (1998).
Buck, Jochen, et al., "Cytosolic Adenylyl Cyclase Defines a Unique Signaling Molecule in Mammals", *Proc. Nat. Acad. Sci, USA*, 96:79–84 (1999).
Coudart–Cavalli, M.P., et al., "Bifunctional Structure of Two Adenylyl Cyclases from the Myxo Acterium Stigmatella Aurantiaca", *Biochimie*, 79:757–767 (1997).
Database EST, NCI–CGAhttp://www.ncbi.nlm.nih.gov/ncicgap, No. AW592474, hf43a12.x1 Soares–NFL–T–G–BC–S1 Homospiens cDNA clone IMAGE:2934622 3' similar to TR:Q9Z286 Q9Z286 Soluble Adenylyl Cyclase, Mar. 22, 2000.
Itoh, Masayoshi, et al., "Automated Filtration–Based High–Throughput Plasmid Preparation System", *Genome Research*; 9:463–470 (1999).
Buck, Jochen, et al., "Cytosolic Adenylyl Cyclase Defines a Unique Signaling Molecule in Mammals", *Proc. Nat. Acad. Sci, USA*, 96:79–84 (1999).
Coudart–Cavalli, M.P., et al., "Bifunctional Structure of Two Adenylyl Cyclases from the Myxo Acterium Stigmatella Aurantiaca", *Biochimie*, 79;757–767 (1997).
Database EST, NCI–CGAhttp://www.ncbi.nlm.nih.gov/ncicgap, No. AW592474, hf43a12.x1 Soares–NFL–T–G–BC–S1 Homospiens cDNA clone IMAGE:2934622 3' similar to TR:Q9Z286 Q9Z286 Soluble Adenylyl Cyclase, Mar. 22, 2000.
Itoh, Masayoshi, et al., "Automated Filtration–Based High Throughput Plasmid Preparation System", *Genome Research*; 9:463–470 (1999).

*Primary Examiner*—M. Monshipouri
(74) *Attorney, Agent, or Firm*—Darby & Darby

(57) ABSTRACT

The invention provides isolated animal soluble adenylyl cyclase and methods of modulating its expression and activity. Also provided are methods of utilizing soluble adenylyl cyclase for diagnosing pathological conditions and monitoring blood gases.

36 Claims, 12 Drawing Sheets

MSARRQELQDRAIVKIAAHLPDLIVYGDFSPERPSVKCFDGVLMFVDISG
FTAMTEKFSTAMYMDRGAEQLVEILNYYISAIVEKVLIFGGDILKFAGDA  100
LLALWKVERKQLKNIITVVIKCSLEIHGLFEAKEVEEGLDIRVKIGLAAG
HITMLVFGDETRNYFLVIGQAVDDVRLAQNMAQMNDVILSPNCWQLCDRS  200
MIEIERIPDQRAVKVSFLKPPPTFNFDEFFAKCMAFMDYYPSGDHKNFLR
LACMLESDPELELSLQKYVMEIILKQIDDKQLRGYLSELRPVTIVFVNLM  300
FKEQDKAEVIGSAIQAACVHITSVLKVFRGQINKVFMFDKGCSFLCVFGF
PGEKAPDEITHALESAVDIFDFCSQVEKIRTVSIGVASGIVFCGIVGHTV  400
RHEYTVIGQKVNIAARMMMYYPGIVTCDSVTYDGSNLPAYFFKELPKKVM
KGVADPGPVYQCLGLNEKVMFGMAYLICNRYEGYPLLGRVREIDYFMSTM  500
KDFLMTNCSRVLMYEGLPGYGKSQVLMEIEYLASQHENHRAVAIALTKIS
FHQNFYTIQILMANVLGLDTCKHYKERQTNLQNRVKTLLDDKYHCLLNDI  700
MQPQEIRDKVCVDLSVSSIPRELDSYLVEGSCGIPYYCEELLKNLDHHRI
LIFQQAEAEEKTNVTWNNLFKYSVKPTEDMYLYTSIAAGQKEACYLTSGV  800
RLKNLSPPASLKEISLVQLDSMSLSHQMLVRCAAIIGLTFTTELLFEILP
CWNMKMMIKALATLVESNVFDCFRSSKDLQLALKQNVTTFEVHYRSLSLK  900
SKEGLAYSEEEQLREMEGEVIECRILRFCRPIMQKTAYELWLKDQKKVLH
LKCARFLEESAHRCNHCRNRDFIPYHHFIADIRLNTLDMDTVKKMVKSHG 1000
FKTEDEVIFSKSEIPRKFKFPENISITETREKILHFFDNVIIKMRTSQDD
VIPLESCHCEELLQIVILPLAQHFVALEENNKALYYFLELASAYLILGDN 1100
YNAYMYLGEGERLLKSLTNEDSWSQTFEYATFYSLKGEICFNMGQMVLAK
KMLRKALKLLNRMFPCNLLSLTFQMHIEKNRLSHFMNQHTQEGSLPGKKL 1200
AQLFLQSSCFSLLWKIYSLNFFFHYKYYGRLAAIMQMNTSLETQNNFQII
KAFLDFSLYRHLAGYEGVWFKYEILVMEQLLNLPLKGEAFEIMAYAADAL 1300
GHIKFLTGHLDLAIELGSRAHKMWSLLRNPNKYHMVLCRLSKPLFLKSRY
KHLVQVLGWLWDLSVTEEHIFSKAFFYVCLDIMLYSGFIYRTFEECLEF 1400
IHHNEDNRILKFQSGLLLGLYSCIAVWYARLQEWDNFYKFSNRAKTLVTR
RTPTVLYYEGISRYMEGQVLHLQKQIEEQAENAQDSGVELLKALETLVAQ 1500
NTTGPVFYPRLYHLMAYVCILMGDGHSCDFFLNTALELSETQGNLLEKCW
LSMSKEWWYSAPELTGDQWLQTVLSLPSWDKIVSGNVTLQDVQKNKFLMR 1600
VNILDNPF

FIG. 1

Vector v-Ras sAC$_f$ sAC$_{fl}$ tmAC2

Gsα*

MAMMALIAN SOLUBLE ADENYLYL CYCLASE

This application claims domestic priority to U.S. provisional application No. 60/133,802, filed May 11, 1999 now abandoned and U.S. provisional application No. 60/161,534, filed Oct. 26, 1999 now abandoned.

The research leading to the present invention was supported, in part, by National Institute of Health grants Nos. DK48022, DK52797 and GM52891.

FIELD OF THE INVENTION

The present invention relates to isolated animal soluble adenylyl cyclase and its role in the regulation of the cAMP signaling pathway.

BACKGROUND OF THE INVENTION

Adenylyl cyclase (AC) is the effector molecule of one of the most widely used signal transduction pathways. Its product, cyclic AMP (cAMP), is a nearly universally utilized second messenger molecule, which mediates cellular responses to nutritional conditions and extracellular signals in organisms from prokaryotes to higher eukaryotes. cAMP has long been known to exert both stimulatory and inhibitory effects on cell growth and proliferation (Dumont, J. E., et al., Trends Biochem. Sci., 1989, 14:67–71; Rozengurt, E., Science, 1986, 234:161–6). In metazoans, a seemingly ubiquitous membrane-associated AC activity is encoded by a family of transmembrane adenylyl cyclases (tmACs) that mediate cellular responses to external stimuli.

Throughout the animal kingdom members of the transmembrane adenylyl cyclase (tmAC) superfamily synthesize cAMP to mediate communication between cells (Sunahara, R. K., et al., Annu. Rev. Pharmaco. Toxicol., 1996, 36: 461–80; Taussig, R., et al., J. Biol. Chem., 1995, 270:1–4). For example, in mammals, signals arising from other cells such as hormones, neurotransmitters, and olfactants, modulate tmAC activity via cell surface receptors and G proteins (Taussig, R., et al., Adv. Second Messenger Phosphoprotein Res., 1998, 32:81–98). A similar cAMP signaling cascade is present in other multicellular organisms, including Drosophila (Cann, M. J. et al., Adenylyl Cyclases, 32. Lippincott-Raven, 1998; Cann, M. J. et al., Adenylyl Cyclase, 32. Lippincott-Raven, 1999; Iourgenko, V., et al, FEBS Lett., 1997, 413:104–8; Iourgenko, V. et al., "A calcium inhibited Drosophila adenylyl cyclase (submitted); Levin, L. R., et al., Cell, 1992, 68:479–89), C. elegans (Bargmann, C. I., et al., Science, 1998, 282:2028–33; Berger, A. J., et al., J. Neurosci., 1998, 18:2871–80-; Korswagen, H. C. et al., Embo J., 1998, 17:5059–65), and Dictyostelium (Pitt, G. S. et al., Cell, 1991, 69:305–15). In contrast, the ACs found in unicellular eukaryotes and bacteria transmit nutritional information to the inside of the cell (Danchin, A., Adv. Second Messenger Phosphoprotein Res., 1991, 27:109–62).

Current models for cAMP signal transduction in mammals involve only transmembrane adenylyl cyclases (tmACs), which generate cAMP near the plasma membrane (Hempel, C. M., et al., Nature, 1996, 384:166–9; Sunahara, R. K., et al., Annu. Rev. Pharmacol. Toxicol., 1996, 36:461–80; Taussig, R., et al., J. Biol. Chem., 1995, 270:1–4). With the major effector of cAMP, the cAMP-dependent protein kinase (PKA), tethered to intracellular sites often far removed from the plasma membrane by a family of A Kinase Anchoring Proteins (AKAP) (Lester, L. B. et al., Recent Prog. Horm. Res., 1997, 52:409–29; Pawson, T., et al., Science, 1997, 278:2075–80) these models depend upon diffusion of cAMP past membrane-proximal targets to activate intracellular PKA at more distal sites. Furthermore, it must survive in a cytoplasm filled with phosphodiesterases (Beavo, J. A., et al., Mol. Pharmacol., 1994, 46:399–405; Bushnik, T., et al., Biochem. Soc. Trans., 1996, 24:1014–9). However the evidence for cAMP diffusion is based on exogenous addition of millimolar concentrations of cAMP (Bacskai, B. J., et al., Science, 1993, 260:222–6), and experiments which demonstrate diffusion of liberated PKA catalytic subunit (Bacskai, B. J., et al., Science, 1993, 260:222–6; Hempel, C. M., et al., Nature, 1996, 384:166–9). Thus there has not been a satisfactory explanation for the problems associated with how these models operate.

Soluble Adenylyl Cyclase

In addition to tmACs, another type of AC activity has been described in mammals, that of soluble adenylyl cyclase (sAC), which is thought to be expressed only in testis and sperm (Ahn, S., et al., Mol. Cell Biol., 1998, 18:967–77; Bacskai, B. J., et al., Science, 1993, 260:222–6). sAC activity appears to be biochemically and chromatographically different from tmACs, particularly a genetically engineered tmAC which is soluble, and soluble guanylyl cyclases previously described in testis (Neer, E. J., J. Biol. Chem., 1978, 253:5808–5812; Neer, E. J. et al., Biochim. Biophys. Acta, 1979, 583:531–534; Braun, T. et al., Biochim. Biophys. Acta, 1977,481:227–235). Unlike the known tmACs, sAC biochemical activity has been shown to depend on the divalent cation $Mn^{2+}$ (Braun, T and Dods, R. F., Proc. Natl. Acad. Sci. USA, 1975, 72:1097–1101), sAC is insensitive to G protein regulation (Braun, T. et al., Biochim. Biophys. Acta, 1977, 481:227–235), and sAC displays approximately 10-fold lower affinity for the substrate ATP (Km approximately equal to 1 mM) (Neer, E. J., J. Biol. Chem., 1978, 253:5808–5812; Gordeladze, J. O. et al., Mol. Cell Endocrinol., 1981, 23:125–136; Braun T., Methods Enzymol., 1991, 195:130–136) than the tmACs (Km approximately equal to 100 $\mu$M) (Johnson, R. A. et al., Methods Enzymol., 1994, 238:56–71). Based on these studies, this soluble form of AC was thought to be molecularly distinct from tmACs (Beltran, C. et al., Biochemistry, 1996, 35:7591–8; Berkowitz, L. A., et al., Mol. Cell Biol., 1989, 9:4272–81).

Semipurified soluble adenylyl cyclase activity is inhibited by submicromolar amounts of catechol estrogens (Braun, T., Proc. Soc. Exp. Biol. Med., 1990, 194:58–63). Braun demonstrated that the two hydroxyls of the catechol moiety were essential for the inhibitory interaction, estradiol and estrone were completely inactive. Catechols with aliphatic side chain like dopamine, L-dopa, and norepinephrine were able to inhibit sAC activity, but were 1,000 fold less potent.

Molecular evidence confirming that soluble AC represents a distinct form of adenylyl cyclase is lacking. Thus a need remains for the identification, cloning, characterization and purification of the signaling molecule having soluble adenylyl cyclase activity. There is a further need to modulate sAC activity in order to affect cell function.

Carbon Dioxide and Bicarbonate

Carbon dioxide ($CO_2$) is the end product of metabolism in animals. It is normally released into the atmosphere via breathing, but is also soluble in cell membranes. $CO_2$ combines with water in the presence of carbonic anhydrase (CA) to form carbonic acid ($H_2CO_3$) which dissociates to liberate a proton and bicarbonate ion ($HCO_3^-$).

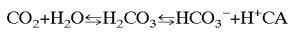

$$CO_2 + H_2O \leftrightharpoons H_2CO_3 \leftrightharpoons HCO_3^- + H^+ CA$$

By itself, this reaction reaches equilibrium after about 4 minutes. However, in most biological systems, due to the ubiquitous presence of carbonic anhydrase, bicarbonate/$CO_2$ equilibrium is reached nearly instantaneously (Johnson, L. R. *Essential Medical Physiology*, 1998, Phila. Lippincott-Raven).

In mammals, blood is a bicarbonate/$CO_2$ buffer system, and the relationship between blood pH, bicarbonate and $CO_2$ partial pressure can be described by the Henderson-Hasselbach equation:

$$pH = 6.1 + \log([HCO_3^-]/0.03 P_{CO_2})$$

This equilibrium in serum is tightly controlled in two ways; the kidneys regulate the bicarbonate concentration and the breathing frequency determines the concentration of carbon dioxide.

Bicarbonate is the carbon source for the initial reactions of gluconeogenesis and ureagenesis (Henry, Annu. Rev. Physiol., 1996, 58:523–538). Additionally, $CO_2$ and/or bicarbonate have been shown to modulate a number of physiological processes (i.e., diuresis, breathing, blood flow, cerebrospinal fluid formation, aqueous humor formation, and spermatocyte development). In most cases, the effects of $CO_2$ have been ascribed to as yet undescribed chemoreceptors, and the effects of bicarbonate are usually thought to be mediated by changes in cellular pH (Johnson, 1998).

Measurement of physiological levels of bicarbonate is typically determined indirectly by calculation from the direct measurement of carbon dioxide and pH using the Henderson Hasselbalch equation. However, a certain degree of error is inherent in indirect measurements, for example, due to artifacts in arterial blood sampling. Such errors may have grave consequences to the treatment of acutely ill patients, particularly neonates, and impairs the proper diagnosis of conditions such as respiratory and metabolic acidosis or alkalosis. Indeed, current state-of-the-art portable instruments, useful in emergency or point-of-site testing, such as the i-Stat®, or SenDx 100® only measure pH, $CO_2$, and $PO_2$ and calculate the bicarbonate levels based on these measurements. Therefore, there is a need for more accurate and direct determination of physiological bicarbonate levels.

Oncogenesis

In the yeast *Saccharomyces cerevisiae*, orthologs of the mammalian Ras oncogene control the cell's physiological response to nutritional status by modulating adenylyl cyclase activity (Mybonyi, K., et al, Mol. Cell Biol., 1990, 10:4518–23; Toda, T., et al., Cell, 1985, 40:27–36; Wigler, M., et al., Cold Spring Harb. Symp. Quant. Biol., 1988, 53:649–55). Yeast AC, which is encoded by the cyrl gene, is found in a complex with Cyclase Associated Protein (CAP); this association with CAP is required for Ras-responsiveness (Field, J., et al., Cell, 1990, 61:319–27; Gerst, J., et al., Mol. Cell Biol., 1991, 11:1248–57). Interestingly, cAMP regulation by Ras proteins in *S. cerevisiae* is the only biochemical pathway in yeast not thought to be conserved in mammals.

In mammals, a broad family of Ras-related, small GTP-binding proteins seems to be involved in cell growth, proliferation, and differentiation (Bos, J. L., et al., EMBO J., 1998, 17:6776–82). Ras genes are potent oncogenes; they are thought to be mutated in 30% of all human tumors. Although the mechanism of Ras transformation in human tumorigenesis has been the focus of intense research over the past years (Chang, E. H., et al., Nature, 1982, 297:479–83; Der, C. J., et al., Proc. Natl. Acad. Sci. USA 79:3637–40; Goldfarb, M., et al., Nature, 1982, 296:404–9; Parada, L. F., et al., Nature, 1982, 297:474–8), its mechanism of oncogenic transformation is still not completely understood. A protein kinase cascade involving Raf protein kinase activation of the MAPKinase cascade is downstream from Ras, as are activation of PI-3 kinase and the Ras-family member Ral (Gille, H., et al., J. Biol. Chem., 1999, 274:22033–40; Osada, M., et al., Mol. Cell Biol., 1999, 19:6333–44; Rosario, M., et al., Embo. J., 1999, 18:1270–9). However, these do not tell the entire story; a number of other genes have been proposed to play a role in Ras transformation (Tang, Y., et al., Mol. Cell Biol., 1999, 19:1881–91). Among the best characterized Ras effectors, constitutively active forms of Raf or the various MAPKinase can transform fibroblasts on their own, suggesting this kinase cascade can mediate at least part of the transforming functions of Ras. But oncogenic forms of these kinases are not as efficient at transforming fibroblasts as oncogenic forms of Ras, and inhibition of MAPKinase activity does not completely block transformation of Ras (Denouel-Galy, A., et al., Curr. Biol., 1998, 8:46–55; Yip-Schneider, M. T., et al., Int. J. Oncol., 1999, 15:271–9). In contrast, constitutive activation of PI-3 kinase does not transform cells, but inhibiting its activity is sufficient to prevent transformation by oncogenic Ras (Rodriquez-Viciana, P., et al., Cell, 1997, 89:457–67). Together, these data suggest that signaling through PI-3 kinase is necessary but not sufficient for oncogenic transformation by Ras proteins, while the MAPKinase pathway is at least partially sufficient, but does not appear to be necessary. Thus, there is a need to identify other components of Ras mediated transformation.

SUMMARY OF THE INVENTION

The present invention provides soluble adenylyl cyclase (sAC), a signaling enzyme which produces cAMP in eukaryotic, particularly non-yeast eukaryotic cells. The natural soluble form of adenylyl cyclase generates cAMP at a distance from the membrane, and thus closer to its required site of action. Accordingly, soluble adenylyl cyclase is useful in regulating or controlling cAMP production.

In a first aspect, the present invention provides an isolated nucleic acid molecule encoding a soluble adenylyl cyclase. The nucleic acid molecule is selected from the group consisting of a nucleic acid which encodes a polypeptide having an amino acid sequence as set out in SEQ ID NO. 1 or SEQ ID NO: 11, a splice variant thereof or an allelic variant thereof. Alternatively, the invention provides a nucleic acid molecule which hybridizes under stringent conditions to the nucleic acid sequence set out in SEQ ID NO: 2 or SEQ ID NO: 12. A nucleic acid molecule having at least a twenty nucleotides sequence identical to a corresponding twenty nucleotide sequence as set out in SEQ ID NO: 2 or SEQ ID NO: 12 is also encompassed. Yet a further alternative nucleic acid sequence encodes a soluble polypeptide having an amino acid sequence sufficiently duplicative of the soluble adenylyl cyclase encoded by SEQ ID NO: 1 or SEQ ID NO: 11 so that a polypeptide expressed from the nucleic acid molecule has the biological property of catalyzing the production of cyclic AMP, which polypeptide has a catalytic domain having a sequence that is not more than 16% similar to a catalytic domain of a mammalian transmembane adenylyl cyclase as determined by CLUSTAL analysis.

In one embodiment the soluble adenylyl cyclase is mammalian soluble adenylyl cyclase. In a preferred embodiment the adenylyl cyclase is human soluble adenylyl cyclase; rat soluble adenylyl cyclase is also provided.

The invention further provides a vector comprising the nucleic acid molecule as defined above. The vector can be an expression vector, in which the nucleotide sequence encoding soluble adenylyl cyclase is operably associated with an expression control sequence, e.g., for expression in human cells.

The invention further provides a host cell, preferably a mammalian cell, which comprises said expression vector.

The present invention also provides a method for producing recombinant soluble adenylyl cyclase comprising isolating soluble adenylyl cyclase expressed by a host cell containing an expression vector encoding a soluble adenylyl cyclase. In one embodiment, the soluble adenylyl cyclase is isolated using an anti-soluble adenylyl cyclase antibody.

The discovery of soluble adenylyl cyclase provides a mechanism for screening factors which modulate soluble adenylyl cyclase induced signaling. Thus the present invention provides a method of screening for a modulator of soluble adenylyl cyclase-induced signaling, which method comprises detecting inhibition of a signal of a soluble adenylyl cyclase-induced signal transduction pathway in a cell in the presence of a candidate compound wherein detection of inhibition of the signal indicates that the candidate compound is an inhibitor of soluble adenylyl cyclase-induced signaling. In one embodiment of the invention, the signal is cAMP generation. In this manner, cell proliferation, cell differentiation and apoptosis, control of which are diminished in pathological conditions such as cancer, can be modulated. Such modulation may have therapeutic and prophylactic benefit for those subjects suffering from such pathological conditions. Current treatment for these conditions, including chemotherapy and radiation therapy, are typically nonspecific and often have deleterious side effects. The identification of novel agents directed to a specific target to treat such conditions would be greatly advantageous.

The present invention also provides a method of modulating cAMP production by modulating the expression of soluble adenylyl cyclase. In this manner, for example, aberrant cell proliferation can be decreased or inhibited by regulating or modulating cAMP production.

With respect to decreasing cell proliferation, the present invention provides a method for decreasing or inhibiting soluble adenylyl cyclase expression such that cAMP production is decreased or inhibited and cell proliferation is decreased or inhibited.

Accordingly the present invention provides a method of regulating certain medical or pathological conditions in which cAMP production is implicated.

The present invention further provides a method of identifying factors which inhibit soluble adenylyl cyclase activity either by blocking expression of the soluble adenylyl cyclase gene or down regulating its ability to regulate cAMP metabolism. Such factors can thus be used in vivo or in vitro to regulate soluble adenylyl cyclase activity.

The present invention also provides a method for modulating soluble adenylyl activity by increasing soluble adenylyl cyclase activity. Soluble adenylyl cyclase can be activated or its activity can be increased when stimulation of cAMP production is desired. The present invention further provides a method of identifying factors that stimulate or enhance soluble adenylyl cyclase activity.

Applicants have specifically found that soluble adenylyl cyclase is potently stimulated by sodium bicarbonate. Controlling intracellular or extracellular bicarbonate concentrations provides an additional mechanism through which soluble adenylyl cyclase activity, and ensuing cAMP production, can be regulated.

In this regard, applicants have found that regulating cAMP concentrations by modulating soluble adenylyl cyclase activity can provide a means of modulating sperm capacitation. The present invention provides a method of regulating sperm capacitation by regulating expression of soluble adenylyl cyclase. In one embodiment, the invention provides a method for reducing or inhibiting male germ cell fertility by reducing or inhibiting soluble adenylyl cyclase activity and thereby inhibiting or decreasing capacitation of sperm. In one aspect the method comprises administering to a subject an agent that inhibits soluble adenylyl cyclase activity in an amount effective to decrease or inhibit cAMP production. In this manner, the fertilization of an ovum can be inhibited.

In another embodiment, the invention provides a method for increasing or enhancing the ability of sperm to fertilize an egg. With respect to this embodiment, the present invention provides a method of increasing sAC activity by, for example, treating sperm with a small molecule agonist, or using gene therapy to stimulate or enhance sperm capacitation. In this manner, the likelihood of fertilization of an ovum is increased or enhanced. This is particularly useful in procedures such as in vitro fertilization.

Applicants have also found that regulating cAMP concentrations by regulating soluble adenylyl cyclase expression provides a means of regulating insulin secretion of pancreatic islet cells. cAMP is needed for the release of insulin (Liang Y et al., Annual Review of Nutrition, 1994, 14:59–81). Addition of bicarbonate activates soluble adenylyl cyclase to increase cAMP production. With the discovery and isolation of soluble adenylyl cyclase, applicants provide a novel means of increasing or stimulating insulin release from the pancreas, when normal physiological mechanisms fail to do so, by increasing soluble adenylyl cyclase activity.

Thus, the invention provides a method of increasing insulin secretion of pancreatic islet cells comprising increasing soluble adenylyl cyclase activity.

The present invention further provides a method of treating glaucoma by reducing aqueous humor formation. With respect to this embodiment, aqueous humor formation, which is stimulated by cAMP signaling, can be reduced or inhibited by administering to a subject afflicted with glaucoma a modulator of sAC activity in an amount effective to reduce or inhibit bicarbonate dependent sAC activity to decrease the production of cAMP.

Applicants have also discovered that bicarbonate activates sAC in a direct, specific and pH independent manner. Accordingly, the present invention provides a method of quantifying bicarbonate in a body fluid using soluble adenylyl cyclase. The body fluid can be blood, urine, aqueous humor and the like.

In one aspect, the method of quantifying comprises contacting the body fluid with sAC. Contact of bicarbonate with sAC activates sAC and generates cAMP. The amount of bicarbonate in the sample can be correlated to the amount of cAMP detected. Measurement or detection of cAMP can be effected through a number of means including fluorescence, colorimetry and the like. Due to its specificity for sAC, a direct correlation to the amount of bicarbonate in the sample body fluid can be made using this method.

Applicants have further discovered that isolated soluble adenylyl cyclase is an oncogene. The isolated soluble adenylyl cyclase of the present invention is able to transform fibroblasts in vitro leading to loss of contact inhibition. Isolated soluble adenylyl cyclase and a truncated form of soluble adenylyl cyclase (sAC), transfected into cells transformed NIH3T3 cells. Soluble adenylyl cyclase was further demonstrated to support anchorage independent growth in soft agar. The Ras related protein, Rap1 which is a specific competitive inhibitor of Ras, inhibited soluble adenylyl cyclase transformation of cells. Thus soluble adenylyl cyclase provides a target for Ras family (or other small GTPases) regulation of cAMP metabolism in mammals. This discovery is surprising inasmuch that stimulation of transmembrane adenylyl cyclase activity blocks transformation of fibroblasts by oncogenic Ras (Chen, J., et al., Science, 1994, 263:1278–81; Smit, M. J. et al., Proc,. Natl. Acad. Sci. USA, 1998, 95:15084–9).

Thus, the invention provides a method of inhibiting unwanted cell proliferation in an animal, a mammal, a human by administering an effective amount of a soluble adenylyl cyclase binding protein peptide fragment wherein the protein inhibits soluble adenylyl cyclase expression. In another aspect, the functional activity of soluble adenylyl cyclase can be inhibited by administering a specific soluble adenylyl cyclase antisense molecule to cells that express functional soluble adenylyl cyclase.

The observation that soluble adenylyl cyclase is expressed in tumor cells further provides a diagnostic marker to detect the presence of pathological conditions in an animal, e.g., a mammal. In accordance with this aspect, the present invention provides a method of diagnosing the onset of, or the likelihood of onset of, or for monitoring the course and severity of a pathological condition derived from soluble-adenylyl cyclase activation, comprising detecting an increase in soluble adenylyl cyclase levels in a biological sample obtained from a subject suspected of suffering from such conditions.

The invention further provides compositions and kits for the diagnosis of conditions arising from soluble-adenylyl cyclase activation.

These and other aspects of the invention are more fully set forth in the Drawings, Detailed Description, and Examples.

DESCRIPTION OF THE FIGURES

FIG. 1 shows the predicted amino acid sequence of rat sAC (SEQ ID NO: 1). Amino acids in bold indicate presumptive catalytic domains, C1 and C2. Double-underlined amino acids correspond to sequences of tryptic peptides derived from the purified 48-kDa protein. Dotted underlined amino acids conform to a consensus P loop sequence, and underlined sequences are predicted to form a leucine zipper. Valine 469 is underlined and is the last amino acid in the catalytically active heterologously expressed truncated sAC ($sAC_t$).

FIG. 4a-Anti-sAC Western blot of testis (30 μg), sperm (5 μg), kidney (50 μg), and choroid plexus (50 μg).

FIG. 5a-Cellular cAMP accumulation was measured in stable cell lines expressing expression vector alone (diamonds) or $sAC_{tf}$ (squares) at the indicated concentrations of $NaHCO_3$ following growth for 24 hours under bicarbonate-free conditions. Data are expressed as cAMP formed as a percentage of total adenine nucleotides, and values represent averages of quadruplicate determinations with standard deviations indicated.

FIG. 6a-Purified $sAC_t$ was assayed in the presence of a range of concentrations of $NaHCO_3$ (0–80 mM) with 10 mM ATP and 40 mM $MgCl_2$. Data are expressed as nmol cAMP formed per minute per mg protein, and values are averages of triplicate determinations.

FIG. 7a-Phylogenetic relationship between catalytic domains from a variety of ACs aligned using CLUSTALW (DNA*) represented as an unrooted dendogram constructed using PROTPARS (PHYLIP 3.5). Numbers represent bootstrap confidence values. Accession numbers for the aligned amino acid sequences are sAC [rat sAC: AAD04035] tmAC1 [bovine Type 1: AAA799571, tmAC2 [rat Type 11: AAA40682], tmAC5 [rat Type V: Q04400], tmAC9 [mouse Type LX: CAA03415], D.d. AcrA [*Dictyostelium discoideum* AcrA: AAD50121], Asp. (*Anabaena spirulina*) cyaA [BAA13997], A.sp. cyaB1 [BAA139981], A.sp. cyaB2 [BAA13999], A.sp. cyaC [BAA14000], A.sp. cyaD [BAA140011, S.pl. (*Spirulina platensis*) CyaA [BAA22996], S.pl. CyaC [BAA22997], Syn. (Synechocystis sp.) CyaA1 [BAA16969], and Syn. CyaA2 [BAA17880].

*platensis* CyaC was assayed in the presence of a range of concentrations of $NaHCO_3$ (0–60 mM) with 100 μM ATP and 5 mM $MnCl_2$. Data are expressed as pmol cAMP formed per minute per mg protein, and values are averages of triplicate determinations.

FIGS. 8a–8f is a photograph of Giemsa-stained foci formed in NIH3T3 cells transfected with vector alone (a), v-Ras (b), truncated soluble adenylyl cyclase (c, $sAC_t$), full length soluble adenyl cyclase (d, $sAC_{fl}$), transmembrane adenylyl cyclase Type II (e, tmAC2), or constitutively active Gsα* protein (f).

Figure 9:
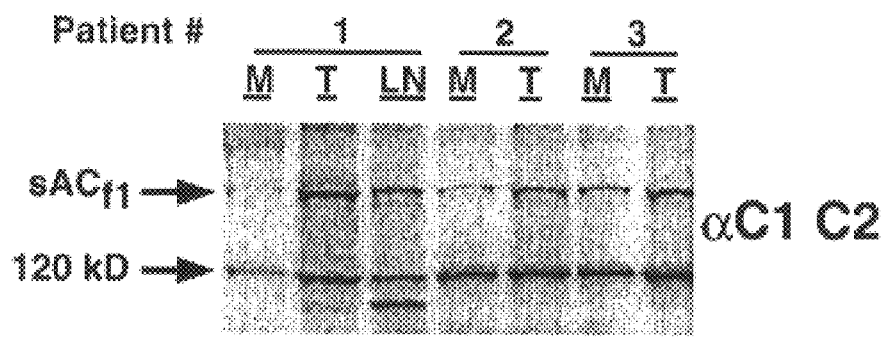

FIG. 9 shows sAC expression in human colon carcinoma compared to normal colon. Western blot analysis with indicated sAC-specific antisera against normal colon mucosa (M), colon carcinoma (T), or in one case, a biopsied lymph node (LN) from three, independent cancer patients. sAC protein is specifically unregulated in patients #1 and #2.

DETAILED DESCRIPTION

In accordance with the present invention, a distinct class of soluble adenylyl cyclases is presented. Applicants have surprisingly discovered that soluble adenylyl cyclase (sAC) is expressed not only in testis, but throughout animal tissue types including brain, kidney, skeletal muscle, liver, lung, spleen and heart. sAC activity has been detected in sea urchin sperm.

The present invention is based, in part, on the purification, cloning and characterization of soluble animal adenylyl cyclase (sAC). sAC was purified from cytosolic extracts of rat testes. This catalytically active purified form of sAC was identified as a 48-kD protein by SDS-polyacrylamide gel electrophoresis (SDS-PAGE). The purified 48 kD species corresponds to the N-terminal of the predicted protein. The sAC activity was only detected in vitro in the presence of $Mn^{2+}$-ATP and was unresponsive to either forskolin or GTPγS. However, sAC activity was stimulated by bicarbonate in the presence of $Mg^{2-}$-ATP.

The full length cDNA predicts a protein of about 187 kD. Full-length sAC is proteolytically processed into multiple developmentally regulated isoforms postulated to serve distinct cellular functions. At least five isoforms have been identified having apparent molecular weights of 190 kD, 150 kD, 120 kD, 48 kD and 45 kD as determined by SDS-PAGE, with detection by sAC specific antisera described herein. The expression of sAC appears to be regulated during cell development (for example, in sperm) and varies in expression between individual cell lines.

It is contemplated as part of the present invention that sAC can be isolated from body tissue or can be produced by recombinant DNA methods or synthetic peptide chemical methods that are well known to those of ordinary skill in the art.

sAC Nucleic Acid and Protein

The sAC gene was identified in rat, mouse, pig, and human and encodes a cytosolic form of adenylyl cyclase that is distinct from the previously characterized mammalian tmACs. Not only is sAC not a transmembrane protein, but its catalytic domains are more closely related to the catalytic portions of bacterial ACs than they are to the catalytic domains of any other eukaryotic cyclase. In contrast, the mammalian tmACs, which are distantly related to these bacterial ACs and sAC, more closely resemble other invertebrate (Drosophila) and lower eukaryotic (Dictyostelium) ACs. The amino acid sequence of the isolated rat sAc molecule is shown in FIG. 1 and in SEQ ID NO: 1. The amino-terminal portion of approximately 50 kD, encompassing both catalytic domains C1 and C2 is sufficient for sAC enzymatic activity. Using the CLUSTAL method of sequence comparison provided with the MEGALIGN program manufactured by DNA Star, and using standard default parameters, sAC C1 and C2 are 24.3% similar to each other. Both C1 and C2 are only between 10–16% similar to the catalytic domains of the various mammalian transmembrane adenylyl cyclases. C1 is 14.1% similar to yeast (*Saccharomyces cerevisiae*) adenylyl cyclase. C2 is 14.9% similar to yeast (*Saccharomyces cerevisiae*) adenylyl cyclase.

In contrast, C1 is 35.9% similar to (Cyanobacterial) *Anabaena spirulensis* CyaB1 and 33.2% similar to Anabaena spirulensis CyaA, while C2 is 25.9% similar to *Anabaena spirulensis* CyaA and 27.7% similar to Anabaena spirulensis CyaB1. A sAC-like cyclase has also been identified in cyanobacteria. Cyanobacteria are gram negative bacteria that, in the presence of sunlight, water and carbon dioxide, perform oxygen-evolving photosynthesis similar to plants. They respond to changes in environmental availability of these raw materials, such as shifts between light and dark and between low pH and high pH, via changes in their intracellular cAMP concentration (Ohmori, Plant Cell Physiol.,1989, 30:911–914; Ohmori et al., Arch. Microbiol., 1988, 150:203–204), and membrane permeable cAMP analogs stimulate metabolism, i.e. the activity of respiration, in the cyanobacteria *Spirulina platensis* (Ohmori et al., Plant Cell Physiol.,1992, 33:21–25). Cyanobacterial adenylyl cyclases may provide the link between light sensation and cAMP generation. Genetic disruption of a particular adenylyl cyclase isoform causes loss of the light-dark response in the cyanobacterium Anabaena (Katayama and Ohmori, J. Bacteriol., 1997, 179:3588–93) and the cyaC adenylyl cyclase from *Spirulina platensis* is thought to be directly stimulated by light via its histidine kinase phosphotransfer regulatory domain (Kasahara et al., Plant Cell Physiol., 1997, 38:828–36; Kasahara and Ohmori, 1999, J. Biol. Chem. 274:15167–15172). Applicants have found that cyaC is directly stimulated by bicarbonate.

The anti-catalytic domain (C1-C2) antisera on tested sea urchin sperm membranes and on a partially purified fraction containing sea urchin sperm adenylyl cyclase activity. The results of a Western blot show, particularly in the partially purified sperm cyclase containing fraction, a band at 190 kD, which is the size predicted for sea urchin sperm cyclase (Bookbinder L H et al., J. Biol. Chem., 1990, 111:1859–1866). In addition, an immunoreactive band at approximately 120 kD was detected, suggesting that proteolytic processing leading to distinct sAC isoforms is also conserved between species.

A soluble adenylyl cyclase is a protein having an amino acid sequence substantially similar to that of the isolated sAC described herein having sAC activity. The term substantially similar when used in reference to sAC amino acid sequences means an amino acid sequence having sAC activity and having a molecular weight of approximately 187 kD.

The amino acid sequence of the sAC of the present invention may vary depending on which isoform-cell or tissue the sAC is derived.

It is also contemplated that the molecule sAC can be a fragment of the full length sAC molecule, having sAC activity. In one embodiment a sAC can have a molecular weight of approximately 48–53 kD and an amino acid sequence substantially similar to the amino terminal portion of the rat sAC sequence SEQ ID NO: 1. The soluble adenylyl cyclase can be a chimeric variant or modified derivatives, including a chemically modified derivative including modification by PEGylation. The human sAC locus has been sequenced as part of the Genome Project. It is encoded by more than 30 exons that are spread across two overlapping PAC (P1-derived artificial chromosome) clones mapping to 1q24 human PAC clones. GenBank reference Accession Numbers HS295C6 Human DNA sequence from PAC 295C6 on chromosome 1Q24, HS313L4 Human DNA sequence from PAC 313L4 on chromosome 1q24. The human sAC amino acid sequence is set out as the sequence of SEQ ID NO: 11; the DNA sequence is set out as the sequence of SEQ ID NO: 12.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants."

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Clustal Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared. Finally, for purposes of the invention, a functional-conservative variant includes a truncated form of the protein that performs its function, or splice variants, or proteolytic fragments of the proteins such as sAC isoforms characterized by molecular weights 190 kD, 150 kD, 120 kD, 48 kD and 45 kD. Functional-conservative variants also include any polypeptides that have the ability to elicit antibodies specific to a designated polypeptide.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA), A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al, supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of sAC, or to detect the presence of nucleic acids encoding sAC. In a further embodiment, an oligonucleotide of the invention can form a triple helix with a sAC DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of sAC of the invention, particularly to suppress sAC regulation of cAMP. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic inter-sugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. No. 5,792,844 and U.S. Pat. No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

General Definitions

As used herein, the term "isolated" means that the soluble adenylyl cyclase is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated MRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell.

As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Protein purification methods are well known in the art and a specific example of a method for purifying sAC is provided in the examples below. For example, nucleic acids can be purified by precipitation, chromatography (including preparative solid phase chromatography, oligonucleotide hybridization, and triple helix chromatography), ultracentrifutigation, and other means. Polypeptides and proteins can be purified by various methods including, without limitation, preparative disc-gel electrophoresis, iso-electric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a poly-histidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, particularly in biology, the term "about" can mean within an order of magnitude of a given value, and preferably within one-half an order of magnitude of the value.

The term "inhibitor" is used herein to refer to a compound that can block signaling in the signal transduction pathway described herein. Such an inhibitor may directly affect sAC function, substrate recognition, or activation. Preferably, an inhibitor discovered in accordance with the invention is specific for signals of sAC-induced signaling. Such an inhibitor may also be termed an antagonist.

The term "agonist" is used herein to refer to a compound that can induce signaling in the signal transduction pathway described herein. Preferably an agonist discovered in accordance with the invention is specific for signals of sAC-induced signaling.

"Screening" refers to a process of testing one or a plurality of compounds (including a library of compounds) for some activity. A "screen" is a test system for screening. Screens can be primary, i.e., an initial selection process, or secondary, e.g., to confirm that a compound selected in a primary screen (such as in a binding assay) functions as desired (such as in a signal transduction assay). Screening permits the more rapid elimination of irrelevant or non-functional compounds, and thus selection of more relevant compounds for further testing and development. "High throughput screening" involves the automation and robotization of screening systems to rapidly screen a large number of compounds for a desired activity.

Molecular Biology—Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); DNA *Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B.ÊPerbal, *A Practical Guide To Molecular Cloning* (1984); F. M. Ausubel et al. (eds.), *Current Protocols in Molecular Biology*, John Wiley & Sons, Inc. (1994).

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"). A "recombinant DNA molecule" is a DNA molecule that has undergone a molecular biological manipulation.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

An "opening reading frame" (ORF) as used herein is a region of a polynucleotide sequence having a start and codon and which may encode a polypeptide. This region may represent a portion of a coding sequence or may comprise a total coding sequence for the polypeptide.

A "complement" of a nucleic acid sequence as used herein refers to the "antisense" sequence that participates in Watson-Crick base-pairing with the original sequence.

The term "gene", also called a "structural gene" means a DNA sequence that codes for or corresponds to a particular sequence of amino acids, which comprise all or part of one or more proteins or enzymes. A gene as used herein may or may not include non-transcribed regulatory DNA sequences, such as promoter sequences, which determine for example the conditions under which the gene is expressed. Furthermore, a transcribed portion of the gene may include 5'- and 3'-untranslated sequences and introns in addition to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively (or operably) associated with" of transcriptional and translational control sequences in a cell when RNA polymerase transcribes the coding sequence into mRNA, which is then trans-RNA spliced (if it contains introns) and translated into the protein encoded by the coding sequence. The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation"

means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

The term "expression system" means a host cell and compatible vector under suitable conditions, e.g. for the expression of a protein coded for by foreign DNA carried by the vector and introduced to the host cell. Expression systems include mammalian host cells and vectors. Suitable cells include C12 cells, CHO cells, HeLa cells, 293 and 293T (human kidney cells), mouse primary myoblasts, and NIH 3T3 cells.

Vectors

A wide variety of host/expression vector combinations may be employed in expressing DNA sequences encoding sAC other proteins involved in cAMP signaling, or inhibitors of sAC such as antisense nucleic acids or anti-sAC intracellular antibodies. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31–40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, Nature 290:304–310, 1981), the promoter contained in the 3' long terminal repeat of Rous sarcoma virus (Yamamoto, et al., Cell 22:787–797, 1980), the herpes thymidine kinase promoter (Wagner, et al., Proc. Natl. Acad. Sci. U.S.A. 78:1441–1445, 1981), the regulatory sequences of the metallothionein gene (Brinster, et al., Nature 296:39–42, 1982); prokaryotic expression vectors such as the β-lactamase promoter (Villa-Komaroff, et al., Proc. Natl. Acad. Sci. U.S.A. 75:3727–3731, 1978), or the tac promoter (DeBoer, et al, Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and control regions that exhibit hematopoietic tissue specificity, in particular: immunoglobin gene control region, which is active in lymphoid cells (Grosschedl et al., Cell, 38:647, 1984; Adames et al., Nature, 318:533, 1985; Alexander et al., Mol. Cell Biol., 7:1436, 1987); beta-globin gene control region which is active in myeloid cells (Mogram, et al., Nature 315:338–340, 1985; Kollias, et al, Cell 46:89–94, 1986), hematopoietic stem cell differentiation factor promoters; erythropoietin receptor promoter (Maouche, et al., Blood, 15:2557, 1991), etc; and control regions that exhibit mucosal epithelial cell specificity.

A vector can be introduced in vivo in a non-viral vector, e.g., by lipofection, with other transfection facilitating agents (peptides, polymers, etc.), or as naked DNA. Synthetic cationic lipids can be used to prepare liposomes for in vivo transfection, with targeting in some instances (Felgner, et. al., Proc. Natl. Acad. Sci. U.S.A. 84:7413–7417, 1987; Felgner and Ringold, Science 337:387–388, 1989; see Mackey, et al, Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931). Recently, a relatively low voltage, high efficiency in vivo DNA transfer technique, termed electrotransfer, has been described (Mir et al., C.P. Acad. Sci., 321:893, 1998; WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S Pat. Nos. 5,580,859 and 5,589,466 disclose delivery of exogenous DNA sequences, free of transfection facilitating agents, in a mammal.

Also useful are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional protein or polypeptide (as set forth above) can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glycoprotein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, CA; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Antibodies to sAC

According to the invention, sAC polypeptides produced recombinantly or by chemical synthesis, and fragments or other derivatives or analogs thereof, including fusion proteins, may be used as an immunogen to generate antibodies that recognize the sAC polypeptide. Such antibodies include but are not limited to polyclonal, monoclonal, chimeric, single chain, Fab fragments, and an Fab expression library. Such antibodies are specific for sAC or specific portions of sAC.

Various procedures known in the art may be used for the production of polyclonal antibodies to sAC polypeptide or derivative or analog thereof. For the production of antibody, various host animals can be immunized by injection with the sAC polypeptide, or a derivative (e.g., fragment or fusion protein) thereof, including but not limited to rabbits, mice, rats, sheep, goats, etc. In one embodiment, the sAC polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the sAC polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). Production of human antibodies by CDR grafting is described in U.S. Pat. Nos. 5,585,089, 5,693,761, and 5,693,762 to Queen et al., and also in U.S. Pat. No. 5,225,539 to Winter and International Patent Application PCT/WO91/09967 by Adau et al. In an additional embodiment of the invention, monoclonal antibodies can be produced in germ-free animals (International Patent Publication No. WO 89/12690, published Dec. 28, 1989). In fact, according to the invention, techniques developed for the production of "chimeric antibodies" (Morrison et al., J. Bacteriol. 159:870, 1984); Neuberger et al., Nature 312:604–608, 1984; Takeda et al., Nature 314:452–454, 1985) by splicing the genes from a mouse antibody molecule specific for a sAC polypeptide together with genes from a human antibody molecule of appropriate biological activity can be used; such antibodies are within the scope of this invention. Such human or humanized chimeric antibodies are preferred for use in therapy of human diseases or disorders, since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. 4,946,778) can be adapted to produce sAC polypeptide-specific single chain antibodies. An additional embodiment of the invention utilizes the techniques described for the construction of Fab expression libraries (Huse et al., Science 246:1275–1281, 1989) to allow rapid and easy identification of monoclonal Fab fragments with the desired specificity for an sAC polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a sAC polypeptide, one may assay generated hybridomas for a product which binds to a sAC polypeptide fragment containing such epitope. For selection of an antibody specific to a sAC polypeptide from a particular species of animal, one can select on the basis of positive binding with sAC polypeptide expressed by or isolated from cells of that species of animal.

The foregoing antibodies can be used in methods known in the art relating to the localization and activity of the sAC polypeptide, e.g., for Western blotting, imaging sAC polypeptide in situ, measuring levels thereof in appropriate physiological samples, etc. using any of the detection techniques mentioned above or known in the art. Such antibodies can be used to identify proteins that interact with sAC.

In a specific embodiment, antibodies that agonize or antagonize the activity of sAC polypeptide can be generated. They can also be used to regulate or inhibit sAC activity intracellularly, i.e., the invention contemplates an intracellular antibody (intrabody), e.g., single chain Fv antibodies (see generally, Chen, Mol. Med. Today, 3:160–167, 1997; Spitz et al., Anticancer Res., 16:3415–3422, 1996; Indolfi et al., Nat. Med., 2:634–635, 1996; Kijima et al., Pharmacol. Ther., 68:247–267, 1995).

The antibodies that specifically bind to the sAC or peptides or fragment, thereof can be used in diagnostic methods and kits that are well known to those of skill in the art to detect or quantify sAC in bodily tissue. Results from these test can be used to diagnose or detect the occurrence of a pathological condition mediated by sAC expression, for example tumor formation.

sAC: Oncogene sAC is a new oncogene that functions in the oncogenic signaling pathway of mammalian Ras proteins. sAC interacts with the mammalian ortholog of yeast CAP, which is required for Ras-responsiveness of yeast cyclase. When mammalian CAP is co-expressed with sAC, sAC activity increases approximately four-fold. In addition, two out of three human colon carcinomas, which often harbor oncogenic Ras mutations, when tested had elevated levels of sAC isoforms. sAC expression was upregulated in pre-cancerous tissue in Min mice, a model system for generic predisposition of colon cancer.

The identification of sAC as a unique form of mammalian adenylyl cyclase further provides a new potential target for Ras regulation of cAMP signaling an mammals.

A truncated form of sAC ($sAC_t$) was highly active and was able to transform NIM 3T3 cells by focus-fonning assay. It produced as many foci as the oncogenic form of Ras. Oncogenic transformation of NIH 3T3 cells is often a consequence of uncontrolled cell growth (i.e., by loss of contact inhibition) and/or decreased cell death (i.e., by oncogenes such as p53, Rb, APC and Ras (Joneson, T. and D. Bar-Sagi (199), Mol. Cell Biol. 19: 5892–901;

Leblanc, V et al., (1999) Oncogene 18: 4884–9)). Full-length sAC ($sAC_{fl}$) was less oncogenic, inducing more foci than vector alone, but less than $sAC_t$. We also found that $sAC_t$ and $sAC_{fl}$ support achorage independent growth in soft agar.

Rap1 protein, which selectively blocks transformation by oncogenic Ras proteins, blocked transformation by $sAC_t$, suggesting that sAC and Ras may share their biochemical mechanism of transformation.

sAC Modulators

The present invention further provides various screening assays for identifying sAC modulators, i.e., inhibitors or agonists, and particularly sAC induced activation of cAMP, useful as targets for diagnosis and/or treatment of conditions arising from inappropriate activation or a deficiency of sAC. The screening assays of the invention are particularly advantageous by permitting rapid evaluation of cellular response. Biological assays, which depend on cell growth, survival, or some other response require substantial amounts of time and resources to evaluate. By detecting individual signals in the sAC-induced signal transduction pathway, the present invention short-circuits tedious and tine consuming biological assays. Furthermore, signal transduction assays can often be performed with very small amounts of material.

The present invention contemplates screens for small molecule compounds, including ligand analogs and mimics, as well as screens for natural compounds that bind to and agonize or antagonize sAC signal transduction in vivo. Such agonists or antagonists may, for example, interfere in the signaling cascade induced by sAC generated cAMP. For example, natural products libraries can be screened using assays of the invention for such molecules. As used herein, the term "compound" refers to any molecule or complex of more than one molecule that affects sAC signal transduction. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc.

In another aspect, synthetic combinatorial libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 94/28028) and the like can be used to screen for compounds according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

Thus contemplated within the scope of the invention is to use the sAC signaling pathway as an approach to find modulators of sAC activity. For example, inhibiting sAC activity provides a means of preventing, reducing slowing pathological conditions which may result from sAC hyperactivity. For example, because sAC is an oncogene upregulated in human tumors, which might contribute to induction or maintenance of human cancers, defining sAC's signaling cascade will establish whether it could be possible to inhibit sAC activity as a means to slowing or preventing growth of cancers. In this respect pharmacologic and molecular genetic approaches can be used.

The present invention provides numerous methods for detecting signals, including but not limited to directly detecting cAMP levels. Preferably, gene expression is detected using a reporter gene assay. Alternatively, a downstream element of a signal transduction pathway can be modified to have reporter activity. Reporter genes for use in the invention encode detectable proteins, including, but are by no means limited to, chloramphenicol transferase (CAT), β-galactosidase (β-gal), luciferase, green fluorescent protein, alkaline phosphatase, and other genes that can be detected, e.g., immunologically (by antibody assay).

The β-galactosidase screen for identifying sAC inhibitors uses a previously described protocol (Tang W J and A G Gilman 1995) Science 268:1769–72) examining the engineered, soluble form of transmembrane adenylyl cyclases (tmACs). Using the strains and plasmids described therein, we have demonstrated that the truncated, highly active form of sAC, $sAC_t$, will complement the cya mutation in *Escherichia coli*. Basically, *E. Coli* harboring a mutated adenylyl cyclase (cya) gene will grow WHITE on an indicator plate referred to as MacConkey agar while wild type *E. coli* are usually red. The red colony color indicates the ability to synthesize cAMP and is directly due to a change in the pH of the agar where the colony is growing. The engineered soluble form of tmACs can generate sufficient cAMP to complement the cya mutation and cause bacteria which express it to grow as red colonies. We recently showed that cya bacteria which express $sAC_t$ also form red colonies revealing that it too is able to generate sufficient amounts of cAMP in bacteria. To identify compounds which specifically inhibit sAC and not tmACs, one could screen a library of compounds against two strains of bacteria, one expressing the engineered soluble form of tmAC and the other expressing $sAC_t$. Any compound turning $sAC_t$ expressing bacteria white while not affecting the soluble tmAC expressing bacteria, must be selectively preventing sAC from making cAMP.

Other known "target" genes involved in sAC activation can be tested. Chip-based technologies could be employed to determine transcriptional targets specifically involved in sAC transformation. 'Gene chips' can be used to explore the entire panoply of genes regulated by $sAC_t$. Using this method a specific transcriptional target of sAC can be identified, and the gene's promoter linked to a reporter construct such as Green Fluorescent Protein (GFP), β-galactosidase, luciferase, or chloramphenicol acetyltransferase (CAT). We can then use reporter gene expression as a readout of sAC pathway activation as a primary screen for inhibitors or activators of the sAC pathway. In a specific embodiment, these assays explore the sAC transformation pathway.

sAC Inhibitors

Specific inhibitors of sAC include anti-sense and ribozymes, anti-sAC intracellular antibodies, and small molecule inhibitors discovered as set forth herein, including catechol estrogens.

Different putative inhibitors of sAC activity are tested by measuring production of cAMP at different fixed inhibitor concentrations or under other conditions. Various parameters can be analyzed, which include:

(1) Product inhibition. The products of the cyclization reaction, cAMP and pyrophosphate can be tested for their ability to inhibit cAMP formation.

(2) Inhibition with alternatively used trinucleotides. sAC's ability to recognize and/or utilize other nucleotides can be tested, for example the nucleotide triphosphates GTP, CTP, TTP, UTP and ITP. If any nucleotide competitively inhibits ATP with millimolar or submillimolar $K_i$, we will test the possibility that sAC is able to utilize it as substrate to synthesize the corresponding cyclic nucleotide. In all cases, except GTP conversion to cGMP, in vitro assay would be used for the corresponding cyclase activity;

(3) P site ligands and inhibitors of other ATP-utilizing enzymes. P site inhibitors are adenine nucleotides which inhibit tmAC activity (Johnson, R. A., et al., Methods Enzymol., 1994, 238:56–71). sAC's previously described insensitivity to various P-site inhibitors ((Johnson, R. A., et al., Methods Enzymol., 1994, 238:56–71; Johnson, R. A., et al., Mol. Pharmacol., 1989, 35:681–8) has been confirmed using the P site ligand 2',3'-dideoxyadenosine and the truncated form of sAC. Various P site ligands less effective at inhibiting tmACs may prove usefull for sAC, in the hope that they may prove more efficacious at inhibiting sAC. Different physiological (i.e. ADP, AMP) and nonphysiological nucleotides (i.e. ATPγS, AMP(NH)P) can also be tested.

Catechol Estrogens The catechol estrogens (2- and 4-hydroxtestradiol and 2- and 4-hydroxyestrone) are physiological estrogen derivatives with distinct biological effects compared with their parent compounds. In hypothalamus and pituitary, concentrations of catechol estrogens are at least ten times higher than the parent estrogens (Paul, S. M., et al., Science, 1997, 197:657–9). Contrary to estrogens, catechol estrogens inhibit cAMP accumulation in the hypothalamus (Paul, S. M., et al, Nature, 1977, 266:559–61).

Catechols are labile molecules easily oxidized to quinones, especially in the presence of divalent cations like $Mn^{+-}$ (which are present at millimolar concentration in sAC enzyme assays). Quinone formation can be prevented by antioxidants. Therefore, quinones, and not catechols, could be responsible for suppression of cAMP production and the antioxidants could diminish potency of sAC inhibition by preventing the conversion of catechols to quinones.

Various compounds such as 2- and 4-hydroxyestradiol, 2- and 4-hydroxystrone (Steraloid, Inc.), and not their parent compounds estradiol and estrone, affect sAC activity. This can be shown using purified sAC isoforms in the presence and absence of antioxidants. The mode of inhibition (i.e., competitive or noncompetitive) and the corresponding IC and Ki values can also be determined.

Binding affinities to the distinct sAC isomers for catechols can be determined using tritiated 2-hydroxy estrone (Dupont-NEN). sAC isomers can be incubated with different amounts of [$^3$H]2-hydroxy estrone and unbound ligand is separated by small gel filtration columns. Nonspecific binding is determined by adding excess unlabelled 2-hydroxy estrone. In competition studies, [$^3$H]2-hydroxy estrone will be competed with other catechols and catechol estrogens. Data will be analyzed using the KELL package of binding analysis programs (Biosoft).

In order to determine whether catechol estrogen itself or an oxidized product is the inhibitor of sAC, isomers are incubated with [$^3$H]2-hydroxy estrone, and unbound catechol estrogen is separated by gel filtration. Protein is dilapidated and the lipids separated using reversed phase HPLC. Oxidized catechol estrogens would have different elution times than catechol estrogens. If this would be the case, the structure of the catechol derivative is determined. A combination of mass spectroscopy, NMR and circular dischroism spectroscopy would be used to characterize the structure of small lipophilic molecules. Even if not physiologically relevant, the structure of the respective bioactive catechol estrogen derivative would be a lead compound to develop drugs specifically inhibiting oncogenic sAC.

Using sAC-inducible and control cell lines, it can be determined whether sAC transforms cells in the presence of commercially available inhibitors which prevent signaling through Ras (N-acetyl-S-farnesyl-L-cysteine, or AFC, which blocks Ras famesylation), the Raf/MAP kinase pathway (PD-98095 which is selective inhibitor of the MAP kinase kinase, MEK), and the phosphoinositide pathway (LY 294002 or Wortmannin, which are potent and selective inhibitors of PI-3 kinase). We will also test the Ral effector pathway by transfection of a dominant negative Ral mutant (Goi, T., et al., Mol Cell Biol., 1999, 19:1731–41).

sAC Binding Proteins

Regulators of sAC transformation, such as Rap1, can be evaluated in sAC inducible cell lines by using effector protein binding domains which preferentially bind to sAC induced expressed proteins.

A two-hybrid screen can be used to identify sAC interacting proteins. Using sAC as 'bait' (i.e., fused to the GAL4-DNA binding domain) to target libraries consisting of cDNAs generated from NIH 3T3 cells can be screened, which are transformed by sAC and from cell lines derived from colon tumors, which upregulate sAC protein. The screen is performed in the presence and absence of mammalian CAP engineered to contain a nuclear localization signal. Including CAP protein permits identification of any genes interacting exclusively with the sAC-CAP heteromer. Others have used bridging proteins in two-hybrid selections before; for example, in a directed two-hybrid screen. Ras interaction with MAPKinase kinase required the inclusion of nuclear localized Raf (Van Aelst, L., et al., Proc. Natl. Acad. Sci. USA, 1993, 90:6313–7).

Various reagents for confirming an interaction and identifying the interacting proteins are available. For example, if previously known and studied genes are found, antisera may be used to test for co-immunoprecipitation of sAC and the newly identified potential binding partner. Alternatively, purified protein would permit attempting in vitro mixing experiments as described above for CAP or bacterially express GST fusion proteins of the target proteins. If soluble, this will facilitate rapid purification to test in vitro binding using purified components.

Potential targets through which sAC transformation can be regulated, include modulating the activity of another, already known, oncogenic signaling pathway. For example, Fos transcription, or more often reporter expression from a Fos gene promoter, can be used as a reliable indicator of transforming pathway activation (Ahn, S., et al., Mol. Cell Biol., 1998, 18:967–77). Fortunately, there exist a large number of readily available reagents to test whether other known oncogenes or their targets are required for sAC transformation. Using such reagents, sAC transformation can be prevented by blocking signaling through known oncogenic pathways. For example, Ras signaling cascade possesses excellent examples of the various reagents available; including a dominant negative (Feig, L. A., et al., Mol. Cell Biol., 1988, 8:3235–43; Schaap, D., et al., J. Biol. Chem., 1993, 268:20232–6) or effector selective (White, M. A. et al., Cell, 1995, 80:533–41) mutants, and immunological (Bar-Sagi, D., et al., J. Cell Physiol. Suppl., 1987, Suppl:69–73; Kolch, W. A, et al., Oncogene, 1996, 13:1305–14) or pharmacological inhibitors (Choudhury, G. G., et al., Am. J. Physiol., 1997, 273:F931–8; Kohl, N. E., et al., Science, 1993, 260:1934–7; Leftheris, K., et al., J. Med. Chem., 1996, 39:24–36). Furthermore, the analogy with yeast cyclase predicts sAC to be a direct effector of Ras.

To determine whether sAC transformed cells possess a defect in apoptosis, attempts can be made to block sAC transformation by expressing Bcl family members, which promote cell death (i.e., Bcl-$X_s$, Bax or Bad), or by activation of caspases (i.e., Betulinic Acid), which effect programmed cell death.

To determine whether sAC activity is required for other oncogenes to transform cells, signaling through sAC should be diminished or blocked. Using for example the ecdysone inducible expression system (Invitrogen) to regulate expression of antisense and dominant negative forms of sAC. Expression of antisense is a widely used technique which often selectively down-regulates protein levels of a target gene (Ho, P. T., et al., Semin. Oncol., 1997, 24:187–202). Down-regulation of sAC protein in NIH 3T3 may be possible because (1) there do not seem to be any closely related genes in mammals; (2) sAC mRNA levels are low in somatic tissues; and (3) co-transfection of sAC antisense (αsAC) diminished activity of the inducible sAC expression construct. Inducible αsAC can be stably introduced in the EcR/RXR expressing NIH 3T3 cells, and Western Blotting used to reveal the time course of antisense induction required to diminish endogenous sAC protein levels.

Oncogenic Activity of sAC

Another aspect would be to use sAC to test whether other known oncogenes require sAC activity to transform cells. Individual oncogenes are transiently transfected into inducible sAC antisense or dominant negative cell lines to see whether sAC down-regulation (i.e., in the presence of the inducing agent, ponasterone A) hinders the tested oncogene's ability to transform NIH 3T3 cells. A variety of representative oncogenes including, but not limited to, src, myc, jun, bcl2, sis, erbA, erbB, crk, and dominant negative forms of tumor suppressors, such as Rb and p53, can be tested.

For example, the 120 kD sAC isoform of sAC is specifically upregulated in human tumors (FIG. 5). This processed molecule contains the potential Leucine Zipper motif identified at approximately 115 kD from the N-terminus. If this Leucine Zipper is functionally important to the 120 kD isoform, then specific inactivation of this isoform may be possible by introducing peptide mimics of its sequence, or a protein fragment which encompasses this sequence. In this way, the 120 kD isoform of sAC can be selectively inhibited without affecting the activity of the 48 kD or other isoforms.

Pharmacologic inhibition of tyrosine and serine/threonine kinases (i.e., herbimycin A or genistein and staurosporine or H-9) and phosphatases (i.e., Benzylphosphonic acid-(AM)$_2$ and okadaic acid or microcystin), and antioxidants (i.e., CAPE), implicated in cellular transformation, represent candidate pathways for evaluation. Dose-response relationships will be determined for inhibitors which block sAC transformation. Individual components from biochemical pathways corresponding to any successful inhibitors can be evaluated.

sAC as a Bicarbonate Chemosensor

Multiple mammalian physiological processes are mediated by $CO_2$/bicarbonate via as yet uncharacterized chemoreceptors. Applicants have found that sAC is directly controlled by bicarbonate/$CO_2$ levels and therefore sAC may be a physiological chemoreceptor in processes mediated by $CO_2$/bicarbonate. Immunoprecipitated sAC activity was stimulated by bicarbonate in the presence of the physiologically relevant substrate $Mg^{2+}$-ATP. These data suggest that sAC is responsible for bicarbonate stimulated cAMP accumulation in tissues such as testis and sperm, and that bicarbonate may be acting directly on sAC enzymatic activity. Because of the intimate relationship between bicarbonate, $CO_2$ and pH, it is possible that some, if not all, of these signaling processes in physiological systems, including but not limited to those described below, are regulated by bicarbonate modulation of cAMP.

Evolutionary precedence for such a signal transducing pathway can be found in cyanobacteria. Using purified recombinant enzyme, applicants have demonstrated that the same adenylyl cyclase which senses light, cyaC, is directly stimulated by bicarbonate. It is believed that this cyanobacterial adenylyl cyclase may be a cellular $CO_2$/bicarbonate sensor, producing cAMP in direct response to $CO_2$/bicarbonate to stimulate metabolism.

Physiological Processes Regulated by Bicarbonate/carbon Dioxide

Ciliary processes of the eye. Aqueous humor formation by ocular ciliary processes is dependent on bicarbonate (Kishida et al., 1982; Maren, 1972). Carbonic anhydrase inhibitors, which affect the balance between $CO_2$, pH, and bicarbonate ions, can be used to treat glaucoma by decreasing aqueous humor secretion. However, the regulation and mechanism of bicarbonate-dependent secretion are not well understood. There is an established link between ocular aqueous flow and cAMP signal transduction (Caprioli and Sears, Lancet, 1983, 1:958), but how adenylyl cyclase, the enzyme synthesizing cAMP, is regulated remains unclear. Bicarbonate-stimulated adenylyl cyclase activity has been found in ciliary processes (Mittag et al. 1993) suggesting that a distinct form of mammalian adenylyl cyclase may be present in these secretory epithelia which may provide the link between bicarbonate, cAMP signaling, and aqueous humor formation., i.e. bicarbonate-dependent increase in cAMP signaling leading to aqueous humor formation. Based on the discovery by applicants that sAC is stimulated by bicarbonate, it is believed that sAC may be the bicarbonate sensing receptor mediating changes in cAMP metabolism and may affect fluid secretion in secretory epithelia. Thus sAC may be a target for alternate therapy or treatment for glaucoma. Accordingly, the present invention provides a method of treating glaucoma by reducing aqueous humor formation stimulated by cAMP signaling by administering to a subject afflicted with glaucoma a modulator of sAC activity in an amount effective to reduce or inhibit sAC activity to decrease the production of cAMP. It is contemplated that administration of a sAC activity modulator or inhibitor can be effected through methods known to those of skill in the art for treating glaucoma or other eye conditions, such as in eye drops, in suspension, emulsion and the like, and may be administered daily, however the timing of administrations or applications will take into account the severity of the condition, the age of the subject, etc. The sAC modulator or inhibitor may be used optionally in conjunction with one or more of a variety of agents suitable for the preparation of different formulations which will be selected in accordance with the type of formulation and route of administration desired. Included are buffers salts, preservatives, and the like, and optionally may further include other biologically active agents.

Choroid plexus of the brain Cerebrospinal fluid formation by the choroid plexus is also dependent on bicarbonate (Maren, Am.J.Physiol., 1972, 222:885–899). In choroid plexus transport systems, carbonic anhydrase inhibitors decrease fluid secretion (Maren, Annu. Rev. Physiol., 1988, 50:695–717). Others have reported the existence of a bicarbonate-stimulated adenylyl cyclase activity in the choroid plexus, but not in the cerebral cortex (Mittag et al., 1993). sAC may be the bicarbonate sensing receptor mediating changes in cAMP metabolism and may affect fluid secretion in secretory epithelia. Accordingly, sAC may be a target for therapy or treatment of conditions such as hydrocephaly by using inhibitors of sAC activity.

Breathing. Partial $CO_2$ pressure ($P_{CO2}$) is a critical value in determining the rate of ventilation (Johnson, 1998). An increase of $P_{CO2}$ increases breathing frequency, and a decrease of $P_{CO2}$ decreases breathing frequency. These rate changes are mediated by peripheral and central chemoreceptors which monitor changes in arterial blood gases.

Peripheral arterial chemoreceptors sense changes in $P_{O2}$ and $P_{CO2}$ in the carotid and aortic bodies, and they detect alterations in pH in the carotid bodies. The central chemoreceptive area at the ventral surface of the medulla senses changes only in arterial $P_{CO2}$. The molecular nature of each of these types of chemoreceptors is unknown. Based on the discovery by applicants that sAC is stimulated by bicarbonate, it is possible that sAC may function as the bicarbonate chemoreceptor.

The present invention provides a method for altering breathing rate or frequency by providing sAC as a target for drug or other therapeutic agents to modulate sAC activity. Agents which modify sAC's ability to sense bicarbonate make it possible to alter the equilibrium between $CO_2$/bicarbonate. In this manner, in situations where oxygen absorption is compromised, e.g., high altitude, stress, marathon running, athletic training, breathing rate or frequency may be advantageously facilitated and physical activity sustained.

Bloodflow. Blood flow is tightly coupled to tissue metabolism (Johnson, 1998). Carbon dioxide, protons, and adenosine relax smooth muscle and act as vasodilators. For example, cerebral arterioles dilate in response to increases in metabolic activity of the brain. Cerebral arterioles are exquisitely sensitive to the vasodilatory action of $P_{CO2}$ However, the molecular nature of the vascular $P_{CO2}$ receptor is unknown. sAC may be the $CO_2$ sensor mediating this vasodilatory response to metabolism.

Bicarbonate Regulation by the Kidney

Serum bicarbonate concentration is tightly regulated by the kidney to be 22–26 mM. The kidney reabsorbs all bicarbonate filtered at the glomerulus and generates new bicarbonate by excreting 'titratable acidity' ($H^+$ combined with urine buffers such as $HPO_4^{2-}$ and $SO_4^{2-}$) and ammonium ions. The proximal tubules "reabsorb" 95% of the filtered bicarbonate (Johnson, 1998). Dependent on the body's acid-base balance, the distal convoluted tubules and the collecting ducts can absorb or secrete bicarbonate (Johnson, 1998); however, it is unknown how the kidney senses serum bicarbonate concentration to determine which is appropriate. A bicarbonate-stimulated adenylyl cyclase activity was reported in kidney medulla and cortex (Mittag et al., 1993). Based on the discovery by applicants that sAC is stimulated by bicarbonate, it is possible that sAC may function as a renal bicarbonate sensor.

Accordingly, the present invention provides a means of modulating serum bicarbonate concentration by modulating sAC activity, as described herein, in the kidney, thereby altering the kidney's mechanism for bicarbonate regulation.

Biosensors

The discovery that bicarbonate stimulates sAC activity also provides a means for detecting and quantifying bicarbonate in a body fluid using sAC as a sensor. The monitoring of physiological bicarbonate levels is applicable in emergency situations, intensive care, during surgery neonatal care where monitoring of the blood gases is critical to avoid excessive or subnormal levels of carbon dioxide or bicarbonate resulting in metabolic or respiratory acidosis or alkalosis. Blood gas level measurements can be used in non-emergency situations to monitor the ratio of $CO_2$/bicarbonate in order to manipulate the ratio to alter breathing rate and frequency, for example for high altitude sickness, marathon runners, and endurance athletes.

Devices which measure blood chemistry (pH, $CO_2$, $PO_2$) are well known in the art. Current methods generally used in biosensor technology include a variety of combinations of biological elements and transducing elements such as calorimetric, optical, potentiometric and the like (Biosensors Turner Oxford University Press, New York 1987).

sAC may be used as a sensor in its capacity as an enzyme to determine physiological bicarbonate levels. These methods include utilizing reporter genes, such as galactosidase, described above, or immunological detection. sAC stimulation by bicarbonate can be detected using the methods described above for determining sAC activation.

Alternatively, since in the presence of bicarbonate sAC is activated and cAMP is generated, the invention also includes quantifying bicarbonate levels by directly detecting cAMP production. The amount of cAMP detected is directly correlatable to the amount of bicarbonate in the sample. Methods for measuring cAMP production are well known to those of skill in the art. A system for detection that can be used in conjunction with sAC as a sensor molecule suitable for the present invention includes one based on the occurrence of an enzymatic reaction, detected by energy transfer, wherein the reaction is dependent on the presence of cAMP (see, e.g., U.S. Pat. No. 5,439,797).

sAC as a Regulator of Male Fertility

Sperm functions thought to be mediated by cAMP include sperm maturation, mobility and the acrosome reaction. Less clear is the molecular basis of sperm capacitation, the series of events that provide sperm with the ability to fertilize an egg. $Ca^{2+}$ and $HCO_3^-$ are linked to the regulation of sperm cAMP concentration by their effect on the stimulation of adenylyl cyclase activity. (Visconti P. E. et al, Journal of Andrology, 1998, 19(2): 242–248). Based in part on the discovery that sAC activity is stimulated by treatment with bicarbonate, the present invention provides a mechanism for mediating sperm capacitation.

Thus the present invention provides a method of inhibiting fertilization of an ovum by inhibiting a soluble adenylyl cyclase activity in sperm. Soluble adenylyl cyclase activity can be inhibited, for example, by contacting sperm with a soluble adenylyl cyclase inhibitor, such that sAC activity is reduced or eliminated resulting in decreased or inhibited capacitation of sperm. It is contemplated that a sAC inhibitor could be provided in a formulation which will contact the sperm at various locations in the capacitation pathway.

Soluble adenylyl cyclase activity can also be regulated in order to facilitate or increase sperm capacitation. Facilitating sperm capacitation is particularly advantageous, for example, in the process of in vitro fertilization (IVF). IVF sperms are separated from seminal fluid and exposed to a proteinaceous cocktail which induces the capacitation reaction in the isolated spermatosa. By adding a factor that activates sAC, it is contemplated that the success of IVF may be improved in those instances which the sperm are in any way defective.

sAC as a Regulator of Insulin Secretion

Data indicate soluble adenylyl cyclase (sAC) may be regulated in vivo via changes in intracellular pH, therefore sAC may be involved in glucose regulation of insulin release from pancreatic islet cells. In islet cells, glucose regulated insulin release is a cAMP dependent process, but it is not known how glucose alters cAMP and the glucose sensor has not been identified. Glucose uptake is known to alter intracellular pH, but the connection to insulin release essentially ends there. sAC is regulated by bicarbonate and bicarbonate levels directly reflect intracellular pH, suggesting it could be the link between islet cells sensing glucose concentration and releasing insulin.

Polypeptide and Gene Therapy

The methods of the invention are useful in treating diseases characterized by a deficiency or an inappropriately high level of activity of cells. The invention provides methods of modulating the sAC signaling pathway.

Peptides may be administered to the patient intravenously in a pharmaceutically acceptable carrier such as physiological saline. Standard methods for intracellular delivery of peptides can be used, e.g. delivery via liposomes. Such methods are well know to those of ordinary skill in the art. The formulations of this invention are useful for parenteral administration, such as intravenous, subcutaneous, intramuscular, and intraperitoneal.

Therapeutic administration of a polypeptide intracellularly can also be accomplished using gene therapy, wherein a nucleic acid which includes a promoter operatively linked to a sequence encoding a heterologous polypeptide is used to generate high-level expression of the polypeptide in cells transfected with the nucleic acid. DNA or isolated nucleic acid encoding peptides of the invention may be introduced into cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. Pharmaceutically acceptable carriers are biologically compatible vehicles which are suitable for administration to an animal, e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule in the case of gene therapy.

Diagnostic Applications

The present invention encompasses compositions, methods, and kits useful in clinical settings for the qualitative or quantitative diagnosis of conditions arising from sAC activation. These applications typically utilize nucleic acids, peptides/polypeptides, or antibodies specific for sAC components. The methods may also be used to detect sAC specific cell lines and to detect sAC positive cells in a patient, in particular a human patient.

Antibody-based Diagnostic Methods

The invention provides methods for detecting sAC antigenic components in a biological sample, which methods comprise the steps of: (i) contacting a sample suspected to contain sAC antigenic component with an antibody specific for a sAC antigen, extracellular or intracellular, under conditions in which a stable antigen-antibody complex can form between the antibody and the antigenic components in the sample; and (ii) detecting any antigen-antibody complex formed in step (i) using any suitable means known in the art, wherein the detection of a complex indicates the presence of sAC antigenic components in the sample. It will be understood that assays that utilize antibodies directed against sequences previously unidentified, or previously unidentified as being sAC-specific, which sequences are disclosed herein, are within the scope of the invention.

Many immunoassay formats are known in the art, and the particular format used is determined by the desired application. An immunoassay may use, for example, a monoclonal antibody directed against a single sAC epitope, a combination of monoclonal antibodies directed against different epitopes of a single sAC antigenic component, monoclonal antibodies directed towards epitopes of different antigens, polyclonal antibodies directed towards the same antigen, or polyclonal antibodies directed towards different antigens. Protocols may also, for example, use solid supports, or may involve immunoprecipitation.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as for example, those that utilize biotin and avidin, and enzyme-labeled immunoassays, such as ELISA assays.

Kits suitable for antibody-based diagnostic applications typically include one or more of the following components:

(i) Anti-sAC antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Nucleic-Acid-Based Diagnostic Methods

The invention provides methods for detecting sAC-derived nucleic acids in a sample, such as a biological sample, which methods comprise the steps of: (i) contacting a sample suspected of containing sAC-derived nucleic acid with one or more sAC-derived nucleic acid probes under conditions in which hybrids can form between any of the probes and sAC nucleic acid in the sample; and (ii) detecting any hybrids formed in step (i) using any suitable means known in the art, wherein the detection of hybrids indicates the presence of sAC nucleic acid in the sample.

sAC-specific nucleic acids useful as probes in diagnostic methods include oligonucleotides at least about 8 nucleotides in length, preferably at least about 12 nucleotides in length, and most preferably at least about 15–20 nucleotides in length, that specifically hybridize the sAC gene.

A sample to be analyzed, such as for example, a biological sample or an environmental sample, may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without separation or used for PCR.

PCR based diagnostic kits are also contemplated and are encompassed by the invention.

Kits suitable for nucleic acid-based diagnostic applications typically include the following components:

(i) Probe DNA: The probe DNA may be pre-labeled; alternatively, the probe DNA may be unlabeled and the ingredients for labeling may be included in the kit in separate containers; and (ii) Hybridization reagents: The kit may also contain other suitably packaged reagents and materials needed for the

EXAMPLES

The present invention will be better understood by reference to the following examples, which illustrate embodiments of the invention but are not limiting.

Example 1

Purification, Molecular Cloning and Functional Expression of sAC

Materials and Methods

Cyclase Assay. In vitro adenylyl cyclase assay was performed as described previously (Levin, L. R. et al, Cell, 1992, 68:479–489; Levin L R et al., J. Biol., Chem., 1995, 270:7573–7579), except that the standard assay conditions for sAC activity included 5 mM $MnCl_2$ or $MgCl_2$ as indicated and contained 5 mM ($\alpha$-$^{32}$P) ATP (specific activity=about $4\times10^4$ cpm/nmol).

sAC Purification. sAC (approximately 3 μg) was purified from 950 rat testes by sequential column chromatography by using the following scheme (i) Frozen rat testes (950) (Pel-Freez Biologicals) (in batches consisting of 50 testes) were homogenized and sonicated in 20 mM Tris-HCl, pH 7.5, in the presence of DTT and proteinase inhibitors. After debris and nuclei were removed by low-speed centrifugation (3000×g for 10 min), a high-speed supernatant (>100,000×g for 60 min) was prepared. (ii) Total cytosolic protein (52 g) was dialyzed and separated (as 19 equal portions consisting of 50 testes each) over DE-52 cellulose anion exchange columns (Whatman; 80 ml bed volume; 20 mM Tris-HCl, pH 7.5) by using a linear NaCl gradient. All sAC activity bound and eluted as one peak between 0.15 to 0.2 M NaCl. (iii) sAC activity recovered from DE-52 (4 g protein divided into 11 aliquots 8 mls each) was separated by using an Ultrogel AcA54 gel filtration column (LKB; 4×100 cm/20 mM Tris-HCl, pH 7.5; flow rate 1.0 ml/min). Most sAC activity reproducibly eluted in a single peak with an apparent mass of 50–60 kDa. (iv) All sAC peak fractions from AcA54 gel filtration were pooled (1 g protein) and applied to a reactive Red 120-Agarose column (Sigma; 50 ml bed volume; 20 mM Tris-HCl, pH 7.5; linear gradient 0.1–1.0 M NaCl; f low rate 2 m/min; 600 ml total). Cyclase activity eluted between 0.45 and 0.55 M NaCl. (v) Active fractions (66 mg protein) were pooled, dialyzed, and applied to a Source Q anion exchange column (Pharmacia; 15 ml bed volume; 20 mM Tris-HCl, pH 7.5; linear gradient 0–0.3 M NaCl; flow rate 0.5 ml/min; 150 ml total). sAC activity eluted between 0.10 and 0.15 MNaCl. (vi) Active fractions (9 mg protein) were pooled, concentrated, and applied to a reactive Green 19-Agarose column (Sigma; 9 ml bed volume; 20 mM Tris-HCl, pH 7.5; linear gradient 0.1–1.0 M NaCl; flow rate 0.6 ml/min; 80 ml total). Cyclase activity eluted between 0.40 and 0.50 M NaCl. (vii) Active fractions (1.8 mg) were pooled, concentrated, and loaded onto a semipreparative HydroCell QA 1000 HPLC anion exchange column (Biochrom, Terre Haute, Ind.; 50×4.6 mm; 20 mM Tris-HCl, pH 7.4; linear gradient 0–0.3 M NaCl over 30 min; flow rate 2 ml/min). Cyclase activity eluted between 0.07 and 0.10 M NaCl. (viii) Active fractions (0.6 mg) were pooled and loaded onto an analytical QA 1,000 HPLC anion exchange column (HydroCell Biochrom; 150×2.3 mm; 20 mM Tris-HCl, pH 6.8; linear gradient 0–0.1 M NaCl over 25 min; flow rate 1.5 ml/min; 0.5 ml/fraction). Cyclase activity eluted between 0.04 and 0.06 M NaCl. (ix) Active protein fractions were separated on SDS/PAGE, stained with Coomassie Blue G-250, and the 48- and 62-kDa bands were excised. Protein sequence data were obtained at the Rockefeller University Protein/DNA Technology Centers (Fernandez J. et al. (1994) Anal. Biochem. 218: 112–117. Fernandez J. et al. (1992) Anal. Biochem. 201: 255–264) from approximately 3 μg of recovered 48-kDa protein. Table I provides protein and activity yields recovered during the purification procedure.

TABLE 1

Purification of sAC from 950 rats

| | | AC Activity | | |
|---|---|---|---|---|
| | Protein, mg | Total Units nmol/ min | Specific activity nmol/min/ mg × 100 | Fold enrichment |
| Cytosol | 51,900 | 2,400 | 4.6 | 1 |
| Preparative DE-52 | 4,015 | 3,000 | 75 | 16 |
| Gel filtration AcA54 | 1,074 | 2,100 | 200 | 43 |
| Reactive Red | 66 | 1,200 | 1,800 | 390 |
| Source Q | 8.8 | 1,100 | 12,500 | 2,700 |
| Reactive Green | 1.8 | 380 | 21,000 | 4,600 |
| Semipreparative QA, pH = 7.4 | 0.6 | 310 | 52,000 | 11,300 |
| Analytical QA, pH = 6.8 | | | | |
| Fraction #18 | 0.003 | 90 | 3,000,000 | 650,000 |
| Fraction #19 | 0.010 | 92 | 920,000 | 200,000 |

Protein concentrations determined by OD280. Units refer to nmol of cAMP formed per minute. Fold enrichment represents specific activity after each step compared to the starting specific activity.

Results. These results confirmed the presence of Mn $2^+$-dependent AC activity in cytosolic extracts from rat testis. The soluble enzymatic activity detected was unresponsive to either forskolin or the nonhydrolyzable GTP analogue, GTPγS, two general tmAC activators, and it displayed a Km for ATP of 1.2 mM in the presence of $MnCl_2$. sAC activity was purified using a combination of classical chromatographic methods shown in Table 1 and identified a 48-kDa candidate protein band by SDS-PAGE. The final chromatographic separation (step viii; analytical QA 1,000 HPLC) achieved greater than 60-fold enrichment (Table 1, fraction #18) even though it used the identical QA anion exchange matrix as the HPLC column preceding it (step vii; semipreparative QA 1,000 HPLC). By varying the buffer pH (pH=7.4 for the semipreparative QA vs. pH=6.8 for the analytical QA), sAC activity eluted before the majority of contaminating proteins during this final chromatographic separation. A silver-stained 12% SDS/PAGE gel of the active fractions from the final chromatographic step of the purification revealed two protein bands (of approximately 48 and 62 kDa) whose intensities coeluted with enzyme activity. During pilot purification studies, analytical gel filtration of partially purified cytosol predicted sAC to be 45–55 kDa, suggesting the more likely candidate was the 48-kDa protein. The limited amino acid sequence information obtained from the 62-kDa polypeptide revealed it was completely unrelated to the sAC gene.

Molecular Cloning. Fully degenerate oligonucleotide primers designed to recognize the amino acid sequences of peptides derived from the 48-kDa purified polypeptide (FIG. 1, double underlined) were synthesized for use in PCR amplification of rat testis first-strand cDNA. A 1-kilobase (kb) PCR fragment was generated that had a single ORF extending throughout its length and that contained sequences corresponding to all three peptides. This 1-kb PCR fragment was used as probe to screen a rat testis cDNA library constructed in our laboratory (λZap, Stratagene). Four overlapping cDNA clones were obtained from over 7.5×10⁵ oplaques. Among these, one represented a complete full-length cDNA clone. The nucleotide sequence of the fill-length cDNA was determined on both strands by dye termination-automated DNA sequencing (Cornell University DNA sequencing Core Facility, Ithaca, N.Y.) and confirmed by comparison to single-stranded sequence determined from at least one other independent cDNA clone. Sequence and database searching was performed on-line by means of BLAST (http:yywww.ncbi.nlm.nih.govyblasty) or PSORT II (http:yypsort.nibb.acjp:8800y).

Results. The sAC gene identified in rat, mouse, and human encodes a cytosolic form of adenylyl cyclase that is distinct from the previously characterized mammalian tmACs. Not only is sAC not a trans-membrane protein, but its catalytic domains are more closely related to the catalytic portions of bacterial ACs than they are to the catalytic domains of any other eukaryotic cyclase. In contrast, the mammalian tmACs, which are distantly related to these bacterial ACs and sAC, more closely resemble other invertebrate (Drosophila) and lower eukaryotic (Dictyostelium) Acs. The amino acid sequences of three tryptic peptides derived from the 48-kDa candidate polypeptide were not present in the databases of known proteins, indicating it represented a novel protein. The cDNA encoding this polypeptide was isolated by PCR followed by screening a rat testis cDNA library. All isolated cDNAs appeared to derive from one transcript whose nucleotide sequence revealed a single long ORF predicting a protein of 187 kDa (FIG. 1), which is significantly larger than the size (48 kDa) estimated by SDS/PAGE of the purified sAC protein. The peptides (SEQ ID NOS: 3–5) derived from the 48-kDa purified polypeptide reside completely within the amino terminal portion of the full-length protein, suggesting the purified polypeptide represents a proteolytically processed active form of the protein.

Comparison of this ORF with known protein sequences revealed two distinct regions of the putative sAC protein that display significant amino acid homology to various adenylyl cyclase catalytic domains (FIG. 1, bold type). Both sAC domains, C1 and C2, reside within its amino terminal 50 kDa and are therefore likely to be contained within the purified catalytically active processed form. The most closely related protein sequences in GenBank are the catalytic domains from a number of different cyanobacterial (*Anabaena spirulensis* cyaB1, cyaB2, and cyaA; and *Spirulina platensis* cyaC) and myxobacterial (*Stigmatella aurantiaca* cyaA and cyaB) adenylyl cyclases. These species have multiple AC genes with each isoform having a single catalytic domain. Interestingly, the catalytic domain of one AC isoform in each bacterial species is more similar to C1, whereas the catalytic domain of a second isoform from that species more closely resembles C2. This and the fact that C1 and C2 are not very similar to each other may suggest that during its evolution, mammalian sAC resulted from a fusion of distinct bacterial proteins rather than through duplication of a single catalytic domain.

There is also significant similarity between the two presumptive sAC catalytic domains and other AC catalytic domains. Alignment of C1 and C2 with the catalytic domains from related bacterial ACs, yeast ACs, Dictyostelium tmACs, and representative mammalian tmACs reveals that sAC C1 and C2 are more closely related to the catalytic portions of bacterial ACs than to the catalytic domains of any other cyclases. This similarity provides an evolutionary link between bacterial and mammalian signaling systems and suggests that the C1 and C2 catalytic domains in mammalian sAC are likely to have evolved independently from those in eukaryotic tmACs ($C1_a$ and $C2_a$).

The C-terminal portion beyond the AC homologous regions revealed no significant homology to any known protein in the databases, and the hydropathy profile of the full-length protein indicated no obvious potential transmembrane-spanning domains. Sequences that could represent a nucleotide-binding P Loop (FIG. 1, dotted underline) or that could form a leucine zipper interacting domain (FIG. 1, single underline) were detected within the region unrelated to the AC catalytic domains.

Hybridizations

Southern and Northern blots were probed with random-primed [$^{32}$P]dCTP-labeled 1-kb PCR-generated fragment 483–1536 under standard conditions. Southern blot was hybridized at 65° C. overnight and washed three times in 1×SSC (0.15M sodium chloride/0.015M sodium citrate, pH 7/0.1%SDS) for 15 minutes at 55° C. (low stringency) or three times in 0.5×SSC/0.1%SDS for 15 minutes at 65° C. (high stringency).

For Southern blots, 10 μg rat genomic DNA was digested with BamHI, EcoRI (E), HindIII (H), and XhoI (X) probed at high or low stringency by using the 1-kb PCR-generated sAC fragment containing both presumptive catalytic domains. Rat multiple tissue Northern blot (CLONTECH) representing approximately 2 μg poly-A⁺ RNA from testis (T), kidney (K), skeletal muscle (Sk), liver (Li), lung (Lu), spleen (S), brain (B), and heart (H) probed with 1-kb PCR-generated sAC fragment or with actin control. The sAC transcript is approximately 5.3 kb and, in most tissues, actin is approximately 2.0 kb.

Results Southern hybridization to rat genomic DNA, along with numerous database searches, indicated the presumptive sAC gene does not appear to be the progenitor of a gene family of sAC-like molecules in mammals. A sAC coding sequence probe 483–1536 hybridized at high and low stringency to parallel rat genomic Southern blots recognized identical genomic fragments, indicating the lack of closely related sequences in the genome.

sAC mRNA is most abundant in male germ cells, but it is widely expressed. Northern and RNA in situ analysis of expression in testis revealed high levels of sAC message exclusively in germ cells beginning in pachytene spermatocytes and accumulating to highest levels in round spermatids. This high level expression seems to reflect the previously determined biochemical restriction to testis, and suggests that sAC plays a prominent role in male reproductive physiology.

Additionally, we have identified the corresponding human and mouse sAC genes by database searches and reverse transcription-polymerase chain reaction (RT-PCR), respectively. The human sAC locus has been sequenced as part of the Genome Project. It is encoded by more than 30 exons that are spread across two overlapping P1-derived artificial chromosome (PAC) clones mapping to 1q24.

Using RT-PCR, sAC message can be readily detected in almost all tissues examined; RT-PCR products readily seen by ethidium bromide staining can be generated following thirty cycles of amplification from oligo-dT primed first strand cDNA using two sets of non-overlapping primers. The specificity of these PCR products was confirmed by Southern blotting. Its widespread expression, along with its conservation with bacterial signaling systems, suggest that sAC plays an additional, fundamental physiological role in all cells.

RT-PCR amplification of sAC revealed that it is widely expressed at low levels. Non-overlapping primer pairs used for RT-PCR of sAC cDNA amplified an 881 bp DNA fragment for primers 1 and 2 (SEQ ID NO: 6 CGAGCAGCTGGTGGAGATCC and SEQ ID NO: 7 GCGTGAGTGATCTCGTCAGGGGC), respectively, and a 748 bp DNA fragment for primer pairs 3 and 4 (SEQ ID NO: 8 CCTGCTTCTCCCTGCTGTG and SEQ ID NO: 9 GCAGGAGTAAAGTCCCAGG, respectively). Ethidium bromide stained agarose gel of RT-PCR products from brain, ovary, liver, lung, spleen, heart, embryo, thymus, testis.

Heterologous Expression. To confirm that the gene we isolated encoded an adenylyl cyclase, we heterologously expressed the full-length cDNA in HEK293 cells. The full-length and truncated sAC cDNAs were expressed from the library vector (pBK-CMV) under the control of the cytomegalovirus promoter after deletion of the intervening bacterial promoter sequences (as an NheI-SpeI fragment). The truncated sAC cDNA (sAC$_t$) represented a library clone that was missing an exon. The resultant protein shifted the reading frame after valine 469 (FIG. 1; underline), introducing two incorrect amino acids (serine and cysteine) followed by a stop codon. Expression constructs were transiently introduced into HEK293 by lipofectamine—mediated transfection (Life Technologies, Grand Island, N.Y.). One or two days after transfection, cells were harvested, resuspended in lysis buffer (50 mM Tris-HCl, pH 7.5/1 mM EDTA/1 mM DTT/0.1 mg/ml Leupeptin/1 mM phenylmethylsulfonyl fluoride) and disrupted by microtip probe sonication on ice. Whole-cell sonicates were ultramicrocentrifuged at >100,000×g for 10 minutes. Supernatants were cleared by a second centrifugation to yield 'cytosolic' extracts. Pellets were resuspended in lysis buffer by passage through a 27.5-gauge needle to generate 'particulate fraction.

Results Vector-transfected cells had no detectable soluble and very little unstimulated particulate AC activities. In contrast, cells transfected with the full-length sAC gene displayed substantial Mn 2+-dependent soluble AC activity (approximately 85 pmol cAMP/min/mg). Mn 2+-dependent activity was also elevated in the particulate fraction from transfected cell sonicates.

Because the sAC polypeptide purified from rat testis was approximately 48 kDa, we sought to determine whether the truncated version of sAC retained catalytic activity. The expression construct consisting of the amino terminal 53 kDa of sAC encompassing both presumptive catalytic domains was fully active, displaying an extremely high level of Mn 2+-dependent soluble AC activity (approximately 3500 pmol cAMP/min/mg). Therefore, the sAC purified from rat testis cytosol very likely represents a proteolytically processed form resembling this N-terminal truncation. The extremely high level of cytosolic activity in cells expressing the truncated form compared with those expressing the full-length protein is consistent with processing being required for catalytic activity; the activity in cells transfected with full-length sAC may be limited by the availability of activating enzymes.

We also examined whether heterologously expressed sAC responded to known stimulators of tmAC activity G protein and forskolin. When assayed in whole-cell sonicates from transfected HEK293 cells, which should contain the full complement of endogenous G proteins, both full-length and truncated forms of sAC were completely insensitive to forskolin and to the nonspecific G protein activator, GTPγS respectively.

The N-terminal 50 kDa of sAC is sufficient for enzymatic activity and approximately corresponds to the size of the protein purified from rat testis cytosol. Because all the cDNAs isolated from rat testis fell into a single class encoding the 187-kDa polypeptide, the 48-kDa purified protein should result from posttranslational cleavage. Truncating the sAC gene increased cyclase activity 10–20 fold in tissue culture cells, suggesting that the shorter molecule approximated an activated form. The activity directed in cells transfected with the full length cDNA may result from a cleaved molecule.

Production of anti-sAC Antisera We generated three anti-sAC antisera. An antiserum for the N-terminal peptide SARRQELQDRAIVK (SEQ ID NO: 10) was obtained. This peptide was produced as a MAP, or multigen antigenic peptide, by Research Genetics, Inc. and used to immunize rabbits.

The antigen for the N-terminal Catalytic Domain (αC1-C2) antisera is from the Methionine at position number 1 to the Valine at position #469. This antigen was used by HTI, Inc. to immunize rabbits.

The antigen for the C-Terminal (αC-Term) antisera is from the Isoleucine at position #1409 to the end of the protein coding sequence (Amino acid #1608). This antigen was used by HTI, Inc. to immunize chickens. We prepared rabbit antiserum against the first 15 N-terminal amino acids (αN-term), which are shared between mouse and rat; rabbit antiserum against the catalytic region (αC1-C2); and chicken antiserum against the C-terminus (αC-term). We constructed, expressed and purified two His-tagged fusion protein corresponding to the 50 kD rat N-terminus and the 20 kD rat C-terminus of sAC for use as immunogens. The generated antisera were affinity purified by negative selection against the shared His-tag and positive selection against the specific immunogen. We raised the αC-term antisera in chickens for use in double labeling studies together with rabbit anti N-terminal or catalytic antisera.

Figure 2:
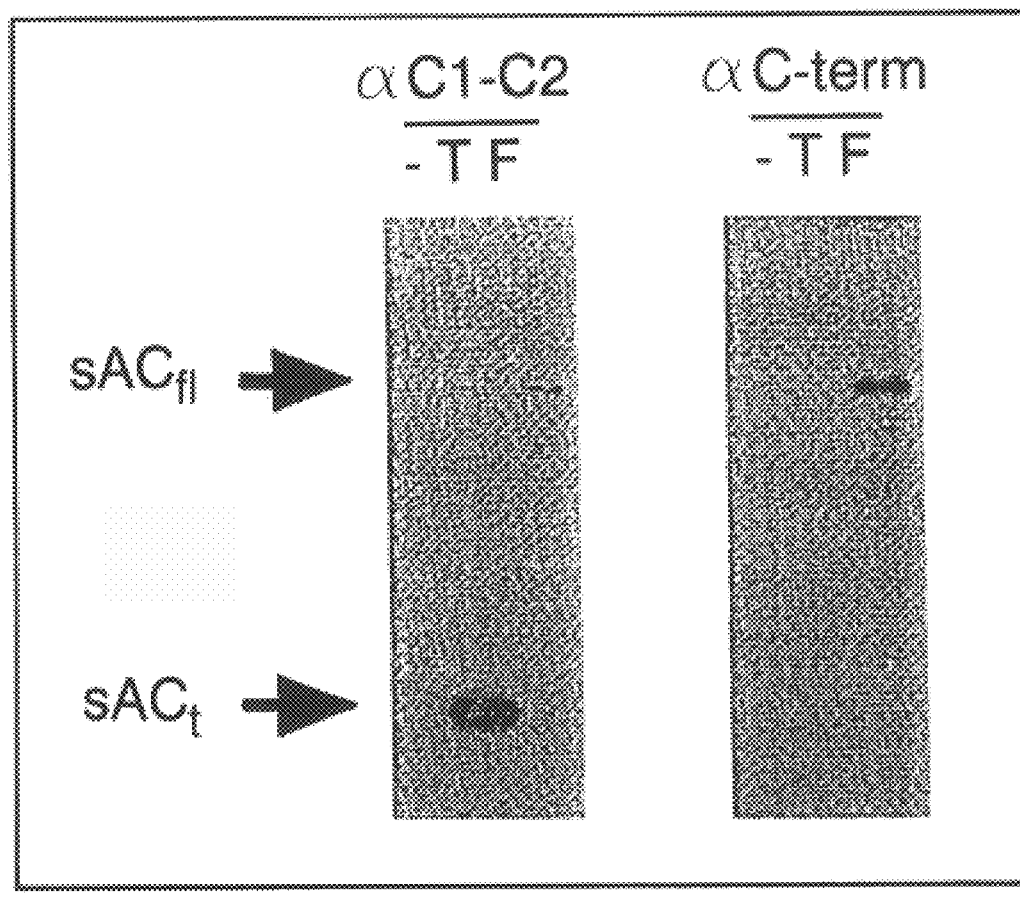
FIG. 2 shows that anti-sAC antisera specifically recognize heterologously expressed short and long forms of sAC. Whole cell lysates of HiFive cells infected with baculovirus vector (–), or with recombinant baculovirus expressing Truncated (T) or Full-length (F) sAC were separated on a 7.5% SDS/PAGE and Western blotted with the indicated crude antisera. "αC1-C2" and "αC-term" refer to affinity purified anti-catalytic (N-terminal ~50 kD) and anti-C terminal ~25 kD antisera, respectively. Detection was by enhanced chemiluminescence (Pierce); exposure times were all less than one minute.

The affinity purified sAC-specific antisera raised against either the catalytic N-terminal 50 kD (αC1-C2) (FIG. 2A), the C-terminal 25 kD (αC-term) (FIG. 2B), or the 14 N-terminal amino acids (αN-tern), recognize only sAC proteins in whole cell lysates of HiFive cells infected with recombinant baculovirus expressing Truncated (T) or Full-length (F) sAC. The sAC specific bands are not recognized by preimmune serum.

Immunoprecipitation of sAC Activity Supernatants from sAC$_t$ transfected HEK293 cells were incubated with (0, 0.3, 0.6, 1.2, 2.5 and 5 μl ) anti-sAC -terminal antibody and precipitated with 50 μl of Protein A beads (BIO-RAD). Immunoprecipitates were assayed using the soluble adenylyl cyclase assay. sAC transfected HEK293 cell supernatants also were incubated with 5 μl of anti-sAC -terminal antibody. Antibody-antigen complex was precipitated with 12.5, 25 or 50 μl of Protein A beads using standard methods. The αC1-C2 antisera (crude or affinity purified) immunoprecipitated heterologously expressed sAC activity.

sAC protein is processed into multiple isoforms Purified sAC activity from rat testis resided in a 48 kD polypeptide, yet the encoding cDNA predicted a 187 kD protein. Western analysis of mouse germ cells from different stages of spermatogenesis using the affinity purified sAC-specific antibody revealed the presence of multiple, developmentally regulated isoforms of sAC. Using purified preparations of mouse primary spermatocytes (pre-meiotic germ cells), round spermatids (post-meiotic germ cells undergoing spermiogenesis or differentiation into mature spermatozoa), and epididymal sperm (spermatozoa maturing as they transit through the epididymis), we detected five distinct immunoreactive bands, of 190 kD, 150 kD, 120 kD, 48 kD, and 45 kD (Table 2).

TABLE 2

Immunoreactive bands recognized by sAC specific antisera

| Protein bands | αN-term | αCatalytic (C1-C2) | αC-term |
|---|---|---|---|
| 190 kD | + | + | + |
| 150 kD triplet | − | + | − |
| 120 kD | − | + | − |
| 48 kD | − | + | − |
| 45 kD | + | + | − |

Figure 3:
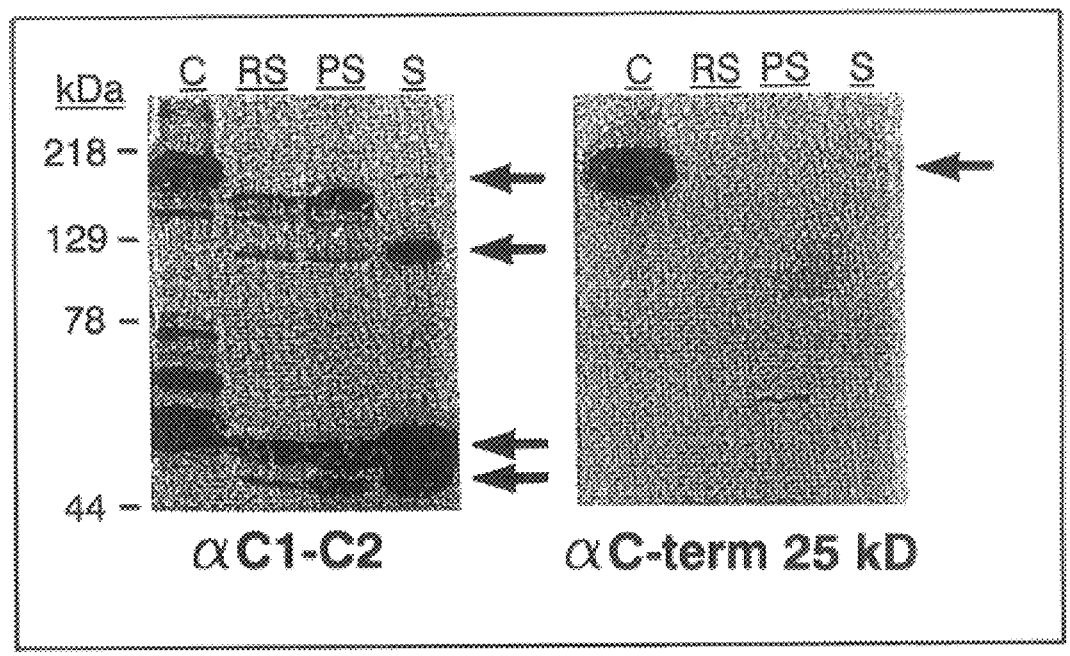
FIG. 3 shows multiple sAC isoforms in staged germ cell preparation. Whole cell lysates of the indicated enriched germ cell populations were separated on a 7.5% SDS/PAGE and Western blotted with the affinity purified antisera: C=control samples representing a mixture of extracts from Hi5 cells infected with truncated (50 kD) and full-length expressing baculovirus, partially degraded; RS=round spermatids; PS=pachytene spermatocytes; and S=spermatozoa. Arrows point out $sAC_{fl}$, 120 kD, 48 kD, and 45 kD isoforms. Immunoreactive bands were detected by enhanced chemiluminescence (Pierce); exposure times were less than one minute.

All bands were recognized by the anti C1-C2 antiserum. The 190 kD species corresponds to full-length, native sAC protein; it is recognized by all three sAC-specific antisera. As there are no alternatively spliced transcripts from the sAC gene, we assume that the remaining bands correspond to post-translationally processed isoforms. The 45 kD form is additionally recognized by αN-terminal antiserum. The 48 kD form corresponds to the sAC activity we purified. The 120 kD species is only recognized by the anti C1-C2 antiserum. While both the 48 kD and the 45 kD isoform do not appear to vary during spermatogenesis, the 120 kD sAC isoform seems to be developmentally regulated. We believe this isoform is specifically generated during final sperm maturation. Interestingly, because of its size and the fact that it is recognized by αC1-C2 but not by αC-term, this isoform would include both the potential nucleotide-binding P loop at 55 kD and the leucine zipper interacting domain at 115 kD. Additionally, there is a triplet of specific protein bands at approximately 150 kD detected only in pachytene spermatocytes (PS) and round spermatids (RS) which could correspond to distinct proteolytic processing intermediates. FIG. 3 is a photograph of the Western blot.

Example 2 sAC in Bicarbonate Sensing Tissues

Experiments were performed to determine whether native sAC was present in tissues known to regulate bicarbonate concentrations and have been found to contain bicarbonate stimulated adenylyl cyclase activity.

Figure 4A:
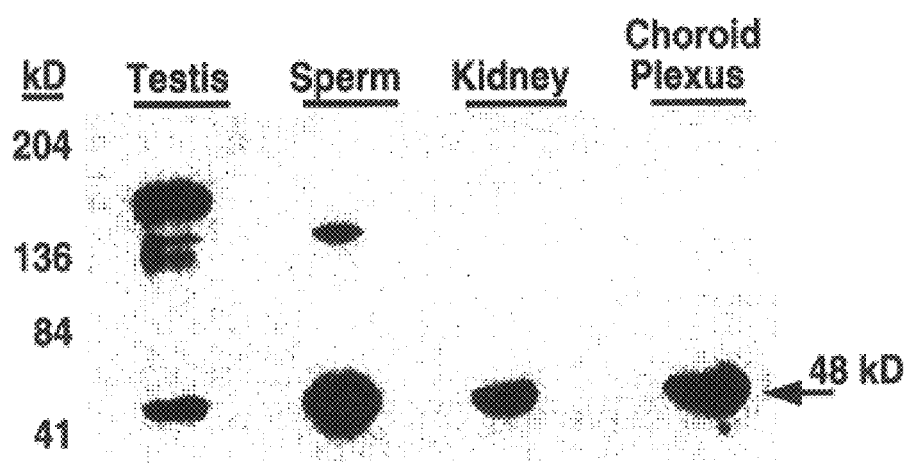
FIGS. 4a and b show that sAC is detected in a number of bicarbonate sensing tissues.

Samples of testis, sperm, kidney, and choroid plexus were tested against anti-sAC antibody in a Western blot, shown in FIG. 4a. The lanes contained the following amount of sample: testis (30 μg), sperm (5 μg), kidney (50 μg), and choroid plexus (50 μg). sAC was detected in all these tissues.

Figure 4B:
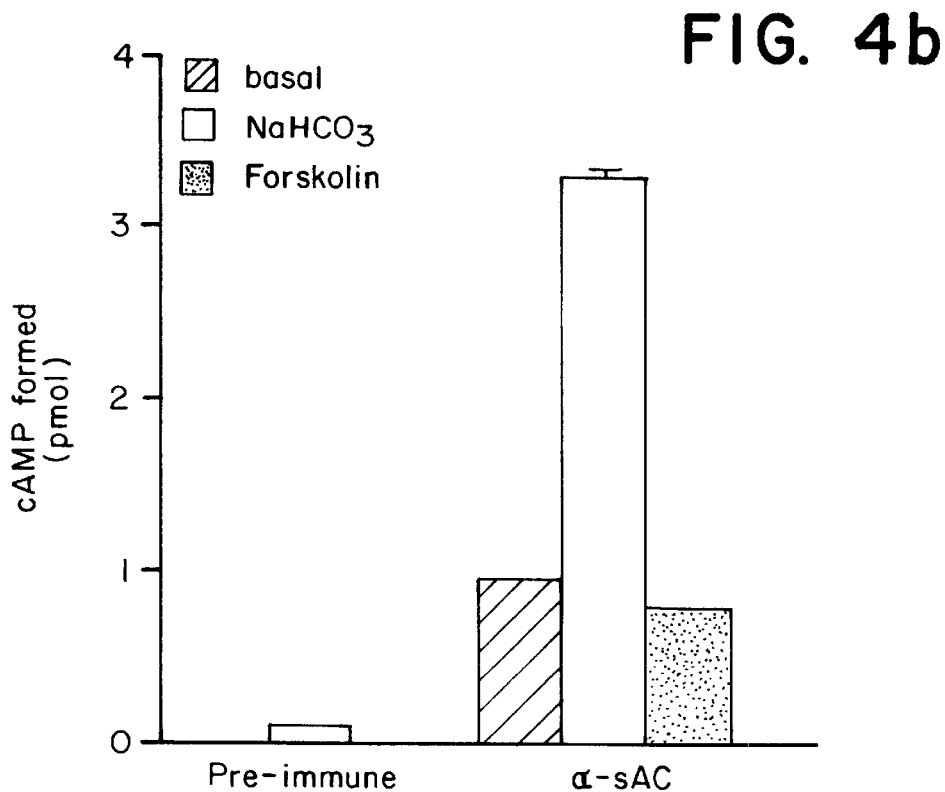
FIG. 4b-Adenylyl cyclase activity in immunoprecipitates from testis cytosol using either pre-immune serum or (α-sAC antisera).

Rat testis were tested for sAC activity by immunoassay. Immunoprecipitates from rat testis cytosol were tested using either pre-immune serum or α-sAC antisera. Activity was measured by radioimmunoassay (Amersham) in the absence of any additions (striped bar), or in the presence of 40 mM NaHCO$_3$ or 100 μM Forskolin. The results are shown in FIG. 4b. This antisera specifically immunoprecipitated a bicarbonate stimulated AC activity from the cytosol of rat testis (FIG. 4b). The results also demonstrated that the immunoprecipitated activity was not forskolin responsive, and was therefore unlikely to be caused by cross-reacting tmACs in the immunoprecipitate. Data in FIG. 4b are presented as pmol of cAMP formed over 20 minutes, and values represent averages of duplicate determinations with standard deviations indicated.

sAC activity is stimulated by bicarbonate. To examine the effect of bicarbonate on sAC catalytic activity, we constructed a stable HEK293 cell line expressing the full-length (sAC$_{fl}$) CDNA (HEK293/sAC$_{fl}$) and a cell line transfected with vector. The cell lines were starved for bicarbonate (grown in HEPES-bufferred, NaHCO$_3$-free D-MEM under ambient CO$_2$) for 24 hours. Cellular cAMP accumulation and in vitro adenylyl cyclase activity in the presence of [a$^{32}$P] ATP and MnCl$_2$ or MgCl$_2$ were assayed. In vitro adenylyl cyclase assays were performed at pH 7.5 in Tris-buffered solutions.

Figure 5A:
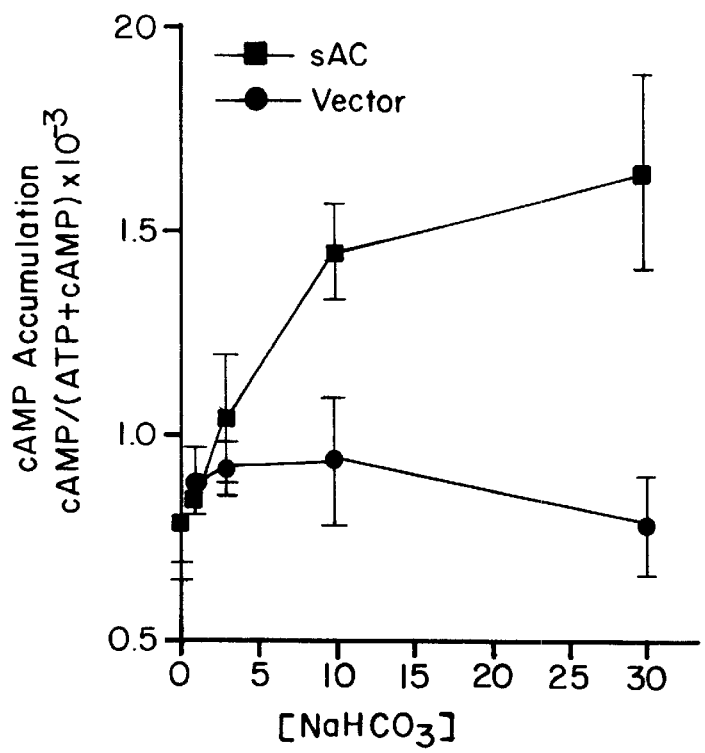
FIGS. 5a and b show that sAC is stimulated by bicarbonate.
Figure 5B:
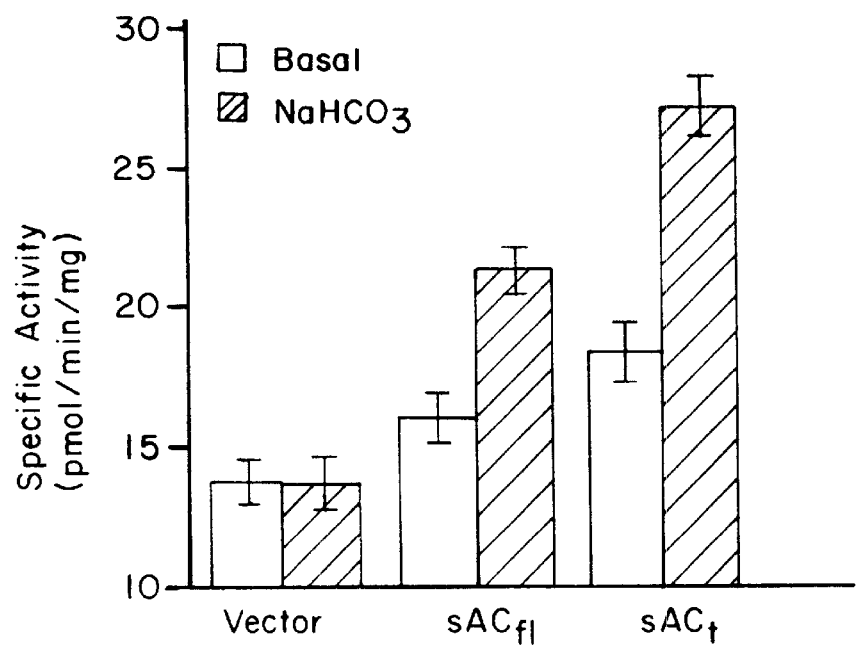
FIG. 5b-In vitro cyclase activity in extracts from stable cell lines expressing empty expression vector, $sAC_{fl}$, or $sAC_t$ in the presence (dark bars) or absence (light bars) of 50 mM $NaHCO_3$. Data are expressed as pmol of cAMP formed per minute per mg total protein, and values represent averages of triplicate determinations with standard deviations indicated.

Addition of NaHCO$_3$ to the extracellular medium stimulated cAMP accumulation in HEK293/sAC$_{fl}$ but not in vector transfected HEK293 cells (HEK293/V)(FIG. 5a). Bicarbonate increased cAMP production at the earliest time points tested, but accumulation was complete by 10 minutes. These data demonstrated that sAC can be activated by bicarbonate in the absence of any additional testis or sperm specific factors.

To delineate the regions of sAC that mediate bicarbonate activation, we constructed an additional stable cell line (HEK293/sAC) expressing a catalytically active, N-terminal truncation (sAC) consisting almost exclusively of the two catalytic domains which approximates the native 48 kDa sAC species. Bicarbonate also stimulated cAMP accumulation in HEK293/sAC$_t$ revealing that bicarbonate stimulation of sAC activity did not require the large C terminal domain. Bicarbonate also activated heterologously expressed sAC in vitro. Adenylyl cyclase activity was stimulated in cellular lysates from HEK293/sAC$_{fl}$ and from HEK293/sAC$_t$ cells (FIG. 5b), further indicating that the enzyme is directly modulated by bicarbonate ions.

Figure 6B:
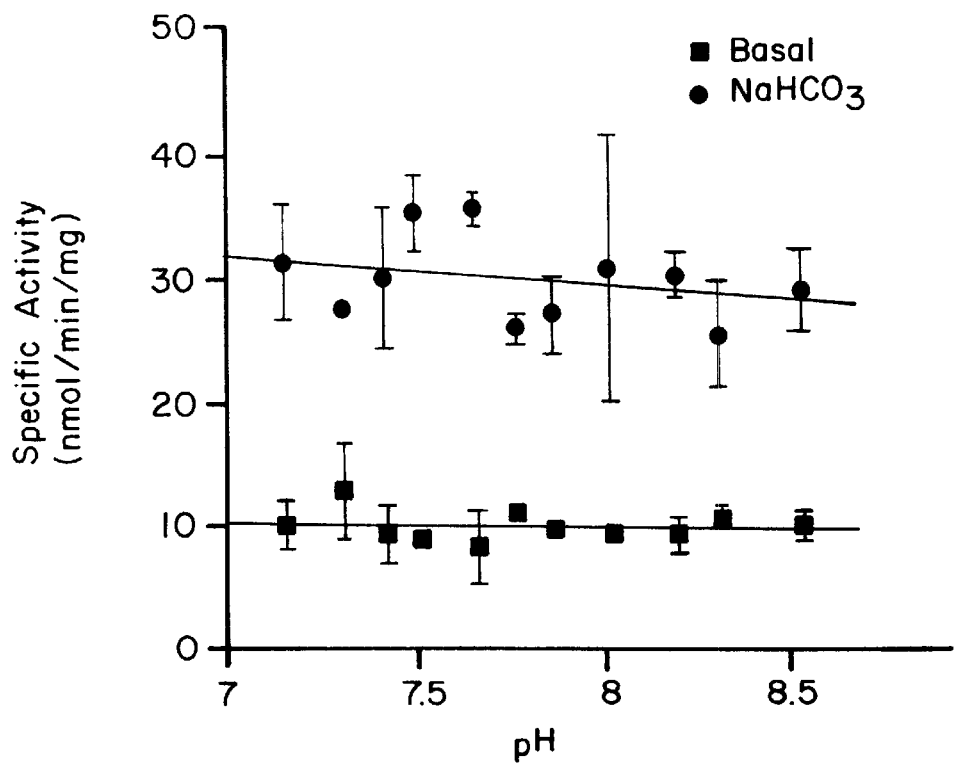
FIG. 6b-Purified $sAC_t$ was assayed at the indicated final pHs (buffered by Tris-HCl) in the presence (circles) or absence (squares) of 40 mM $NaHCO_3$. Best fit lines were generated using linear regression analysis.
Figure 6A:
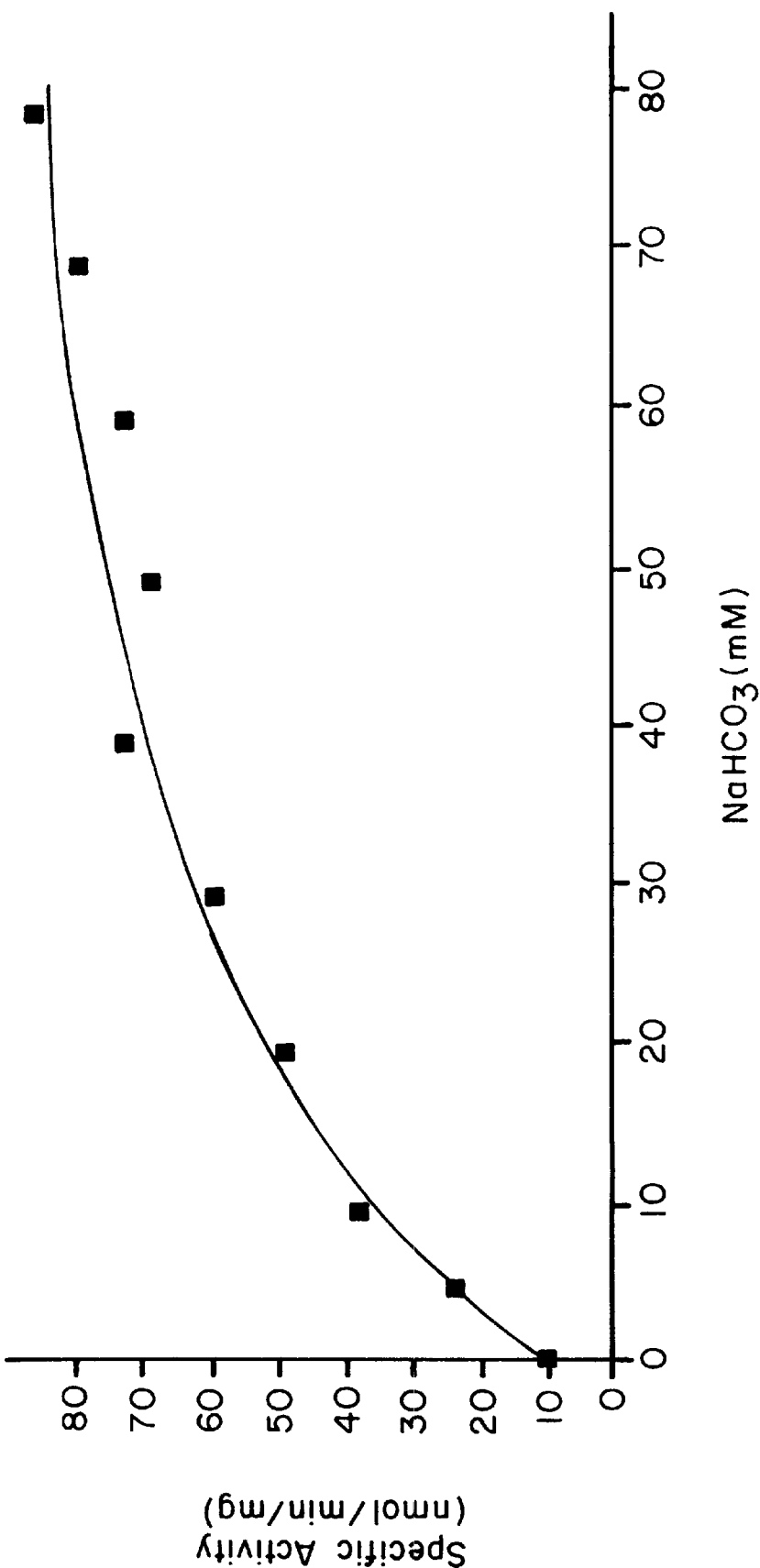
FIGS. 6a, b, and c show that bicarbonate activation of sAC is direct, specific, and pH independent.

Bicarbonate activation of sAC is direct, specific, and pH independent. Experiments were performed to demonstrate that bicarbonate acted directly on sAC and to exclude the possibility of accessory factors mediating activation in preparations using testis and stable cell lines. Purified recombinant sAC$_t$ protein (sAC$_t$, amino acids 1–469, plus a C-terminal Hexahistidine tag was heterologously expressed in insect HiFive cells using the Bac-to-Bac Baculovirus Expression System (Life Technologies), and protein was purified by chromatography over Ni$^{2+}$-NTA Sepharose Resin (Qiagen)) was assayed in the presence of 0–80 mM NaHCO$_3$ with 10 mM ATP and 40 mM MgCl$_2$. Purified enzyme was stimulated greater than seven-fold (FIG. 6a) with an EC$_{50}$ (25.4±7.6 mM) within the physiologically relevant bicarbonate concentration in mammalian serum (22–26 mM) (Pitts, R. F., Physiology of the Kidney and Body Fluids (Year Book Medical Publishers, Inc., Chicago, ed., 3rd, 1974; Johnson, 1998). Kinetic parameters were determined using KinetAsyst II (IntelliKinetics). These results suggest that direct activation of sAC accounts for the observed intracellular increase in cAMP generation in sACexpressing cell lines (shown in FIG. 5a).

Purified sAC$_t$ was also assayed as above at pHs 7–8.5 (final pH) (buffered by Tris-HCl) in the presence or absence of 40 mM NaHCO$_3$. The results shown in FIG. 6b demonstrated that bicarbonate stimulation was not due to altered pH because both MG$^{2+}$-ATP alone and bicarbonate-stimulated sAC activities were completely insensitive to pH changes over the pH range 7.0–8.5.

Among mammalian adenylyl cyclases, sAC appears to be the only form regulated by bicarbonate ions. HEK293/V cells, which express endogenous tmACs, were unaffected by bicarbonate addition (see FIG. 5). Even when submaximally stimulated by forskolin, tmAC activity was insensitive to bicarbonate. Engineered soluble tmACV was constructed and purified as described (Scholich, K et al., Proc. Natl.

Acad. Sci. USA, 1997, 94:2915) and assayed in the presence of $MgCl_2$ alone (basal), or with 50 mM $NaHCO_3$, or 100 μM Forskolin.

Figure 6C:
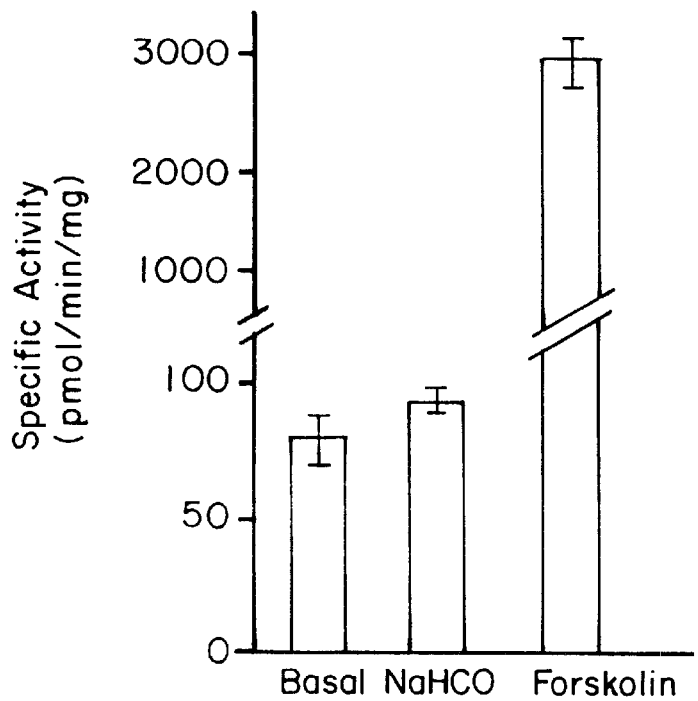
FIG. 6c-Purified recombinant soluble tmACV was assayed in the presence of $MgCl_2$ alone (basal), or with 50 mM $NaHCO_3$, or 100 μM Forskolin. Data are presented as pmol cAMP formed per minute per mg protein, and values represent triplicate determinations with standard deviations indicated.

Data are presented in FIG. 6c as pmol cAMP formed per minute per mg protein, and values represent triplicate determinations with standard deviations indicated. Results demonstrated that while a purified engineered soluble form of tmAC Type V was fully responsive to forskolin, it was completely insensitive to bicarbonate addition. Therefore, bicarbonate stimulation is not a general feature of all ACs, and mammalian cells possess two independently regulated cAMP signal transduction systems.

Activation of sAC by various salts. sAC activity was stimulated equally well by $NaHCO_3$ or $KHCO_3$. The stimulatory effects of $NaHCO_3$ were successfully produced using bisulfite ion ($Na_2SO_3$ or $NaHSO_3$), which structurally resembles bicarbonate, but not with dissimilar ions, such as chloride (NaCl), sulfate ($Na_2SO_4$), or phosphate ($Na_2HPO_4$). The results are shown in Table 1.

TABLE 1

Activation of sAC by various salts.

| Salt[1] | % Basal[2] |
| --- | --- |
| $NaHSO_3$ | 138 ± 4.6 |
| $Na_2SO_3$ | 164 ± 2.9 |
| NaCl | 93 ± 11.8 |
| $Na_2HPO_4$ | 75 ± 2.6 |
| $Na_2SO_4$ | 66 ± 4.6 |
| $NaHCO_3$ | 411 ± 5.3 |
| $KHCO_3$ | 412 ± 6.1 |

[1]Salts were used at 50 mM.
[2]Adenylyl cyclase activity shown relative to activity in the absence of any salts.

These data exclude $Na^+$ ion and simple alterations of ionic strength as regulators of sAC activity, and they indicate that bicarbonate, as opposed to $CO_2$, directly binds to and activates sAC in a pH independent manner. However, because carbon dioxide is in equilibrium with bicarbonate, sAC and the cAMP signaling pathway may also indirectly monitor in vivo levels of carbon dioxide.

Figure 7B:
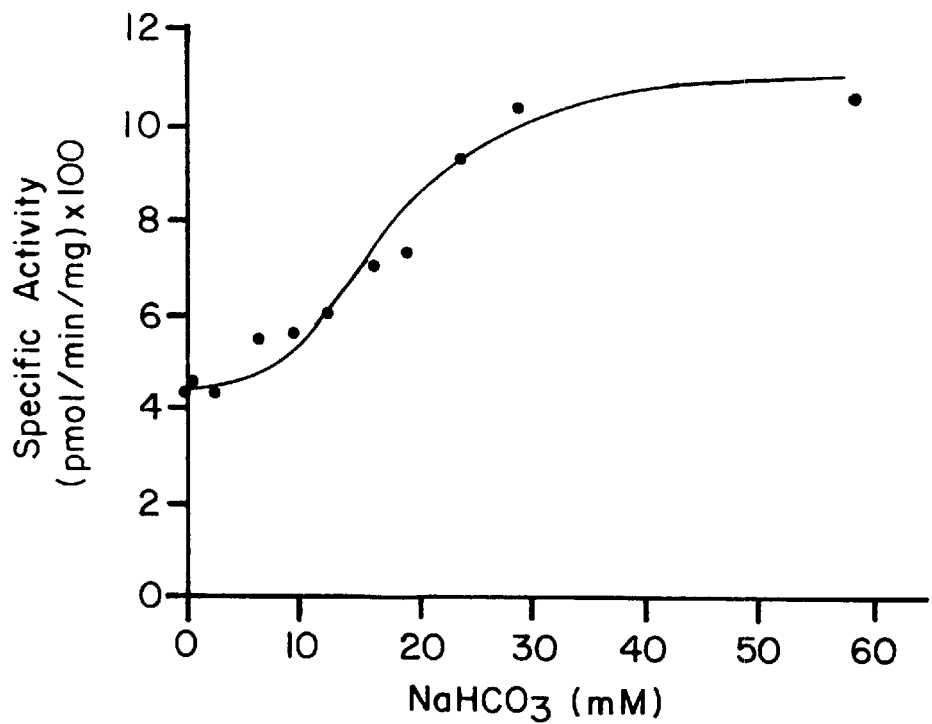
FIG. 7b-Expressed and purified *Spirulina*
Figure 7A:
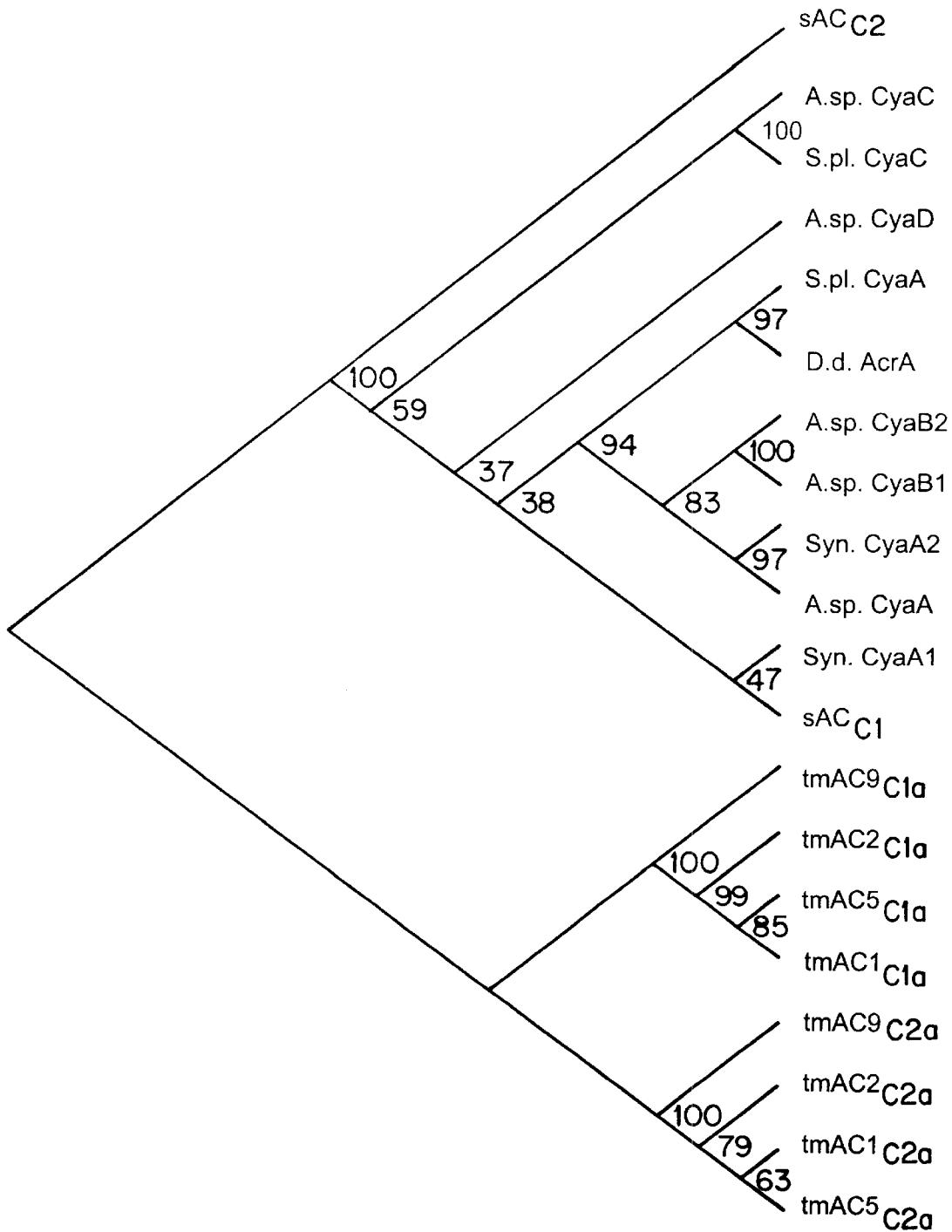
FIGS. 7a and b show the relationship between sACs and that bicarbonate activates cyanobacterial adenylyl cyclase.
Figure 8A:
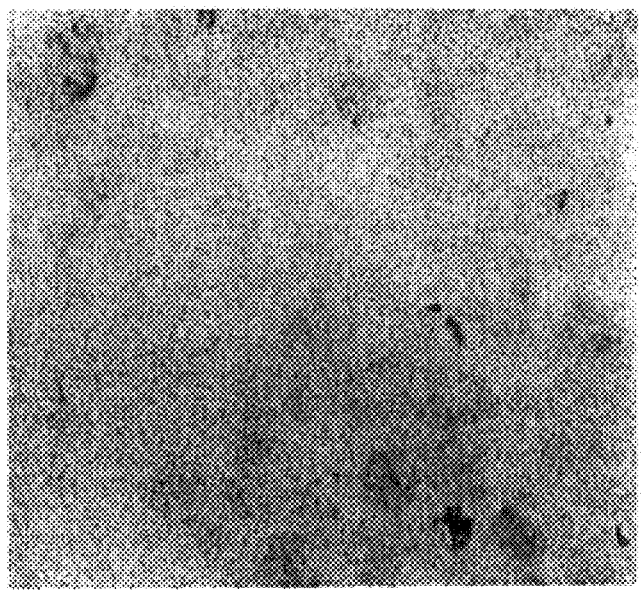
Figure 8B:
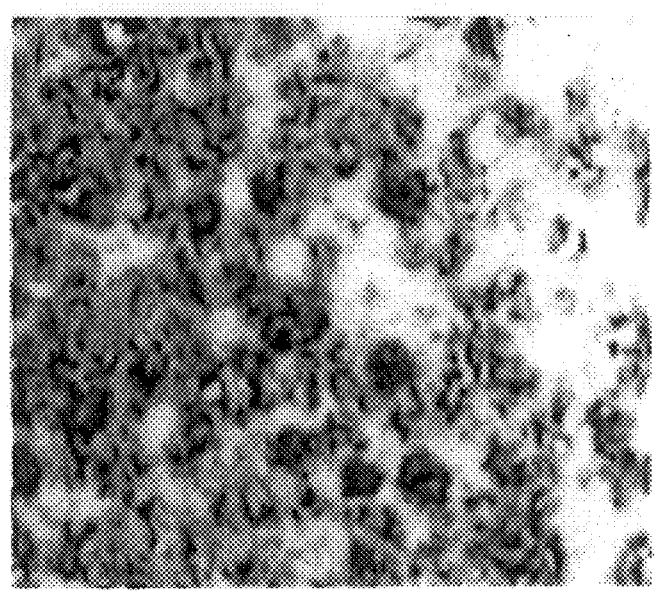
Figure 8C:
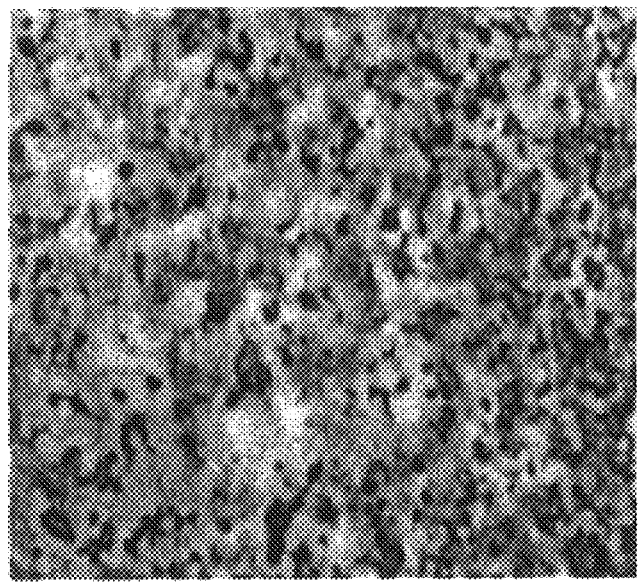
Figure 8D:
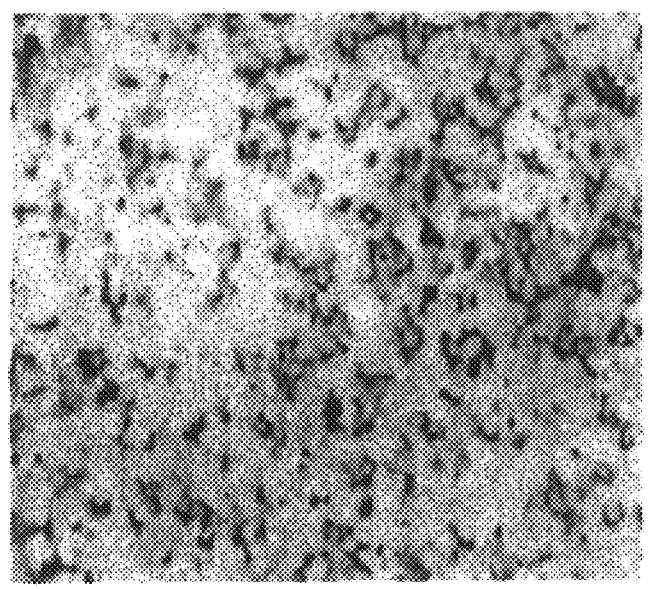
Figure 8E:
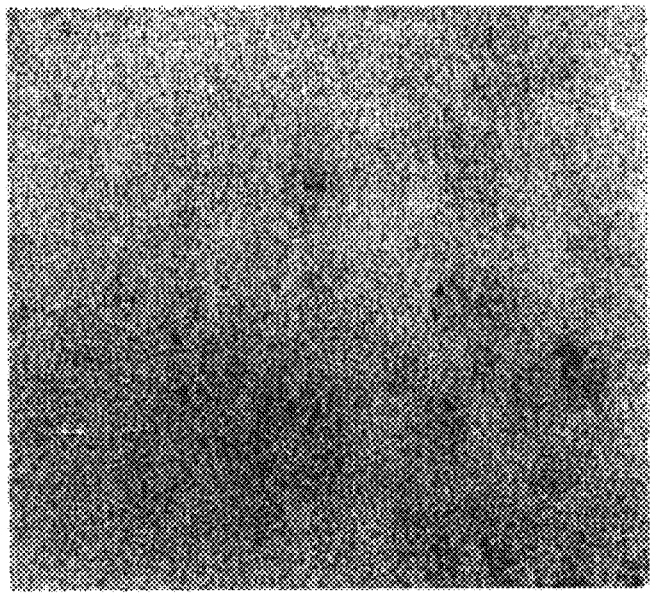
Figure 8F:
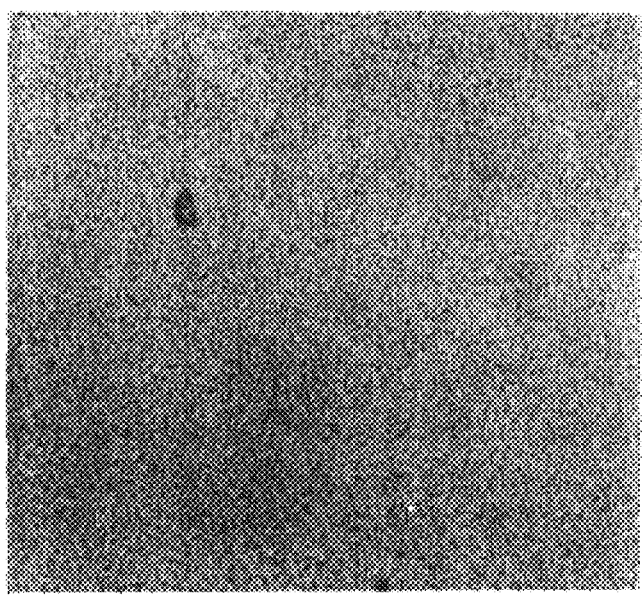

Bicarbonate activates cyanobacterial adenvicyclase. The two catalytic domains of sAC (C1 and C2) more closely resemble the active portions of cyanobacterial ACs than those from mammalian tmACs (FIG. 7a). cAMP is known to regulate respiration in cyanobacteria (Ohmori, K et al., Plant Cell Physiol., 1992, 33:21), but there is no known molecule which modulates their AC activity. In order to determine whether bicarbonate regulation of cAMP signaling is conserved in cyanobacteria, *Spirulina platensis* CyaC was expressed and purified as described (Kasahara, M. et al., Plant Cell Physiol., 1997, 38:828), and was assayed in the presence of 0–60 mM $NaHCO_3$ with 100 μM ATP and 5 mM $MnCl_2$ (Kasahara 1997; Kasahara and Ohmori, J. Biol. Chem., 1999, 274:15167). The AC activity of purified *Spirulina platensis* CyaC was stimulated 2.5 fold by the presence of bicarbonate ions (FIG. 7b). Similar to mammalian sAC, bicarbonate stimulated cyanobacterial CyaC with an $EC_{50}$ of 18.8±1.6 mM and regulation was pH independent. These data demonstrated that cyanobacterial adenylyl cyclases were also bicarbonate sensitive.

Example 3 sAC is an Oncogene

Focus Formation Assay A full length cDNA clone from the library and the truncated clone as described above were expressed in mammalian cells under the control of the cytomegalorvirus (CMV) promoter. The vector used, pBK-CMV is part of the λXZAP library construction system (STRATAGENE). To generate a mammalian expression vector from a library cDNA clone, we deleted a small piece of the vector DNA which removed a bacterial promoter sequence which brought the CMV promoter into proximity of the inserted cDNA.

For Rap1, we used wild type Rap1 in a CMV promoter vector (gift of Dr. Xin-Yun Huang, Department of Physiology, Weill Cornell Medical College) and for RAS, we used v-Ras in CMV promoter vector (gift of Dr. Marvin Gershengorn, Department of Medicine, Weill Cornell Medical College). Vector control was pBK-CMV with no insert. The tmAC control was rat Type II adenylyl cyclase in pCIS expression plasmid and the Gs* control is the alpha subunit of Gs protein with a point mutation converting the glutamine at amino acid 227 to leucine expressed in pcDNA1.2 (gift of Drs. Henry Bourne and Bruce Conklin, University of San Francisco).

One microgram of the indicated plasmids were transfected into low background (kind gift of Dr, Stuart Aaronson, Mt. Sinai Medical School) NIH 3T3 cells using lipofectamine (Life Technologies, Inc.) according to manufacturers instructions. Growth media (D-MEM plus 10% calf serum) was changed every three days and foci were scored at the end of three weeks. For photographing, plates were stained with Giemsa stain as described previously (Zhou et al., 1994).

The truncated $sAC_t$ transformed NIH 3T3 cells by focus-forming assay and produced as many foci as the oncogenic form of Ras. Furthermore, Rap1 protein, which selectively blocked transformation by oncogenic Ras proteins, also blocked transformation by $sAC_t$ suggesting sAC and Ras may share their biochemical mechanism of transformation The results are shown in Table 3.

TABLE 3

Foci Formation in NIH3T3 cells

| Plasmid(s) (1 μg) | Expt. #1 | Expt. #2 | Expt. #3* |
| --- | --- | --- | --- |
| Vector | 13 | 12 | 0 |
| v-Ras | 50 | 76 | 32 |
| sAC-t | 124 | 120 | 22 |
| sAC-fl | 26 | 47 | 0 |
| v-Ras + Rap1 | | | 2 |
| sAC + Rap1 | | | 1 |

Average number of Foci on at least 2 independent plates.
*Expt. 3 performed in Low Background NIH3T3 cells.

Full-length sAC was less oncogenic, inducing more foci than vector alone but less than $sAC_t$. By this criteria sAC is an oncogene.

FIG. 8 is a photograph of foci stained with Giemsa. The panels are NIH 3T3 cells transfected with the indicated plasmids. Foci appear as dark blotches of cells.

Soft Agar Assay We tested the ability of $sAC_t$ and $sAC_{fl}$ to support anchorage independent growth in soft agar. Low background NIH 3T3 cells were transfected as above. Two day, later, cells were trypsinized, counted and $10^5$ cells were replated into growth media plus 0.5% agarose in 60 mm tissue culture plates. Fresh media plus 0.5% agarose was overlaid each week and colony formation was scored after three weeks.

TABLE 4

Soft Agar Assay

| Plasmid | # of colonies |
| --- | --- |
| Vector | 6 |
| v-Ras | 120 |
| sAC-t | 70 |
| sAC-fl | 50 |
| tmAC-2 | 9 |

Average of 2 plates

The results shown in Table 4 demonstrate that sAC is oncogenic; it confers the ability to grow in soft agar.

Expression of sAC in various cell lines and platelets Human embryonal kidney cells (HEK293) expressed full length sAC and its 120 kD and 48 kD isoforms. Human lymphoblastoid T and B cells (Jurkat and 5/2, respectively) expressed predominantly the 48 kD isoform and human platelets predominantly the 45 kD and 48 kD isoforms with no 120 kD isoform detectable. One mouse germ cell line (GC1) expressed all isoforms including 120 kD, a second mouse germ cell line (GC2) expressed all except the 120 kD isoform.

sAC protein is elevated in human tumors We compared sAC protein expression in human colon cancer samples and surrounding normal colon tissue. Western blot analysis is shown in FIG. 9. Both αC1-C2 and αC-term antisera demonstrate that full-length sAC is upregulated in two out of three primary colon carcinomas tested. Additionally, αC1-C2 shows that the 120 kD isoform is also upregulated. Because less stringent washing conditions were used in these Western blots, additional, nonspecific bands are seen, and we do not know yet whether the 45 kD and 48 kD isoforms of sAC are also upregulated in these human tumors.

Full length and the 120 kD isoform of sAC are upregulated in the colon of Min mice Min is an autosomal dominant mutation that predisposes mice to develop intestinal tract adenomas. Min heterozygous (Min/+) mice develop, on average, more than 50 tumors throughout the entire length of their intestinal tract and rarely live past 150 days of age (Shoemaker, A. R. et al., BBA, 1997, 1332:F25–48). Min maps to a nonsense mutation in the adenomatous polyposis coli (APC) tumor suppressor gene. We compared sAC expression in colons from wild type littermates, 'normal' colon from Min/+mice, and tumors from Min mice. As with human colon carcinomas, both full-length sAC and the 120 kD isofonn, but not the 48 kD isoform, are upregulated in tumors compared to wild type colon. Surprisingly, both sAC forms are also upregulated in Min/+'normal' colon which does not yet have visually detectable adenomas. We cannot exclude however that the Min/+'normal' colon tested contained microscopic adenomas. This 'normal' colon still possesses a mutant APC gene thought to generate a dominant negative form of the protein, which contributes to a pre-cancerous state in these cells (Mahmoud, N. N. et al., Cancer Res., 1997, 57:5045–5050). Upregulation of sAC protein in these "pre-cancerous" cells suggests sAC is a very early marker for tumorigenesis.

Example 4 sAC Expression is Inducible

The commercially available (Invitrogen) ecdysone inducible system (No, D. et al., PNAS, 1996, 93:3346–3351) is based on an insect hormone regulated transcriptional activator, the ecdysone receptor (EcR). This system takes advantage of the specificity of EcR for its own response element, and the lack of any cross-reactivity by any mammalian transcription factor. We stably introduced both the EcR and its requisite partner, Retinoid X Receptor (RXR) into NIH3T3 cells. Additionally, to confirm the efficacy of this expression system, we performed pilot experiments with 3T3 cells transiently transfected with both plasmids. Doubly transfected cells displayed a ponasterone A (a synthetic ecdysone analog) dependent increase in sAC activity. This induction was overcome by co-expression of sAC antisense (αsAA). The sequence was the entire sAC truncated (sAC trunc) sequence cloned in reverse orientation with respect to the promoter. The coding sequence for sAC trunc was approximately 1 through 1710 and the antisense was nucleotides 1710 through 1. For the antisense experiment, we transiently transfected three plasmids into NIH3T3 cells: 1) Ecdysone receptor/RXR expression plasmid; 2) sAC trunc expression plasmid (driven by ecdysone promoter) and 3) antisense expression plasmid (driven by ecdysone promoter). In the triply transfected cells, there was no increase in sAC activity following ponasterone A addition.

Example 5

Screening Assay for sAC Inhibitors

For this assay, MacConkey-maltose plates are prepared. To MacConkey agar base (Difco) add 40 mg MacConkey agar base per liter H2O. Autoclave. Keep at 50° C. Make 205 maltose, and filter sterilize. Add 20% maltose per liter MacConkey agar base and the desired antibodies. Pour the plates.

For M63 plates: 1. Make 2×M63 basic salt: 27.2 g $KH_2PO_4$, 4 g$(NH_4)_2SO4$ and $FeSO_4·7H_2O$ are added to 1 liter $H_2O$, adjust pH to 7.0 by KOH, autoclave to sterilize. Make 2×agar. 15 g/500 ml Bacto-Agar and Autoclave. Make 1×M63-agar by adding 500 ml of 2×M63 basic salt and 2×agar after cooling at 50° C. add 1 ml sterile 1 M MgSO4, 25–30 ml 20% maltose, and 10 mg/ml arginine. Pour the plate.

Assay: Transform TP2000 (cya-) or WTC-3 (cya-, cpdA-) with a plasmid or the control plasmid. For negative control use: pProExHaH6. For positive control use pProExHAH6-$G_{sa}Q$-$IC_1IIC_2$. After transformation, grow up the cells overnight with antibiotics. Take 100 μg cells, spin down and wash once the cells withe 1×M63 medium (essential, carry-over LB interferes the assay). Resuspend the cells with 1×M63 medium. Spot the M63-maltose or MacConkey-maltose plate which has 100 μM IPTG. The AC complementation is best at 30° C., not 37° C.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various patents, patent applications, and publications are cited herein, the disclosures of which are incorporated by reference in their entireties.

What is claimed:

1. An isolated nucleic acid molecule which comprises a nucleic acid sequence encoding a polypeptide, which polypeptide comprises adenylyl cyclase catalytic domains C1 and C2 which is at least 85% identical to the 50 kD-terminal domain comprising catalytic domains C1 and C2 of soluble adenylyl cyclase encoded by SEQ ID NO: 1 or SEQ ID NO: 11, wherein the polypeptide has the biological property of catalyzing the production of cyclic AMP and the enzymatic activity of the polypeptide is stimulated by bicarbonate.

2. An isolated nucleic acid molecule according to claim 1, which encodes a mammalian soluble adenylyl cyclase.

3. An isolated nucleic acid molecule according to claim 2, which encodes a human soluble adenylyl cyclase.

4. A vector comprising the nucleic acid molecule according to claim 1.

5. An expression vector comprising the nucleic acid molecule according to claim 1 operably associated with an expression control sequence.

6. The vector of claim 5 which is a non-viral vector.

7. The vector of claim 6 wherein the vector is pBK-CMV.

8. A host cell comprising the expression vector according to claim 5.

9. The host cell according to claim 8, wherein the host cell is a mammalian host cell.

10. The host cell according to claim 9, wherein the mammalian host cell is a human host cell.

11. A method for producing a soluble adenylyl cyclase, which method comprises isolating a soluble adenylyl cyclase expressed by the host cell of claim 8 cultured under conditions that permit expression of the soluble adenylyl cyclase by the host cell.

12. The method of claim 11 wherein the soluble adenylyl cyclase is isolated using an anti-soluble adenylyl cyclase specific antibody.

13. An isolated nucleic acid which encodes a polypeptide having an amino acid sequence as set out in SEQ ID NO: 1 or SEQ ID NO: 11.

14. An isolated nucleic acid molecule according to claim 13, which encodes a mammalian soluble adenylyl cyclase.

15. An isolated nucleic acid molecule according to claim 14, which encodes a human soluble adenylyl cyclase.

16. A vector comprising the nucleic acid molecule according to claim 13.

17. An expression vector comprising the nucleic acid molecule according to claim 13 operably associated with an expression control sequence.

18. The vector of claim 17 which is a non-viral vector.

19. The vector of claim 18 wherein the vector is pBK-CMV.

20. A host cell comprising the expression vector according to claim 17.

21. The host cell according to claim 20, wherein the host cell is a mammalian host cell.

22. The host cell according to claim 21, wherein the mammalian host cell is a human host cell.

23. A method for producing a soluble adenylyl cyclase, which method comprises isolating a soluble adenylyl cyclase expressed by the host cell of claim 20 cultured under conditions that permit expression of the soluble adenylyl cyclase by the host cell.

24. The method of claim 23 wherein the soluble adenylyl cyclase is isolated using an anti-soluble adenylyl cyclase specific antibody.

25. An isolated nucleic acid molecule encoding a polypeptide having the biological property of catalyzing the production of cyclic AMP and the enzymatic activity of the polypeptide is stimulated by bicarbonate, which nucleic acid molecule hybridizes when incubated at 65° C. overnight and washed three times in 0.5×SSC/0.1% SDS for 15 minutes at 65° C. to a nucleic acid having a sequence set out in SEQ ID NO: 2 or SEQ ID NO: 12.

26. An isolated nucleic acid molecule according to claim 25, which encodes a mammalian soluble adenylyl cyclase.

27. An isolated nucleic acid molecule according to claim 26, which encodes a human soluble adenylyl cyclase.

28. A vector comprising the nucleic acid molecule according to claim 25.

29. An expression vector comprising the nucleic acid molecule according to claim 25 operably associated with an expression control sequence.

30. The vector of claim 29 which is a non-viral vector.

31. The vector of claim 30 wherein the vector is pBK-CMV.

32. A host cell comprising the expression vector according to claim 29.

33. The host cell according to claim 32, wherein the host cell is a mammalian host cell.

34. The host cell according to claim 33, wherein the mammalian host cell is a human host cell.

35. A method for producing a soluble adenylyl cyclase, which method comprises isolating a soluble adenylyl cyclase expressed by the host cell of claim 32 cultured under conditions that permit expression of the soluble adenylyl cyclase by the host cell.

36. The method of claim 35 wherein the soluble adenylyl cyclase is isolated using an anti-soluble adenylyl cyclase specific antibody.

* * * * *

SEQUENCE LISTING

<160> NUMBER OF SEQ ID NOS: 12

<210> SEQ ID NO 1
<211> LENGTH: 1608
<212> TYPE: PRT
<213> ORGANISM: Artificial Sequence
<220> FEATURE:
<223> OTHER INFORMATION: Description of Artificial Sequence:rat soluble
      adenylyl cyclase

<400> SEQUENCE: 1

```
Met Ser Ala Arg Arg Gln Glu Leu Gln Asp Arg Ala Ile Val Lys Ile
  1               5                  10                  15

Ala Ala His Leu Pro Asp Leu Ile Val Tyr Gly Asp Phe Ser Pro Glu
                 20                  25                  30

Arg Pro Ser Val Lys Cys Phe Asp Gly Val Leu Met Phe Val Asp Ile
             35                  40                  45

Ser Gly Phe Thr Ala Met Thr Glu Lys Phe Ser Thr Ala Met Tyr Met
     50                  55                  60

Asp Arg Gly Ala Glu Gln Leu Val Glu Ile Leu Asn Tyr Tyr Ile Ser
 65                  70                  75                  80

Ala Ile Val Glu Lys Val Leu Ile Phe Gly Gly Asp Ile Leu Lys Phe
                 85                  90                  95

Ala Gly Asp Ala Leu Leu Ala Leu Trp Lys Val Glu Arg Lys Gln Leu
            100                 105                 110

Lys Asn Ile Ile Thr Val Val Ile Lys Cys Ser Leu Glu Ile His Gly
        115                 120                 125

Leu Phe Glu Ala Lys Glu Val Glu Glu Gly Leu Asp Ile Arg Val Lys
    130                 135                 140

Ile Gly Leu Ala Ala Gly His Ile Thr Met Leu Val Phe Gly Asp Glu
145                 150                 155                 160

Thr Arg Asn Tyr Phe Leu Val Ile Gly Gln Ala Val Asp Asp Val Arg
                165                 170                 175

Leu Ala Gln Asn Met Ala Gln Met Asn Asp Val Ile Leu Ser Pro Asn
            180                 185                 190

Cys Trp Gln Leu Cys Asp Arg Ser Met Ile Glu Ile Glu Arg Ile Pro
        195                 200                 205

Asp Gln Arg Ala Val Lys Val Ser Phe Leu Lys Pro Pro Pro Thr Phe
    210                 215                 220

Asn Phe Asp Glu Phe Phe Ala Lys Cys Met Ala Phe Met Asp Tyr Tyr
225                 230                 235                 240

Pro Ser Gly Asp His Lys Asn Phe Leu Arg Leu Ala Cys Met Leu Glu
                245                 250                 255

Ser Asp Pro Glu Leu Glu Leu Ser Leu Gln Lys Tyr Val Met Glu Ile
            260                 265                 270

Ile Leu Lys Gln Ile Asp Asp Lys Gln Leu Arg Gly Tyr Leu Ser Glu
        275                 280                 285

Leu Arg Pro Val Thr Ile Val Phe Val Asn Leu Met Phe Lys Glu Gln
    290                 295                 300

Asp Lys Ala Glu Val Ile Gly Ser Ala Ile Gln Ala Ala Cys Val His
305                 310                 315                 320

Ile Thr Ser Val Leu Lys Val Phe Arg Gly Gln Ile Asn Lys Val Phe
                325                 330                 335

Met Phe Asp Lys Gly Cys Ser Phe Leu Cys Val Phe Gly Phe Pro Gly
```

-continued

```
                340                 345                 350
Glu Lys Ala Pro Asp Glu Ile Thr His Ala Leu Glu Ser Ala Val Asp
                355                 360                 365
Ile Phe Asp Phe Cys Ser Gln Val His Lys Ile Arg Thr Val Ser Ile
370                 375                 380
Gly Val Ala Ser Gly Ile Val Phe Cys Gly Ile Val Gly His Thr Val
385                 390                 395                 400
Arg His Glu Tyr Thr Val Ile Gly Gln Lys Val Asn Ile Ala Ala Arg
                405                 410                 415
Met Met Met Tyr Tyr Pro Gly Ile Val Thr Cys Asp Ser Val Thr Tyr
                420                 425                 430
Asp Gly Ser Asn Leu Pro Ala Tyr Phe Phe Lys Glu Leu Pro Lys Lys
                435                 440                 445
Val Met Lys Gly Val Ala Asp Pro Gly Pro Val Tyr Gln Cys Leu Gly
450                 455                 460
Leu Asn Glu Lys Val Met Phe Gly Met Ala Tyr Leu Ile Cys Asn Arg
465                 470                 475                 480
Tyr Glu Gly Tyr Pro Leu Leu Gly Arg Val Arg Glu Ile Asp Tyr Phe
                485                 490                 495
Met Ser Thr Met Lys Asp Phe Leu Met Thr Asn Cys Ser Arg Val Leu
                500                 505                 510
Met Tyr Glu Gly Leu Pro Gly Tyr Gly Lys Ser Gln Val Leu Met Glu
                515                 520                 525
Ile Glu Tyr Leu Ala Ser Gln His Glu Asn His Arg Ala Val Ala Ile
                530                 535                 540
Ala Leu Thr Lys Ile Ser Phe His Gln Asn Phe Tyr Thr Ile Gln Ile
545                 550                 555                 560
Leu Met Ala Asn Val Leu Gly Leu Asp Thr Cys Lys His Tyr Lys Glu
                565                 570                 575
Arg Gln Thr Asn Leu Gln Asn Arg Val Lys Thr Leu Leu Asp Asp Lys
                580                 585                 590
Tyr His Cys Leu Leu Asn Asp Ile Phe His Val Gln Phe Pro Val Ser
                595                 600                 605
Arg Glu Met Ser Arg Met Ser Lys Ile Arg Lys Gln Lys Gln Leu Glu
                610                 615                 620
Ala Leu Phe Met Lys Ile Leu Glu Gln Thr Val Arg Glu Glu Arg Ile
625                 630                 635                 640
Ile Phe Ile Ile Asp Glu Ala Gln Phe Val Asp Val Ala Ser Trp Ala
                645                 650                 655
Phe Ile Glu Lys Leu Ile Arg Ser Met Pro Ile Phe Ile Val Met Ser
                660                 665                 670
Leu Cys Pro Phe Pro Glu Thr Pro Cys Ala Ala Ala Asn Ala Ile Met
                675                 680                 685
Lys Asn Arg Asn Thr Thr Tyr Ile Thr Leu Gly Thr Met Gln Pro Gln
                690                 695                 700
Glu Ile Arg Asp Lys Val Cys Val Asp Leu Val Ser Ser Ile Pro
705                 710                 715                 720
Arg Glu Leu Asp Ser Tyr Leu Val Glu Gly Ser Cys Gly Ile Pro Tyr
                725                 730                 735
Tyr Cys Glu Glu Leu Leu Lys Asn Leu Asp His His Arg Ile Leu Ile
                740                 745                 750
Phe Gln Gln Ala Glu Ala Glu Glu Lys Thr Asn Val Thr Trp Asn Asn
                755                 760                 765
```

-continued

```
Leu Phe Lys Tyr Ser Val Lys Pro Thr Glu Asp Met Tyr Leu Tyr Thr
    770                 775                 780
Ser Ile Ala Ala Gly Gln Lys Glu Ala Cys Tyr Leu Thr Ser Gly Val
785                 790                 795                 800
Arg Leu Lys Asn Leu Ser Pro Pro Ala Ser Leu Lys Glu Ile Ser Leu
                805                 810                 815
Val Gln Leu Asp Ser Met Ser Leu Ser His Gln Met Leu Val Arg Cys
                820                 825                 830
Ala Ala Ile Ile Gly Leu Thr Phe Thr Thr Glu Leu Leu Phe Glu Ile
                835                 840                 845
Leu Pro Cys Trp Asn Met Lys Met Met Ile Lys Ala Leu Ala Thr Leu
850                 855                 860
Val Glu Ser Asn Val Phe Asp Cys Phe Arg Ser Ser Lys Asp Leu Gln
865                 870                 875                 880
Leu Ala Leu Lys Gln Asn Val Thr Thr Phe Glu Val His Tyr Arg Ser
                885                 890                 895
Leu Ser Leu Lys Ser Lys Glu Gly Leu Ala Tyr Ser Glu Glu Glu Gln
                900                 905                 910
Leu Arg Glu Met Glu Gly Glu Val Ile Glu Cys Arg Ile Leu Arg Phe
                915                 920                 925
Cys Arg Pro Ile Met Gln Lys Thr Ala Tyr Glu Leu Trp Leu Lys Asp
930                 935                 940
Gln Lys Lys Val Leu His Leu Lys Cys Ala Arg Phe Leu Glu Glu Ser
945                 950                 955                 960
Ala His Arg Cys Asn His Cys Arg Asn Arg Asp Phe Ile Pro Tyr His
                965                 970                 975
His Phe Ile Ala Asp Ile Arg Leu Asn Thr Leu Asp Met Asp Thr Val
                980                 985                 990
Lys Lys Met Val Lys Ser His Gly Phe Lys Thr Glu Asp Glu Val Ile
                995                 1000                1005
Phe Ser Lys Ser Glu Ile Pro Arg Lys Phe Lys Phe Pro Glu Asn Ile
    1010                1015                1020
Ser Ile Thr Glu Thr Arg Glu Lys Ile Leu His Phe Phe Asp Asn Val
1025                1030                1035                1040
Ile Ile Lys Met Arg Thr Ser Gln Asp Asp Val Ile Pro Leu Glu Ser
                1045                1050                1055
Cys His Cys Glu Glu Leu Leu Gln Ile Val Ile Leu Pro Leu Ala Gln
                1060                1065                1070
His Phe Val Ala Leu Glu Glu Asn Asn Lys Ala Leu Tyr Tyr Phe Leu
    1075                1080                1085
Glu Leu Ala Ser Ala Tyr Leu Ile Leu Gly Asp Asn Tyr Asn Ala Tyr
    1090                1095                1100
Met Tyr Leu Gly Glu Gly Glu Arg Leu Leu Lys Ser Leu Thr Asn Glu
1105                1110                1115                1120
Asp Ser Trp Ser Gln Thr Phe Gly Tyr Ala Thr Phe Tyr Ser Leu Lys
                1125                1130                1135
Gly Glu Ile Cys Phe Asn Met Gly Gln Met Val Leu Ala Lys Lys Met
                1140                1145                1150
Leu Arg Lys Ala Leu Lys Leu Leu Asn Arg Met Phe Pro Cys Asn Leu
    1155                1160                1165
Leu Ser Leu Thr Phe Gln Met His Ile Glu Lys Asn Arg Leu Ser His
    1170                1175                1180
```

-continued

```
Phe Met Asn Gln His Thr Gln Glu Gly Ser Leu Pro Gly Lys Leu
1185                1190                1195                1200

Ala Gln Leu Phe Leu Gln Ser Ser Cys Phe Ser Leu Leu Trp Lys Ile
            1205                1210                1215

Tyr Ser Leu Asn Phe Phe His Tyr Lys Tyr Tyr Gly Arg Leu Ala
            1220                1225                1230

Ala Ile Met Gln Met Asn Thr Ser Leu Glu Thr Gln Asn Asn Phe Gln
        1235                1240                1245

Ile Ile Lys Ala Phe Leu Asp Phe Ser Leu Tyr Arg His Leu Ala Gly
        1250                1255                1260

Tyr Glu Gly Val Trp Phe Lys Tyr Glu Ile Leu Val Met Glu Gln Leu
1265                1270                1275                1280

Leu Asn Leu Pro Leu Lys Gly Glu Ala Phe Glu Ile Met Ala Tyr Ala
            1285                1290                1295

Ala Asp Ala Leu Gly His Ile Lys Phe Leu Thr Gly His Leu Asp Leu
        1300                1305                1310

Ala Ile Glu Leu Gly Ser Arg Ala His Lys Met Trp Ser Leu Leu Arg
        1315                1320                1325

Asn Pro Asn Lys Tyr His Met Val Leu Cys Arg Leu Ser Lys Pro Leu
        1330                1335                1340

Phe Leu Lys Ser Arg Tyr Lys His Leu Val Gln Val Leu Gly Trp Leu
1345                1350                1355                1360

Trp Asp Leu Ser Val Thr Glu Glu His Ile Phe Ser Lys Ala Phe Phe
            1365                1370                1375

Tyr Phe Val Cys Leu Asp Ile Met Leu Tyr Ser Gly Phe Ile Tyr Arg
        1380                1385                1390

Thr Phe Glu Glu Cys Leu Glu Phe Ile His His Asn Glu Asp Asn Arg
        1395                1400                1405

Ile Leu Lys Phe Gln Ser Gly Leu Leu Leu Gly Leu Tyr Ser Cys Ile
        1410                1415                1420

Ala Val Trp Tyr Ala Arg Leu Gln Glu Trp Asp Asn Phe Tyr Lys Phe
1425                1430                1435                1440

Ser Asn Arg Ala Lys Thr Leu Val Thr Arg Arg Thr Pro Thr Val Leu
            1445                1450                1455

Tyr Tyr Glu Gly Ile Ser Arg Tyr Met Glu Gly Gln Val Leu His Leu
            1460                1465                1470

Gln Lys Gln Ile Glu Glu Gln Ala Glu Asn Ala Gln Asp Ser Gly Val
        1475                1480                1485

Glu Leu Leu Lys Ala Leu Glu Thr Leu Val Ala Gln Asn Thr Thr Gly
        1490                1495                1500

Pro Val Phe Tyr Pro Arg Leu Tyr His Leu Met Ala Tyr Val Cys Ile
1505                1510                1515                1520

Leu Met Gly Asp Gly His Ser Cys Asp Phe Phe Leu Asn Thr Ala Leu
            1525                1530                1535

Glu Leu Ser Glu Thr Gln Gly Asn Leu Leu Glu Lys Cys Trp Leu Ser
            1540                1545                1550

Met Ser Lys Glu Trp Trp Tyr Ser Ala Pro Glu Leu Thr Gly Asp Gln
        1555                1560                1565

Trp Leu Gln Thr Val Leu Ser Leu Pro Ser Trp Asp Lys Ile Val Ser
    1570                1575                1580

Gly Asn Val Thr Leu Gln Asp Val Gln Lys Asn Lys Phe Leu Met Arg
1585                1590                1595                1600

Val Asn Ile Leu Asp Asn Pro Phe
```

1605

<210> SEQ ID NO 2
<211> LENGTH: 5177
<212> TYPE: DNA
<213> ORGANISM: Artificial Sequence
<220> FEATURE:
<223> OTHER INFORMATION: Description of Artificial Sequence:rat soluble
      adenylyl cyclase

<400> SEQUENCE: 2

```
ggacagacat ggcacttctg ctgtcttcaa aataataaca ccagacccc  ttcctgttct      60
ctacattcct gaaagatcta gtctaatcta ggctccaact tttcctccgt cttggagaac     120
agagatgacc aaagttcagt ttccagctca caactgcctg aaagtccagc tccagaggat     180
ctgacacact tttctggcct ccatgcaaca catgttgcac aaaaacagac acacacacat     240
acagagaaga cctccttggg gagacagctt cctggcactg aaaaatcctg accactgtcc     300
ttgaacatga gtgcccgaag gcaggaatta caggacaggg caatcgtcaa gatagctgct     360
cacttaccgg acctcattgt ctatggagat ttctctcccg agcggccgtc agtgaaatgt     420
tttgatggag ttctgatgtt tgtcgatatt tcaggcttta ctgcaatgac tgagaagttc     480
agcacagcca tgtacatgga ccgaggagcc gagcagctgg tggagatcct caactactac     540
ataagtgcga tagtggagaa agtactgatt tttggaggag acatcctaaa atttgcaggt     600
gacgccttgt tggccctgtg gaaagtggaa cgaaagcaac tgaagaatat catcacggtg     660
gtaattaaat gcagcctgga gattcatggc ttgtttgaag ccaaggaggt tgaagaaggc     720
ctggatattc gagttaagat aggactggct gctggccaca tcaccatgtt ggtcttgggg     780
gatgaaacac ggaactactt cctggtgatt ggccaagcgg tggatgatgt acgccttgct     840
cagaacatgg ctcagatgaa tgatgttatt ctgtcaccaa actgctggca gctctgtgat     900
cggagcatga ttgaaatcga gaggattccg atcagagag cagttaaggt tagcttctta     960
aaaccacccc caacttttaa cttcgacgag ttttttgcca agtgtatggc cttcatggat    1020
tattatcctt ctggtgacca caaaaacttc ctaaggcttg cctgcatgct ggagtctgat    1080
cctgaactcg agttgtctct acaaaagtat gtgatgaaaa tcattttgaa gcagattgat    1140
gacaagcagc ttcggggcta tttatctgag cttcgtcctg tgacgatcgt gtttgtgaac    1200
ttgatgtttta aagagcaaga caaagcgaaa gtcataggat cagccatcca agctgcctgt    1260
gtgcacatca cttccgtctt gaaggtcttc cgaggccaga tcaataaggt cttcatgttt    1320
gataagggct gctccttcct ctgtgtcttc ggtttccctg ggaaaaaggc ccctgacgag    1380
atcactcacg ctttggaaag tgccgtggat atattcgact tctgctctca ggtccacaaa    1440
atccgtactg tctccatcgg cgtcgccagt gggattgtct ctgtgggat cgttggacac    1500
actgtgagac acgagtacac agtcattggc caaaaggtca atattgctgc caggatgatg    1560
atgtattacc caggcatcgt gacctgcgac tctgtcacat acgatggcag caacctgcca    1620
gcctactttt taaagagct tccaaagaaa gtcatgaaag gagttgcgga tcccggacca    1680
gtgtatcagt gtctgggcct caatgagaaa gtcatgtttg gtatggccta tctcatctgc    1740
aacagatatg agggctaccc tttgctgggt cgtgttaggg agatcgacta tttcatgtct    1800
actatgaagg actttctgat gacgaactgc agccgagttc taatgtatga aggattgcca    1860
ggatatggga aaagccaggt acttatgaa atcgagtatc tggcctccca gcatgagaac    1920
cataggggctg ttgctattgc actgactaag atcagcttcc atcaaaattt ttacactatc    1980
```

```
                                                        -continued cagatactca tggctaacgt actaggtctg gatacttgta aacattacaa agaacgacag    2040
accaatcttc aaaatagagt caagacgctg ttggatgata aataccactg tctccttaac    2100
gacatcttcc atgttcagtt ccccgttccc cgggagatgt ccaggatgag caagataaga    2160
aagcagaagc aactggaagc tctgtttatg aagatcctgg agcaaacagt gagggaagaa    2220
aggattatct tcatcatcga cgaggcccag tttgtggacg tagcctcctg ggccttcata    2280
gaaaagctca tccggtccat gcccatcttc attgttatgt ccctgtgtcc cttccctgaa    2340
actccctgcg cagctgccaa tgccataatg aagaaccgga acaccaccta catcacactc    2400
ggtaccatgc agcctcagga aatccgggac aaggtctgtg ttgacctgag tgtaagcagc    2460
atccccagag agcttgactc gtacctggtg gaggggagct gcgggattcc gtattactgt    2520
gaggaactgc tgaaaaacct cgaccaccac agaattctca ttttccaaca agcagaggct    2580
gaggaaaaga caaacgtgac ctggaataac ctgttcaagt actctgttaa gccgacagaa    2640
gacatgtatc tgtatacttc catagccgcg ggacagaaag aagcctgtta ccttacaagt    2700
ggtgtcagac taagaacttg tcacctcca gcatcgctca aagaaatctc tctggttcaa    2760
ctggacagca tgagcctttc ccatcagatg ctggtgaggt gtgctgctat cattggtcta    2820
accttcacca cagagctgct gtttgagatt ctccctgct ggaacatgaa gatgatgatc    2880
aaggccctgg ccaccctagt ggaatcaaat gtctttgatt gctttcggag tagcaaagac    2940
cttcaactag cctaaagca aaacgtgacc acgtttgaag ttcattatcg ctctttgtcc    3000
ctgaagtcca aggaagggtt agcttacagt gaggaggagc agctccgtga atggaagga    3060 gaggtgattg aatgccgcat ccttcggttc tgcagaccca taatgcagaa gacagcctac    3120
gaactgtggc tcaaggacca aagaaagtc ttgcatctga aatgcgcccg cttttggag    3180 gagagtgccc atcggtgcaa ccactgcaga aacagagact tcattcctta ccaccacttc    3240
atagcggaca ttcgactcaa cactctggac atggatactg tcaagaagat ggtgaagtcc    3300
cacggattta aaactgaaga cgaggtcatc ttttctaaat cagagatccc caggaaattc    3360
aaattccccg agaacatcag catcacagaa acaaggaaa aatcttgca tttctttgac    3420 aatgttatca taagatgag gacgtctcag gatgatgtca tccctctaga atcgtgccat    3480
tgtgaggagc tgctccagat tgtcatcttg cctctggccc agcatttcgt agccttagaa    3540
gaaaacaaca aagccttgta ctacttccta gaacttgcat ctgcctatct catcctggga    3600
gacaactata acgcatacat gtatttgggc gaagggaaa ggctgttgaa atctctgaca    3660
aatgaagatt cttggagtca gacctttgaa tatgctacgt tttatagtct caaaggtgag    3720
atctgtttta atatgggaca gatggtgctc gccaagaaaa tgctgagaaa agcactgaag    3780
cttctcaaca gaatgtttcc ctgcaatcta ctctccctga cttccaaat gcacattgag    3840 aaaaacagac tctcccactt catgaaccag catacccagg agggctcgct gccagggaag    3900
aagctggccc aacttttcct gcagtcgtcc tgcttctccc tgctgtggaa gatctatagc    3960
ttgaacttct ttttccacta caagtactat ggtcgtctgg cagcaataat gcagatgaac    4020
acctcgttag aaactcaaaa caatttccag atcatcaagg cttcctggga cttttccctg    4080
taccgccatc tggctggata cgagggcgtg tggttcaaat atgaaatcct ggtcatggag    4140
cagctcttga acctcccct gaaaggcgaa gcctttgaaa tcatggccta tgcagccgac    4200
gcactgggcc atatcaagtt cttaaccggt catctggact tggccattga attaggctcc    4260
cgagctcaca agatgtggtc acttctccgg aatcccaaca aataccatat ggttctctgc    4320
agactgagta aacctctttt cttgaagagc agatacaagc atttggtcca ggtgctggga    4380
```

```
tggttgtggg acctttctgt aacagaggag cacatcttca gcaaggcatt tttctatttc    4440
gtctgcttgg acatcatgct ttattctggc ttcatttaca gaacatttga agaatgtttg    4500
gaattcatac accacaatga agacaacaga atcctcaagt tccaaagcgg actcctcctg    4560
ggactttact cctgcatagc tgtctggtac gccagacttc aggaatggga caacttttac    4620
aaatttccca atagagcgaa gactttagtg actcgaagaa ccccaacggt cctttactac    4680
gaaggaattt ctaggtatat ggaagggcaa gtcctccatc ttcagaagca aatagaagag    4740
caggccgaga atgctcagga cagtggggtg gagctactta aggccttaga gacccttgtg    4800
gctcaaaata ccactggccc cgtcttctac cccaggctct accatttgat ggcctatgtc    4860
tgtatactga tgggagacgg gcacagttgt gacttcttcc taaacacagc cttggagctc    4920
tctgagacac aggggaattt gctggagaaa tgttggctga gcatgagtaa ggaatggtgg    4980
tactcagccc ccgagttgac aggagatcaa tggcttcaga cagtcttgag tctcccatcg    5040
tgggataaaa ttgtatcagg caacgtaacc cttcaggatg ttcaaaagaa caaattcttg    5100
atgagagtta atattctgga caatcctttc taataattat gaatgagaac aaagattgca    5160
aaaaaaaaaa aaaaaaa                                                  5177
```

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 3

Thr Ala Met Tyr Met Gly
  1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 4

Glu Tyr Thr Val Ile Gly Gln Lys
  1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:tryptic
      peptide
<221> NAME/KEY: VARIANT
<222> LOCATION: (5)
<223> OTHER INFORMATION: fully degenerate for either leucine or
      glutamate

<400> SEQUENCE: 5

Met Glu Leu Glu Xaa Asp Pro Glu
  1               5

<210> SEQ ID NO 6
<211> LENGTH: 20
<212> TYPE: DNA

```
<213> ORGANISM: Artificial Sequence
<220> FEATURE:
<223> OTHER INFORMATION: Description of Artificial Sequence:primer

<400> SEQUENCE: 6
cgagcagctg gtggagatcc                                                    20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 7
gcgtgagtga tctcgtcagg ggc                                                23

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 8
cctgcttctc cctgctgtg                                                     19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 9
gcaggagtaa agtcccagg                                                     19

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:N-terminal
      region  soluble adenylyl cyclase

<400> SEQUENCE: 10

Ser Ala Arg Arg Gln Glu Leu Gln Asp Arg Ala Ile Val Lys
  1               5                  10

<210> SEQ ID NO 11
<211> LENGTH: 1610
<212> TYPE: PRT
<213> ORGANISM: Artificial Sequence
<220> FEATURE:
<223> OTHER INFORMATION: Description of Artificial Sequence:human
      soluble adenylyl cyclase

<400> SEQUENCE: 11

Met Asn Thr Pro Lys Glu Glu Phe Gln Asp Trp Pro Ile Val Arg Ile
  1               5                  10                  15

Ala Ala His Leu Pro Asp Leu Ile Val Tyr Gly His Phe Ser Pro Glu
             20                  25                  30

Arg Pro Phe Met Asp Tyr Phe Asp Gly Val Leu Met Phe Val Asp Ile
         35                  40                  45

Ser Gly Phe Thr Ala Met Thr Glu Lys Phe Ser Ser Ala Met Tyr Met
```

-continued

```
               50                   55                   60
Asp Arg Gly Ala Glu Gln Leu Val Glu Ile Leu Asn Tyr His Ile Ser
 65                  70                   75                   80
Ala Ile Val Glu Lys Val Leu Ile Phe Gly Gly Asp Ile Leu Lys Phe
                     85                   90                   95
Ala Gly Asp Ala Leu Leu Ala Leu Trp Arg Val Glu Arg Lys Gln Leu
                    100                  105                  110
Lys Asn Ile Ile Thr Val Val Ile Lys Cys Ser Leu Glu Ile His Gly
                    115                  120                  125
Leu Phe Glu Thr Gln Glu Trp Glu Glu Gly Leu Asp Ile Arg Val Lys
                    130                  135                  140
Ile Gly Leu Ala Ala Gly His Ile Ser Met Leu Val Phe Gly Asp Glu
145                  150                  155                  160
Thr His Ser His Phe Leu Val Ile Gly Gln Ala Val Asp Asp Val Arg
                    165                  170                  175
Leu Ala Gln Asn Met Ala Gln Met Asn Asp Val Ile Leu Ser Pro Asn
                    180                  185                  190
Cys Trp Gln Leu Cys Asp Arg Ser Met Ile Glu Ile Glu Ser Val Pro
                    195                  200                  205
Asp Gln Arg Ala Val Lys Val Asn Phe Leu Lys Pro Pro Asn Phe
                    210                  215                  220
Asn Phe Asp Glu Phe Phe Thr Lys Cys Thr Thr Phe Met His Tyr Tyr
225                  230                  235                  240
Pro Ser Gly Glu His Lys Asn Leu Leu Arg Leu Ala Cys Thr Leu Lys
                    245                  250                  255
Pro Asp Pro Glu Leu Glu Met Ser Leu Gln Lys Tyr Val Met Glu Ser
                    260                  265                  270
Ile Leu Lys Gln Ile Asp Asn Lys Gln Leu Gln Gly Tyr Leu Ser Glu
                    275                  280                  285
Leu Arg Pro Val Thr Ile Val Phe Val Asn Leu Met Phe Glu Asp Gln
                    290                  295                  300
Asp Lys Ala Glu Glu Ile Gly Pro Ala Ile Gln Asp Ala Tyr Met His
305                  310                  315                  320
Ile Thr Ser Val Leu Lys Ile Phe Gln Gly Gln Ile Asn Lys Val Phe
                    325                  330                  335
Met Phe Asp Lys Gly Cys Ser Phe Leu Cys Val Phe Gly Phe Pro Gly
                    340                  345                  350
Glu Lys Val Pro Asp Glu Leu Thr His Ala Leu Glu Cys Ala Met Asp
                    355                  360                  365
Ile Phe Asp Phe Cys Ser Gln Val His Lys Ile Gln Thr Val Ser Ile
                    370                  375                  380
Gly Val Ala Ser Gly Ile Val Phe Cys Gly Ile Val Gly His Thr Val
385                  390                  395                  400
Arg His Glu Tyr Thr Val Ile Gly Gln Lys Val Asn Leu Ala Ala Arg
                    405                  410                  415
Met Met Met Tyr Tyr Pro Gly Ile Val Thr Cys Asp Ser Val Thr Tyr
                    420                  425                  430
Asn Gly Ser Asn Leu Pro Ala Tyr Phe Phe Lys Glu Leu Pro Lys Lys
                    435                  440                  445
Val Met Lys Gly Val Ala Asp Ser Gly Pro Leu Tyr Gln Tyr Trp Gly
                    450                  455                  460
Arg Thr Glu Lys Val Met Phe Gly Met Ala Cys Leu Ile Cys Asn Arg
465                  470                  475                  480
```

-continued

```
Lys Glu Asp Tyr Pro Leu Leu Gly Arg Asn Lys Glu Ile Asn Tyr Phe
                485                 490                 495
Met Tyr Thr Met Lys Lys Phe Leu Ile Ser Asn Ser Ser Gln Val Leu
            500                 505                 510
Met Tyr Glu Gly Leu Pro Gly Tyr Gly Lys Ser Gln Ile Leu Met Lys
        515                 520                 525
Ile Glu Tyr Leu Ala Gln Gly Lys Asn His Arg Ile Ile Ala Ile Ser
    530                 535                 540
Leu Asn Lys Ile Ser Phe His Gln Thr Phe Tyr Thr Ile Gln Met Phe
545                 550                 555                 560
Met Ala Asn Val Leu Gly Leu Asp Thr Cys Lys His Tyr Lys Glu Arg
                565                 570                 575
Gln Thr Asn Leu Arg Asn Lys Val Met Thr Leu Leu Asp Glu Lys Phe
            580                 585                 590
Tyr Cys Leu Leu Asn Asp Ile Phe His Val Gln Phe Pro Ile Ser Arg
        595                 600                 605
Glu Ile Ser Arg Met Ser Thr Leu Lys Lys Gln Lys Gln Leu Glu Ile
    610                 615                 620
Leu Phe Met Lys Ile Leu Lys Leu Ile Val Lys Glu Arg Ile Ile
625                 630                 635                 640
Phe Ile Ile Asp Glu Ala Gln Phe Val Asp Ser Thr Ser Trp Arg Phe
                645                 650                 655
Met Glu Lys Leu Ile Arg Thr Leu Pro Ile Phe Ile Ile Met Ser Leu
            660                 665                 670
Cys Pro Phe Val Asn Ile Pro Cys Ala Ala Arg Ala Val Ile Lys
        675                 680                 685
Asn Arg Asn Thr Thr Tyr Ile Val Gly Ala Val Gln Pro Asn Asp
    690                 695                 700
Ile Ser Asn Lys Ile Cys Leu Asp Leu Asn Val Ser Cys Ile Ser Lys
705                 710                 715                 720
Glu Leu Asp Ser Tyr Leu Gly Glu Gly Ser Cys Gly Ile Pro Phe Tyr
                725                 730                 735
Cys Glu Glu Leu Leu Lys Asn Leu Glu His His Glu Val Leu Val Phe
            740                 745                 750
Gln Gln Thr Glu Ser Glu Lys Thr Asn Arg Thr Trp Asn Asn Leu
        755                 760                 765
Phe Lys Tyr Ser Ile Lys Leu Thr Glu Lys Leu Asn Met Val Thr Leu
    770                 775                 780
His Ser Asp Lys Glu Ser Glu Glu Val Cys His Leu Thr Ser Gly Val
785                 790                 795                 800
Arg Leu Lys Asn Leu Ser Pro Pro Thr Ser Leu Lys Glu Ile Ser Leu
                805                 810                 815
Ile Gln Leu Asp Ser Met Arg Leu Ser His Gln Met Leu Val Arg Cys
            820                 825                 830
Ala Ala Ile Ile Gly Leu Thr Phe Thr Thr Glu Leu Leu Phe Glu Ile
        835                 840                 845
Leu Pro Cys Trp Asn Met Lys Met Met Ile Lys Thr Leu Ala Thr Leu
    850                 855                 860
Val Glu Ser Asn Ile Phe Tyr Cys Phe Arg Asn Gly Lys Glu Leu Gln
865                 870                 875                 880
Lys Ala Leu Lys Gln Asn Asp Pro Ser Phe Glu Val His Tyr Arg Ser
                885                 890                 895
```

```
Leu Ser Leu Lys Pro Ser Glu Gly Met Asp His Gly Glu Glu Gln
            900                 905                 910

Leu Arg Glu Leu Glu Asn Glu Val Ile Glu Cys His Arg Ile Arg Phe
            915                 920                 925

Cys Asn Pro Met Met Gln Lys Thr Ala Tyr Glu Leu Trp Leu Lys Asp
            930                 935                 940

Gln Arg Lys Ala Met His Leu Lys Cys Ala Arg Phe Leu Glu Glu Asp
945                 950                 955                 960

Ala His Arg Cys Asp His Cys Arg Gly Arg Asp Phe Ile Pro Tyr His
                965                 970                 975

His Phe Thr Val Asn Ile Arg Leu Asn Ala Leu Asp Met Asp Ala Ile
            980                 985                 990

Lys Lys Met Ala Met Ser His Gly Phe Lys Thr Glu Glu Lys Leu Ile
            995                 1000                1005

Leu Ser Asn Ser Glu Ile Pro Glu Thr Ser Ala Phe Phe Pro Glu Asn
            1010                1015                1020

Arg Ser Pro Glu Glu Ile Arg Glu Lys Ile Leu Asn Phe Phe Asp His
1025                1030                1035                1040

Val Leu Thr Lys Met Lys Thr Ser Asp Glu Asp Ile Ile Pro Leu Glu
            1045                1050                1055

Ser Cys Gln Cys Glu Glu Ile Leu Glu Ile Val Ile Leu Pro Leu Ala
            1060                1065                1070

His His Phe Leu Ala Leu Gly Glu Asn Asp Lys Ala Leu Tyr Tyr Phe
            1075                1080                1085

Leu Glu Ile Ala Ser Ala Tyr Leu Ile Phe Cys Asp Asn Tyr Met Ala
            1090                1095                1100

Tyr Met Tyr Leu Asn Glu Gly Gln Lys Leu Leu Lys Thr Leu Lys Lys
1105                1110                1115                1120

Asp Lys Ser Trp Ser Gln Thr Phe Glu Ser Ala Thr Phe Tyr Ser Leu
            1125                1130                1135

Lys Gly Glu Val Cys Phe Asn Met Gly Gln Ile Val Leu Ala Lys Lys
            1140                1145                1150

Met Leu Arg Lys Ala Leu Lys Leu Leu Asn Arg Ile Phe Pro Tyr Asn
            1155                1160                1165

Leu Ile Ser Leu Phe Leu His Ile His Val Glu Lys Asn Arg His Phe
            1170                1175                1180

His Tyr Val Asn Arg Gln Ala Gln Glu Ser Pro Pro Gly Lys Lys
1185                1190                1195                1200

Arg Leu Ala Gln Leu Tyr Arg Gln Thr Val Cys Leu Ser Leu Leu Trp
            1205                1210                1215

Arg Ile Tyr Ser Tyr Ser Tyr Leu Phe His Cys Lys Tyr Tyr Ala His
            1220                1225                1230

Leu Ala Val Met Met Gln Met Asn Thr Ala Leu Glu Thr Gln Asn Cys
            1235                1240                1245

Phe Gln Ile Ile Lys Ala Tyr Leu Asp Tyr Ser Leu Tyr His His Leu
            1250                1255                1260

Ala Gly Tyr Lys Gly Val Trp Phe Lys Tyr Glu Val Met Ala Met Glu
1265                1270                1275                1280

His Ile Phe Asn Leu Pro Leu Lys Gly Glu Gly Ile Glu Ile Val Ala
            1285                1290                1295

Tyr Val Ala Glu Thr Leu Val Phe Asn Lys Leu Ile Met Gly His Leu
            1300                1305                1310

Asp Leu Ala Ile Glu Leu Gly Ser Arg Ala Leu Gln Met Trp Ala Leu
```

Leu Gln Asn Pro Asn Arg His Tyr Gln Ser Leu Cys Arg Leu Ser Arg
             1330             1335                 1340

Cys Leu Leu Leu Asn Ser Arg Tyr Pro Gln Leu Ile Gln Val Leu Gly
1345                 1350                 1355                 1360

Arg Leu Trp Glu Leu Ser Val Thr Gln Glu His Ile Phe Ser Lys Ala
             1365                 1370                 1375

Phe Phe Tyr Phe Val Cys Leu Asp Ile Leu Leu Tyr Ser Gly Phe Val
             1380                 1385                 1390

Tyr Arg Thr Phe Glu Glu Cys Leu Glu Phe Ile His Gln Tyr Glu Asn
             1395                 1400                 1405

Asn Arg Ile Leu Lys Phe His Ser Gly Leu Leu Leu Gly Leu Tyr Ser
        1410                 1415                 1420

Ser Val Ala Ile Trp Tyr Ala Arg Leu Gln Glu Trp Asp Asn Phe Tyr
1425                 1430                 1435                 1440

Lys Phe Ser Asn Arg Ala Lys Asn Leu Leu Pro Arg Arg Thr Met Thr
                 1445                 1450                 1455

Leu Thr Tyr Tyr Asp Gly Ile Ser Arg Tyr Met Glu Gly Gln Val Leu
             1460                 1465                 1470

His Leu Gln Lys Gln Ile Lys Glu Gln Ser Glu Asn Ala Gln Ala Ser
        1475                 1480                 1485

Gly Glu Glu Leu Leu Lys Asn Leu Glu Asn Leu Val Ala Gln Asn Thr
        1490                 1495                 1500

Thr Gly Pro Val Phe Cys Pro Arg Leu Tyr His Leu Met Ala Tyr Val
1505                 1510                 1515                 1520

Cys Ile Leu Met Gly Asp Gly Gln Lys Cys Gly Leu Phe Leu Asn Thr
             1525                 1530                 1535

Ala Leu Arg Leu Ser Glu Thr Gln Gly Asn Ile Leu Glu Lys Cys Trp
             1540                 1545                 1550

Leu Asn Met Asn Lys Glu Ser Trp Tyr Ser Thr Ser Glu Leu Lys Glu
        1555                 1560                 1565

Asp Gln Trp Leu Gln Thr Ile Leu Ser Leu Pro Ser Trp Glu Lys Ile
        1570                 1575                 1580

Val Ala Gly Arg Val Asn Ile Gln Asp Leu Gln Lys Asn Lys Phe Leu
1585                 1590                 1595                 1600

Met Arg Ala Asn Thr Val Asp Asn His Phe
                 1605                 1610

<210> SEQ ID NO 12
<211> LENGTH: 5018
<212> TYPE: DNA
<213> ORGANISM: Artificial Sequence
<220> FEATURE:
<223> OTHER INFORMATION: Description of Artificial Sequence:human
      soluble adenylyl cyclase

<400> SEQUENCE: 12
gacagacatg gcgcttcagc tgtcttcaga ataatgtcac ccggcctcct ctcctgtctt      60
ctgcagtctt aaaagaccta gtccctaact gaggtctggc ttttcctcag ccctggatga    120
agtggagaag acctatttgg agactgcttc ctgtcaccat aaaatcctga acatttgtct    180
tgaacatgaa cactccaaaa gaagaattcc aggactggcc catagtcaga atagcagctc    240
atttaccaga cctcattgtc tatggacatt tctccccaga gcgaccecttt atggattatt    300 ttgacggagt cctgatgttt gttgatattt caggttttac tgcaatgact gagaagttca    360

```
gcagtgccat gtacatggac agaggggctg agcagttggt ggagatcctc aactaccaca      420
taagtgcaat agtggagaaa gtgttgattt ttggaggaga catcctgaaa tttgcaggtg      480
atgcactgct agccctgtgg agggtggagc gaaagcagct gaaaaacatt atcacagtgg      540
taattaaatg tagcctggag atccatggat tgtttgagac ccaggagtgg gaagaaggcc      600
tagacatccg agtcaagata ggactggctg ctggccacat cagcatgttg gtctttggag      660
atgaaacaca cagccacttt ctggtgattg gtcaggcagt ggacgatgtg cgccttgccc      720
agaacatggc tcagatgaat gatgttattc tgtcaccaaa ctgctggcag ctctgtgacc      780
ggagcatgat tgaaattgag agtgttccag atcagagagc agttaaggtt aacttcttaa      840 aaccacccc caattttaat tttgatgaat ttttcacaaa gtgtacgacc ttcatgcatt       900
attatccttc tggtgagcac aaaaacctcc tgaggcttgc atgcacgctg aagcctgatc      960
ctgaactgga gatgtcccta caaaagtatg tgatggaaag cattttgaag cagattgata     1020
acaaacagct tcagggctat ttatctgagc ttcgcccagt gacgattgtg tttgtgaacc     1080
tgatgtttga agaccaagac aaagcagaag agataggccc agcyatccag gatgcctata     1140
tgcacatcac ttctgtcctg aagatcttcc aaggccaaat caataaagtc ttcatgtttg     1200
acaagggctg ctcttcctc tgtgtctttg gcttccctgg ggaaaaggta cctgacgagc      1260
tcactcatgc tctgaatgt gctatggata tatttgactt ctgctctcaa gtccacaaaa      1320
tccaaactgt atccatcggc gttgccagtg ggattgtctt ctgtgggatc gttggacaca     1380
ctgtgagaca cgagtacaca gtcattggtc aaaaagtcaa cttagctgcc aggatgatga     1440
tgtactaccc aggaattgtg acctgcgact ctgtcaccta caatgggagc aacctaccag     1500 cgtactttt taaagagctt ccaaagaaag ttatgaaagg tgttgcagat tctggaccat      1560
tgtatcagta ttggggccgt actgagaaag tcatgtttgg tatggcgtgc ctcatctgca     1620
acagaaagga ggattaccct ttgctgggac gtaataaaga gatcaactac ttcatgtata     1680
ctatgaagaa attttgata tctaacagca gccaagtctt aatgtatgag ggattaccag      1740
gatatggaaa aagccagata cttatgaaaa ttgagtacct ggcccaaggt aagaatcaca     1800
ggattattgc catttcattg aataagatca gcttccatca aactttctat accatccaga     1860
tgttcatggc caatgtccta ggcctagaca cttgtaaaca ttataaagaa cgacagacca     1920
accttcgaaa taaagtcatg acactgttgg atgaaaagtt ctactgtctt cttaatgaca     1980
ttttccatgt tcagttccct atttctcggg agatttccag gatgagcacc ttgaaaaagc     2040
aaaaacaatt ggaaatattg tttatgaaga tcttgaagct gatagtgaaa gaggaaagga     2100
ttatttttat cattgatgag gcccagtttg tggattcgac ctcctggaga ttcatggaga     2160
agcttatccg gactcttcct atcttcatca ttatgtccct gtgtcccttc gttaacattc     2220
cctgtgcagc tgccagggcc gtaataaaga acaggaacac cacctacatt gtcgttggtg     2280
cagtacagcc taacgacatc tccaacaaga tctgtcttga cctcaatgtg agctgcatct     2340
ccaaagaact ggactcgtac ctgggggagg gaagctgtgg gattccattt tactgtgaag     2400
aattgcttaa aaacctggaa catcatgagg tactcgtttt ccaacaaacg gagtctgagg     2460
aaaagacaaa taggacctgg aataacctgt tcaagtattc cattaagcta acagagaagt     2520
taaacatggt tactctccat agtgataagg aaagtgaaga agtctgtcac ctcacaagtg     2580
gcgtcagact gaaaaacctg tcacctccaa cgtcattaaa agaaatctct ctgatccagc     2640
tggatagcat gagactttcc caccaaatgc tggtgagatg tgctgccatc attggcctga     2700
ccttcaccac tgagttgttg tttgagattc tcccctgttg gaatatgaag atgatgatca     2760
```

-continued

```
agaccctggc aaccctagtg gaatctaaca ttttttattg tttccggaat ggcaaggagc    2820
ttcaaaaggc cctgaaacag aatgatccct catttgaggt gcactatcgt tccttgtctc    2880
tgaagcccag tgaagggatg gatcacggtg aagaggaaca gcttcgtgaa ctggagaatg    2940
aggtgatcga gtgccacagg atccgattct gtaaccctat gatgcagaaa acagcctacg    3000
agctgtggct caaggaccag agaaaagcca tgcacttgaa atgtgcccgc tttttagaag    3060
aagatgccca cagatgtgac cactgccgag gcagggactt cattccctat catcacttca    3120
cagtgaatat tcggctcaac gctttagaca tggatgccat taaaaagatg gctatgtctc    3180
atggatttaa aactgaagaa aagcttatct tgtccaactc agagattcct gagacatctg    3240
cattttttcc tgaaatcgc agtcctgaag aaataagaga aaagatcttg aatttctttg    3300
accacgtttt aacaaaaatg aagacatctg acgaagacat tatccctctg gaatcttgcc    3360
agtgtgaaga atcctagag attgtcatct tgcctctggc ccaccatttt ctggctttgg    3420
gagaaaatga caaagcctta tattacttct tagaaattgc atctgcttat ctcatctttt    3480
gtgataacta catggcatac atgtatttga atgaaggaca gaagttgcta aaaactctca    3540
agaaggacaa atcttggagc cagacatttg agtctgccac cttttacagc ctcaaaggtg    3600
aggtctgttt caatatgggc cagatagtgc ttgccaagaa aatgctgagg aaggcactga    3660
agctcctcaa ccgaatcttt ccttacaact taatctcctt gtttctccat atccatgtcg    3720
agaaaaacag acactttcat tatgtgaatc ggcaggccca agagagccca cctccaggga    3780
agagaggct ggcacaactt taccggcaaa ctgtctgcct ttccttgctg tggcgcatct    3840
atagctacag ttatctttt cactgcaagt attatgccca cctggcagtt atgatgcaaa    3900
tgaatactgc actggaaact caaaattgtt tccagatcat taaggcttac ctagactatt    3960
cgctatacca ccacctggct ggctacaaag gtgtgtggtt caaatatgaa gtcatggcca    4020
tggagcacat cttcaacctc cccctgaaag gcgagggcat tgaaatcgtg gcatacgtgg    4080
ctgagacact ggtcttcaac aagctcataa tgggacacct ggatttggcc attgagttag    4140
gctcccgagc ccttcagatg tgggcactgc tccagaatcc caaccgacat tatcagtccc    4200
tctgcagact tagcagatgt ctccttctga acagcagata cccgcaattg atccaggtgc    4260
tgggcggct gtgggagctt tctgtaacac aggaacacat cttcagcaag gcatttttct    4320
attttgtctg cttggacatc ctgctttatt ctggttttgt ttatagaaca tttgaagaat    4380
gtttggaatt catacaccaa tacgaaaaca acagaatcct caagttccac agtggactcc    4440
tcctgggact ttattcctct gtagctatct ggtatgccag acttcaggaa tgggacaact    4500
tttacaaatt ttccaataga gctaaaaatc ttttgccaag aagaaccatg acacttactt    4560
actatgacgg aatatctagg tacatggagg ggcaagttct tcaccttcaa aaacaaatca    4620
aagaacagtc agagaatgcc caagccagtg gggaggagct actcaagaac ttggagaatc    4680
tggtggctca aaataccact ggccctgtct tttgcccaag gctctaccac ctgatggctt    4740
acgtctgtat attaatggga gatgggcaga atgtggcct cttcctgaac acagccttgc    4800
ggctctctga aacacagggg aatatactgg agaaatgctg gctgaacatg aacaaagaat    4860
catggtactc aacctctgag ttaaaagaag accaatggct tcagacgatc ttgagtctcc    4920
catcatggga aaaattgta gcaggcaggg taaacattca ggatcttcaa aaaaacaaat    4980
tcctgatgag agctaatacc gtggacaatc atttctaa                            5018
```